(12) United States Patent
Yamaguchi et al.

(10) Patent No.: US 11,149,066 B2
(45) Date of Patent: Oct. 19, 2021

(54) THROMBOSPONDIN 1-BINDING PEPTIDE

(71) Applicants: DAIICHI SANKYO COMPANY, LIMITED, Tokyo (JP); PeptiDream Inc., Kanagawa (JP)

(72) Inventors: Takahiro Yamaguchi, Tokyo (JP); Yutaka Mori, Tokyo (JP); Hironao Saito, Tokyo (JP); Hideki Kubota, Tokyo (JP); Akihiro Furukawa, Tokyo (JP); Eri Otsuka, Tokyo (JP); Yutaka Ishigai, Tokyo (JP); Hiroshi Ijiri, Kanagawa (JP); Patrick Reid, Kanagawa (JP)

(73) Assignees: DAIICHI SANKYO COMPANY, LIMITED, Tokyo (JP); PEPTIDREAM INC., Kanagawa (JP)

( * ) Notice: Subject to any disclaimer, the term of this patent is extended or adjusted under 35 U.S.C. 154(b) by 0 days.

(21) Appl. No.: 16/332,746

(22) PCT Filed: Sep. 13, 2017

(86) PCT No.: PCT/JP2017/032984
§ 371 (c)(1),
(2) Date: Mar. 12, 2019

(87) PCT Pub. No.: WO2018/052002
PCT Pub. Date: Mar. 22, 2018

(65) Prior Publication Data
US 2020/0131230 A1 Apr. 30, 2020

(30) Foreign Application Priority Data

Sep. 13, 2016 (JP) .............................. JP2016-178955

(51) Int. Cl.
*C07K 7/64* (2006.01)
*A61K 38/00* (2006.01)

(52) U.S. Cl.
CPC ................ *C07K 7/64* (2013.01); *A61K 38/00* (2013.01)

(58) Field of Classification Search
CPC .......... C07K 7/64; A61K 38/00; A61K 38/12; A61P 43/00; A61P 9/10
See application file for complete search history.

(56) References Cited

U.S. PATENT DOCUMENTS 5,190,920 A 3/1993 Eyal et al.
9,308,236 B2 * 4/2016 Miller ...................... C07K 7/08
(Continued)

FOREIGN PATENT DOCUMENTS

| JP | H04-288020 A | 10/1993 |
| JP | 2007-524598 A | 8/2007 |

(Continued)

OTHER PUBLICATIONS

Chan et al., "Cyclic Thrombospondin-1 Mimetics: Grafting of a Thrombospondin Sequence Into Circular Disulfide-Rich Frameworks Into Inhibit Endothelial Cell Migration", Bioscience Reports, (2015), vol. 35, No. 6, pp. 1-12.
Extended European Search Report received in EP Patent Application No. 17850903, dated Apr. 9, 2020.
International Search Report as cited in International Application No. PCT/JP2017/032984 dated Dec. 19, 2017.
Varma, V., et al., "Thrombospondin-1 Is an Adipokine Associated With Obesity, Adipose Inflammation, and Insulin Resistance", Diabetes, vol. 57, No. 2, pp. 432-439, Feb. 2008.
Camus, S.M., et al. "Erythrocyte microparticles can induce kidney vaso-occlusions in a murine model of sickle cell disease", Blood, vol. 120, No. 25, pp 5050-5058, Dec. 13, 2012.
(Continued)

*Primary Examiner* — Sudhakar Katakam
(74) *Attorney, Agent, or Firm* — Arent Fox LLP

(57) ABSTRACT

Provided is a compound that can promote angiogenesis by inhibiting the function of TSP1, and is useful for the treatment or prophylaxis of diseases such as critical limb ischemia.

Specifically provided is a macrocyclic polypeptide represented by formula (I)

[Chem. 1]

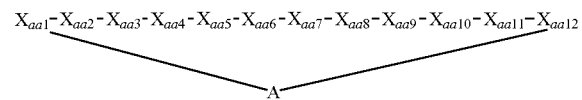

[wherein A is selected from the linking groups $A_1$ to $A_6$; $X_{aa1}$ is a residue of an aliphatic amino acid, an aromatic amino acid, a basic amino acid, a neutral amino acid, or an acidic amino acid, or is absent; $X_{aa2}$ is a residue of an aromatic amino acid or a neutral amino acid; $X_{aa3}$ is a residue of an aliphatic amino acid, an aromatic amino acid, or a basic amino acid; $X_{aa4}$ is Ser, Thr, Ala, or $^mS$; $X_{aa5}$ is Gly or Ser; $X_{aa6}$ is a residue of a basic amino acid or a neutral amino acid; $X_{aa7}$ is a residue of a neutral amino acid or an acidic amino acid; $X_{aa8}$ is a residue of an aromatic amino acid; $X_{aa9}$ is a residue of an aliphatic amino acid, a neutral amino acid, or an aromatic amino acid; $X_{aa10}$ is a residue of a basic amino acid, an aliphatic amino acid, an aromatic amino acid, or a neutral amino acid; $X_{aa11}$ is a residue of an aromatic amino acid; and $X_{aa12}$ is a residue of an aliphatic amino acid, an aromatic amino acid, or a basic amino acid], or a pharmacologically acceptable salt thereof.

16 Claims, No Drawings
Specification includes a Sequence Listing.

(56) References Cited

U.S. PATENT DOCUMENTS

| | | | |
|---|---|---|---|
| 9,850,283 B2* | 12/2017 | Miller | A61P 31/22 |
| 9,879,046 B2* | 1/2018 | Miller | C07K 7/56 |
| 2003/0171298 A1 | 9/2003 | Williams et al. | |
| 2005/0214859 A1 | 9/2005 | Dransfield et al. | |
| 2014/0294898 A1* | 10/2014 | Miller | A61P 31/16 |
| | | | 424/278.1 |
| 2014/0296477 A1 | 10/2014 | Dedieu et al. | |
| 2016/0222060 A1 | 8/2016 | Miller et al. | |

FOREIGN PATENT DOCUMENTS

| | | | |
|---|---|---|---|
| JP | 2014-525740 A | 10/2014 | |
| JP | 2016-519662 A | 6/2016 | |
| WO | 0105812 A2 | 1/2001 | |
| WO | WO 2008/060785 A2 | 5/2008 | |
| WO | 2016100285 A1 | 6/2016 | |

OTHER PUBLICATIONS

Csanyi, G., et al., "Thrombospondin-1 Regulates Blood Flow via CD47 Receptor-Mediated Activation of NADPH Oxidase 1", Arterioscler Thromb Vasc Biol. vol. 32, pp. 2966-2973, Dec. 2012.

Cui, W., et al., "Interaction of thrombospondin1 and CD36 contributes to obesity-associated podocytopathy", Biochim Biophys Acta., vol. 1852, Issue 7, pp. 1323-1333, 2015.

Davies, M.G., "Critical Limb Ischemia: Cell And Molecular Therapies For Limb Salvage", Methodist DeBakey Cardiovasc Vascular J., vol. 8, No. 4, pp. 20-27, 2012.

Esemuede, N., et al., "The Role of Tthrombospondin-1 In Human Disease", Journal of Surgical Research, vol. 122, pp. 135-142, 2004.

Favier, J., et al., "Critical overexpression of thrombospondin 1 in chronic leg ischaemia", Journal of Pathology, vol. 207, pp. 358-366, 2005.

Hagag, A.A., et al., "Clinical Significance of Assessment of Thrombospondin and Placenta Growth Factor Levels in Patients with Sickle Cell Anemia: Two Centers Egyptian Studies", Mediterr Journal of Hematol Infect Dis., vol. 6, No. 1, e2014044, pp. 1-6, 2014.

Hellsten, Y., et al., "Capillary growth in human skeletal muscle : physiological factors and the balance between pro-angiogenic and angiostatic factors", Biochem. Soc. Trans., vol. 42, No. 6, pp. 1616-1622, 2014.

Henkin, J., et al., "Therapies using anti-angiogenic peptide mimetics of thrombospondin-1", Expert Opinion on Therapeutic Targets, vol. 15, No. 12. pp. 1369-1386, 2011.

Isenberg, J.S., et al., "Increasing Survival of Ischemic Tissue by Targeting CD47", Circ. Res., vol. 100, No. 5, pp. 712-720, 2007.

Jeanne, A., el al., "Identification of TAX2 peptide as a new unpredicted anti-cancer agent", Oncotarget, vol. 6, No. 20, pp. 17981-18000, May 22, 2015.

Jimenez, B., el al., "Signals leading to apoptosis-dependent inhibition of neovascularization by thrombospondin-1", Nature Med., vol. 6, No. 1, pp. 41-48, 2000.

Kinlay, S., "Management of Critical Limb Ischemia", Circ Cardiovasc Interv., vol. 9, e001946, pp. 1-10, 2016.

Li, Y., et al., "Thrombospondin1 Deficiency Reduces Obesity-Associated Inflammation and Improves Insulin Sensitivity in a Diet-Induced Obese Mouse Model", PLoS One, vol. 6, No. 10, e26656, pp. 1-9, Oct. 2011.

Liu, Z., et al., "Thrombospondin-1 (TSP1) Contributes to the Development of Vascular Inflammation by Regulating Monocytic Cell Motility in Mouse Models of Abdominal Aortic Aneurysm", Circ Res. vol. 117, No. 2, pp. 129-141, Jul. 3, 2015.

Murphy-Ullrich, J.E., et al., "Thrombospondins in physiology and disease: New tricks for old dogs", Matrix Biol., vol. 31, No. 3, pp. 152-154, 2012.

Olfert, M., "Physiological Capillary Regression is not Dependent on Reducing VEGF Expression", Microcirculation, vol. 23, pp. 146-156, 2016.

Prakash, P., et al., "Thrombospondin 1 requires von Willebrand factor to modulate arterial thrombosis in mice", Blood, vol. 125, No. 2, pp. 399-406, Jan. 8, 2015.

Smadja, D.M., et al., "Thrombospondin-1 Is a Plasmatic Marker of Peripheral Arterial Disease That Modulates Endothelial Progenitor Cell Angiogenic Properties", Arterioscler Thromb Vasc Biol., vol. 31, pp. 551-559, Mar. 2011.

Soto-Pantoja, D.R., et al., "Thrombospondin-1 and CD47 signaling regulate healing of thermal injury in mice", Matrix Biol., vol. 37, pp 25-34, 2014.

Yao, M.,et al., "Thrombospondin-1 Activation of Signal-Regulatory Protein-α Stimulates Reactive Oxygen Species Production and Promotes Renal Ischemia Reperfusion Injury", J Am Soc Nephrol, vol. 25, No. 6, pp. 1171-1186, 2014.

* cited by examiner

THROMBOSPONDIN 1-BINDING PEPTIDE

TECHNICAL FIELD

The present invention relates to macrocyclic polypeptides or pharmacologically acceptable salts thereof, which can promote angiogenesis by inhibiting the function of an angiogenesis inhibitor (thrombospondin 1/TSP1) and are useful for the treatment or prophylaxis of diseases such as critical limb ischemia.

BACKGROUND ART

Critical limb ischemia (CLI) is a condition in which pain at rest occurs due to the obstruction of blood flow to lower limbs and ulcer or necrosis occurs in the periphery of lower limbs. CLI is classified as stages III to IV and stages 4 to 6, respectively, according to the Fontaine and Rutherford classifications (NPL 1).

CLI has been considered problematic due to poor prognosis and high mortality, and studies have been made on a therapy in CLI patients, in which the progress of ulcer or necrosis of limbs is suppressed by remodeling the vascular system through revascularization in ischemic tissues and delivering oxygen and nutrients to the ischemic tissues (NPL 2). Various attempts have heretofore been made to apply a gene therapy using pro-angiogenic growth factors for CLI, but unlike in animal studies, no such therapy has been demonstrated to show efficacy in clinical trials. In light of such clinical trial results, another focus has been placed on angiostatic factors, proposing a hypothesis on the importance of the balance between pro-angiogenic and angiostatic factors (NPLs 3 and 4).

Thrombospondin 1 (TSP1), a glycoprotein reported to act in an inhibitory manner on angiogenesis, is reported to be released from activated platelets and to be synthesized and secreted by numerous cell types, including endothelial cells, smooth myocytes, renal mesangial cells, tubular cells, and podocytes (NPLs 5 to 7). The expression of TSP1 increases in the blood of peripheral vascular disease patients and in the lower-limb skeletal muscles of CLI patients, and this finding suggests involvement of TSP1 in the progress of ulcer or necrosis in lower limbs of CLI patients (NPLs 8 and 9). Since TSP1 limits blood flow recovery after hindlimb ischemia-reperfusion in rats, and TSP1-deficient mice show enhanced angiogenesis after hindlimb ischemia, it is considered that TSP1 has an inhibitory effect on the blood flow recovery after hindlimb ischemia (NPLs 10 and 11). Further, since TSP1-deficient mice show increased blood flow in wounded areas and increased reduction in wound size, it can be expected that inhibiting TSP1 function has a healing effect on wounds in CLI patients (NPL 12).

TSP1 has not only angiostatic activity but also other pharmacological activities, and is considered to be involved in many diseases. TSP1, secreted from platelets, enhances the levels of PAI-1 in the fibrinolytic system and stimulates thrombogenesis (NPL 13). Obese, insulin-resistant patients show increased TSP1 levels, suggesting that TSP1 acts on macrophages to promote obesity-induced inflammatory responses and exacerbate insulin resistance (NPLs 14 and 15). TSP1 promotes renal podocyte apoptosis and induces podocyte dysfunction (NPL 16). TSP1 binds to signal-regulatory protein-α on non-phagocytic cells, activates NADPH oxidase, limits vasodilatation, and induces renal ischemia reperfusion injury (NPL 17). These results suggest the possibility that TSP1 inhibition may ameliorate myocardial infarction, and inflammation and insulin resistance in obese patients, as well as renal disorders including ischemia-reperfusion injury. Further, platelet-derived microparticles released by TSP1 induce vaso-occlusive crisis in patients with sickle cell disease (NPLs 18 and 19). Furthermore, TSP1 is reported to promote the migration and adhesion of monocytes, contributing to enhanced vascular inflammation during aortic aneurysm development (NPL 20). It is reported that TSP1 may be involved in both the suppression and promotion of cancers through acting on the growth, adhesion and invasion of cancer cells (NPL 21).

Meanwhile, there are some antibodies (PTL 1) and polypeptides (PTL 2) known as antagonists for the binding of TSP1 to the CD47 receptor. However, no macrocyclic polypeptide binding to TSP1 has been known.

CITATION LIST

Patent Literatures

PTL 1: WO 2008/060785
PTL 2: US 2014/296477

NON PATENT LITERATURES

NPL 1: Kinlay S. *Circ Cardiovasc Interv.* 2016; 9: e001946.
NPL 2: Davies M G. *Methodist Debakey Cardiovasc J.* 2012; 8: 20-27.
NPL 3: Hellsten Y, Hoier B. *Biochem. Soc. Trans.* 2014; 42: 1616-1622.
NPL 4: Olfert I M. *Microcirculation* 2016; 23: 146-156.
NPL 5: Jimenez B, Volpert O V, Crawford S E, et al. *Nat Med.* 2000; 6: 41-48.
NPL 6: Henkin J, Volpert O V. *Expert Opin Ther Targets.* 2011; 15(12): 1369-1386.
NPL 7: Murphy-Ullrich J E, Iozzo R V. *Matrix Biol.* 2012; 31(3): 152-154.
NPL 8: Smadja D M, d'Audigier C, Bieche I, et al. *Arterioscler Thromb Vasc Biol.* 2011; 31: 551-559.
NPL 9: Favier J, Germain S, Emmerich J, et al. *J Pathol* 2005; 207: 358-366.
NPL 10: Isenberg J S, Romeo M J, Abu-Asab M, et al. *Circ Res.* 2007; 100(5): 712-720.
NPL 11: Csanyi G, Yao M, Rodriguez A I, et al. *Arterioscler Thromb Vasc Biol.* 2012; 32: 2966-2973.
NPL 12: Soto-Pantoja D R, Shih H B, Maxhimer J B, et al. *Matrix Biol.* 2014; 37: 25-34.
NPL 13: Prakash P, Kulkarni P P, Chauhan A K. *Blood* 2015; 125(2): 399-406.
NPL 14: Varma V, Yao-Borengasser A, Bodies A M, et al. *Diabetes.* 2008; 57(2): 432-439.
NPL 15: Li Y, Tong X, Rumala C, et al. *PLoS One.* 2011; 6(10): e26656.
NPL 16: Cui W, Maimaitiyiming H, Zhou Q, et al. *Biochim Biophys Acta.* 2015; 1852(7): 1323-1333.
NPL 17: Yao M, Rogers N M, Csanyi G, et al. *J Am Soc Nephrol.* 2014; 25(6): 1171-1186.
NPL 18: Hagag A A, Elmashad G, Abd El-Lateef AE. *Mediterr J Hematol Infect Dis.* 2014; 6(1): e2014044.
NPL 19: Camus S M, Gausseres B, Bonnin P, et al. *Blood.* 2012; 120(25): 5050-5058.
NPL 20: Liu Z, Morgan S, Ren J, et al. *Circ Res.* 2015; 117(2): 129-141.
NPL 21: Esemuede N, Lee T, Pierre-Paul D. et al., The role of thrombospondin-1 in human disease. *J Surg Res.* 2004; 122(1): 135-42.

SUMMARY OF INVENTION

Technical Problem

An object of the present invention is to provide compounds that can promote angiogenesis by inhibiting the function of TSP1 and are useful for the treatment or prophylaxis of diseases such as critical limb ischemia.

Solution to Problem

The present inventors have made intensive studies to achieve the aforementioned object, and as a result, found that macrocyclic polypeptides having particular amino acid sequences bind to TSP1 to block the cell adhesion to TSP1, thereby inhibiting the function of TSP1; and thus the inventors completed this invention.

More specifically, the present invention provides [1] to [34] as follows.

[1] A macrocyclic polypeptide represented by formula (I)

[Chem. 1]

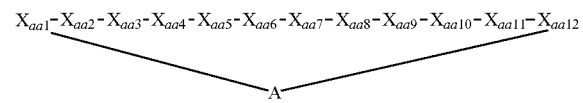

[wherein A is selected from the linking groups of the formulas:

[Chem. 2]

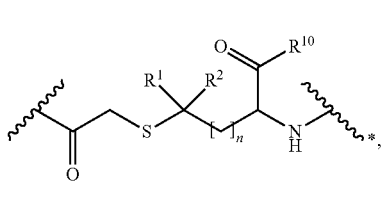 $A_1$

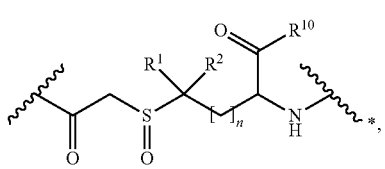 $A_2$

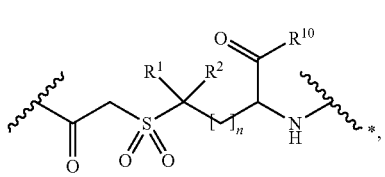 $A_3$

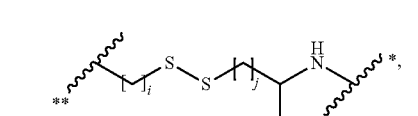 $A_4$

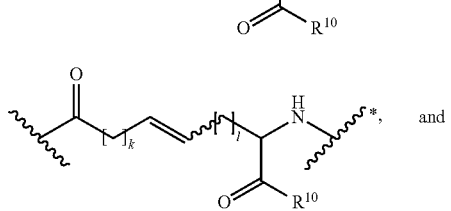 $A_5$ and

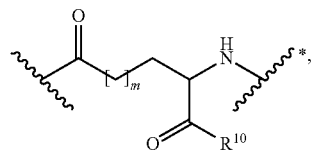 $A_6$ wherein

[Chem. 3]

represents a point of attachment to the N-terminal amino group of $X_{aa1}$, or in the absence of $X_{aa1}$, represents a point of attachment to the N-terminal amino group of $X_{aa2}$,

[Chem. 4]

* represents a point of attachment to the C-terminal carbonyl group of $X_{aa12}$,

[Chem. 5]

**

represents a point of attachment to a carbon of $X_{aa1}$, or in the absence of $X_{aa1}$, represents a point of attachment to a carbon of $X_{aa2}$, $R^1$ and $R^2$ are each independently a hydrogen atom or $C_{1-3}$ alkyl, $R^{10}$ is amino or hydroxy, n is an integer of 0 to 3, i and j are each independently an integer of 1 to 3, k and l are each independently an integer of 0 to 3, m is an integer of 1 to 7;

$X_{aa1}$ is a residue of an aliphatic amino acid, an aromatic amino acid, a basic amino acid, a neutral amino acid, or an acidic amino acid, or is absent;

$X_{aa2}$ is a residue of an aromatic amino acid or a neutral amino acid;

$X_{aa3}$ is a residue of an aliphatic amino acid, an aromatic amino acid, or a basic amino acid;

$X_{aa4}$ is Ser, Thr, Ala, or $^mS$;

$X_{aa5}$ is Gly or Ser;

$X_{aa6}$ is a residue of a basic amino acid or a neutral amino acid;

$X_{aa7}$ is a residue of a neutral amino acid or an acidic amino acid;

$X_{aa8}$ is a residue of an aromatic amino acid;

$X_{aa9}$ is a residue of an aliphatic amino acid, a neutral amino acid, or an aromatic amino acid;

$X_{aa10}$ is a residue of a basic amino acid, an aliphatic amino acid, an aromatic amino acid, or a neutral amino acid;

$X_{aa11}$ is a residue of an aromatic amino acid;

$X_{aa12}$ is a residue of an aliphatic amino acid, an aromatic amino acid, or a basic amino acid;

wherein the aliphatic amino acid is an amino acid represented by formula (IIa)

[Chem. 6]

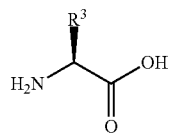

(IIa)

(wherein $R^3$ is $C_{1-6}$ alkyl, $C_{2-6}$ alkenyl or $C_{3-6}$ cycloalkyl);
the aromatic amino acid is an amino acid represented by formula (IIb)

[Chem. 7]

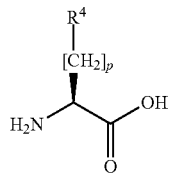

(IIb)

(wherein $R^4$ is an aromatic group selected from phenyl, thienyl, naphthyl, indolyl, benzofuranyl, and benzothienyl, wherein the aromatic group may be substituted with one or more substituents independently selected from the group consisting of $C_{1-3}$ alkyl, halogen atoms, hydroxy, and $C_{1-3}$ alkoxy; and p is an integer of 0 to 3);
the basic amino acid is an amino acid represented by formula (IIc)

[Chem. 8]

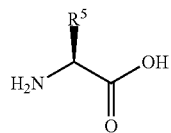

(IIc)

[wherein $R^5$ is a group represented by
the formula —$(CH_2)_{qa}NH_2$ (wherein qa is an integer of 1 to 6),
the formula

[Chem. 9]

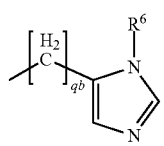

(wherein $R^6$ is a hydrogen atom or $C_{1-3}$ alkyl, and qb is an integer of 1 to 6), the formula —$(CH_2)_{qc}NHC(=NH)NH_2$ (wherein qc is an integer of 1 to 6), or the formula

[Chem. 10]

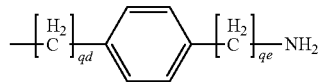

(wherein qd and qe are each independently an integer of 1 to 3)];
the neutral amino acid is an amino acid represented by formula (IId)

[Chem. 11]

(IId)

[wherein $R^7$ is a group represented by the formula —$(CH_2)_{ra}NHCONH_2$ (wherein ra is an integer of 1 to 6) or the formula —$(CH_2)_{rb}SH$ (wherein rb is an integer of 1 to 3)], Gly, Met, MO1, MO2, Pro, 3Hyp, Asn, Gln, Ser, $^mS$, MS, Thr, C(O), C(O2), or Pen;
the acidic amino acid is an amino acid represented by formula (IIe)

[Chem. 12]

(IIe)

[wherein $R^8$ is a group represented by the formula —$(CH_2)_sCOOH$ (wherein s is an integer of 1 to 6)]], or a pharmacologically acceptable salt thereof.

The macrocyclic polypeptide or pharmacologically acceptable salt thereof as set forth in [1], wherein $X_{aa4}$ is Ser.

The macrocyclic polypeptide or pharmacologically acceptable salt thereof as set forth in [1] or [2], wherein $X_{aa5}$ is Gly.

The macrocyclic polypeptide or pharmacologically acceptable salt thereof as set forth in any of [1] to [3], wherein $X_{aa8}$ is Trp, 2Nal, or 6CW.

The macrocyclic polypeptide or pharmacologically acceptable salt thereof as set forth in [4], wherein $X_{aa8}$ is Trp.

The macrocyclic polypeptide or pharmacologically acceptable salt thereof as set forth in any of [1] to [5], wherein $X_{aa11}$ is Trp or 2Nal.

The macrocyclic polypeptide or pharmacologically acceptable salt thereof as set forth in [6], wherein $X_{aa11}$ is Trp.

The macrocyclic polypeptide or pharmacologically acceptable salt thereof as set forth in any of [1] to [7], wherein $X_{aa1}$ is Arg, Lys, His, Gly, Ala, Asn, Thr, Ser, Met, Leu, Ile, Val, Gln, Phe, Tyr, Trp, or Cys, or is absent.

The macrocyclic polypeptide or pharmacologically acceptable salt thereof as set forth in [8], wherein $X_{aa1}$ is Arg, Lys, or Gly, or is absent.

The macrocyclic polypeptide or pharmacologically acceptable salt thereof as set forth in any of [1] to [9], wherein $X_{aa2}$ is Phe, Tyr, Trp, 2Nal, 4CF, or DCF.

The macrocyclic polypeptide or pharmacologically acceptable salt thereof as set forth in [10], wherein $X_{aa2}$ is 2Nal.

The macrocyclic polypeptide or pharmacologically acceptable salt thereof as set forth in any of [1] to [11], wherein $X_{aa3}$ is Ile, Leu, Nle, Tle, Trp, 2Nal, 4CF, or Arg.

The macrocyclic polypeptide or pharmacologically acceptable salt thereof as set forth in [12], wherein $X_{aa3}$ is Ile, or Arg.

The macrocyclic polypeptide or pharmacologically acceptable salt thereof as set forth in any of [1] to [13], wherein $X_{aa6}$ is Arg, Lys, His, Ser, Cit, or MO2.

The macrocyclic polypeptide or pharmacologically acceptable salt thereof as set forth in [14], wherein $X_{aa6}$ is Arg, Lys, His, or Ser.

The macrocyclic polypeptide or pharmacologically acceptable salt thereof as set forth in any of [1] to [15], wherein $X_{aa7}$ is Asn or Asp.

The macrocyclic polypeptide or pharmacologically acceptable salt thereof as set forth in any of [1] to [16], wherein $X_{aa9}$ is Val, Nle, Ahp, or Met.

The macrocyclic polypeptide or pharmacologically acceptable salt thereof as set forth in [17], wherein $X_{aa9}$ is Val, Nle, or Ahp.

The macrocyclic polypeptide or pharmacologically acceptable salt thereof as set forth in any of [1] to [18], wherein $X_{aa10}$ is Arg, Lys, His, AMF, Phg, or Val.

The macrocyclic polypeptide or pharmacologically acceptable salt thereof as set forth in [19], wherein $X_{aa10}$ is Arg, Lys, His, Phg, or Val.

The macrocyclic polypeptide or pharmacologically acceptable salt thereof as set forth in any of [1] to [20], wherein $X_{aa12}$ is Val, Tle, or Phe.

The macrocyclic polypeptide or pharmacologically acceptable salt thereof as set forth in [21], wherein $X_{aa12}$ is Val.

The macrocyclic polypeptide or pharmacologically acceptable salt thereof as set forth in any of [1] to [22], wherein A is a linking group of the formula:

[Chem. 13]

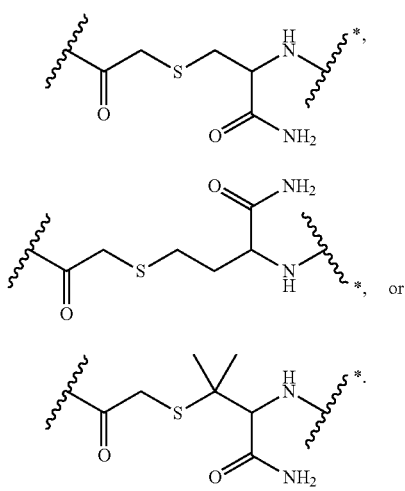

The macrocyclic polypeptide or pharmacologically acceptable salt thereof as set forth in [23], wherein A is

[Chem. 14]

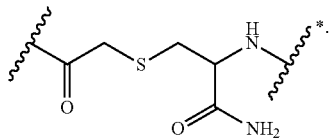

The macrocyclic polypeptide or pharmacologically acceptable salt thereof as set forth in [1], wherein $X_{aa1}$ is Arg, Lys, His, Gly, Ala, Asn, Thr, Ser, Met, Leu, Ile, Val, Gln, Phe, Tyr, Trp, or Cys, or is absent;
$X_{aa2}$ is Phe, Tyr, Trp, 2Nal, 4CF, or DCF;
$X_{aa3}$ is Ile, Leu, Nle, Tle, Trp, 2Nal, 4CF, or Arg;
$X_{aa4}$ is Ser;
$X_{aa5}$ is Gly;
$X_{aa6}$ is Arg, Lys, His, Ser, Cit, or MO2;
$X_{aa7}$ is Asn or Asp;
$X_{aa8}$ is Trp, 2Nal, or 6CW;
$X_{aa9}$ is Val, Nle, Ahp, or Met;
$X_{aa10}$ is Arg, Lys, His, AMF, Phg, or Val;
$X_{aa11}$ is Trp or 2Nal;
$X_{aa12}$ is Val, Tle, or Phe;
A is a linking group of the formula:

[Chem. 15]

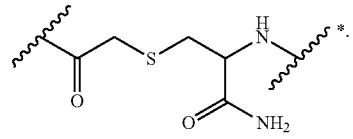

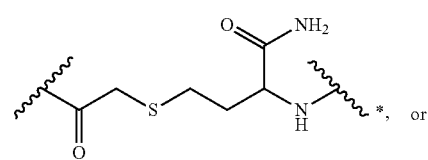

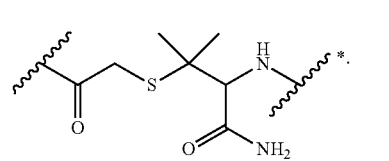

The macrocyclic polypeptide or pharmacologically acceptable salt thereof as set forth in [25], wherein $X_{aa1}$ is Arg, Lys, or Gly, or is absent;
$X_{aa2}$ is 2Nal;
$X_{aa3}$ is Ile, or Arg;
$X_{aa4}$ is Ser;
$X_{aa5}$ is Gly;
$X_{aa6}$ is Arg, Lys, His, or Ser;
$X_{aa7}$ is Asn or Asp;
$X_{aa8}$ is Trp;
$X_{aa9}$ is Val, Nle, or Ahp;
$X_{aa10}$ is Arg, Lys, His, Phg, or Val;
$X_{aa11}$ is Trp;
$X_{aa12}$ is Val;

A is
[Chem. 16]
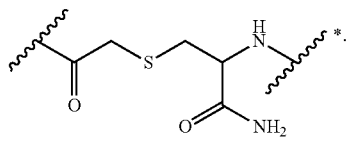
The macrocyclic polypeptide or pharmacologically acceptable salt thereof as set forth in [26], wherein the macrocyclic polypeptide or pharmacologically acceptable salt thereof is selected from the group consisting of the compounds represented by the formulas:
[Chem. 17]
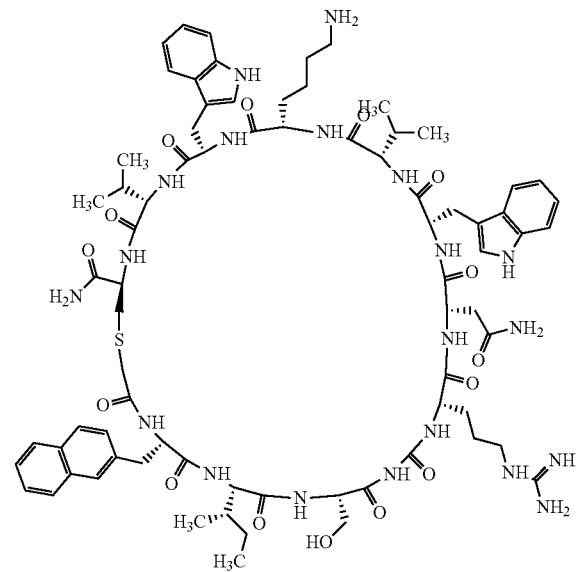
[Chem. 18]
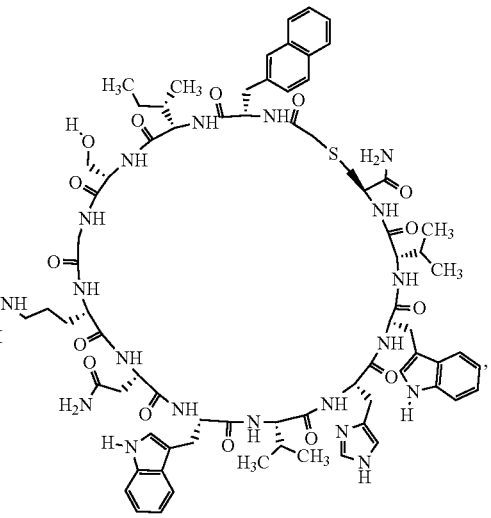
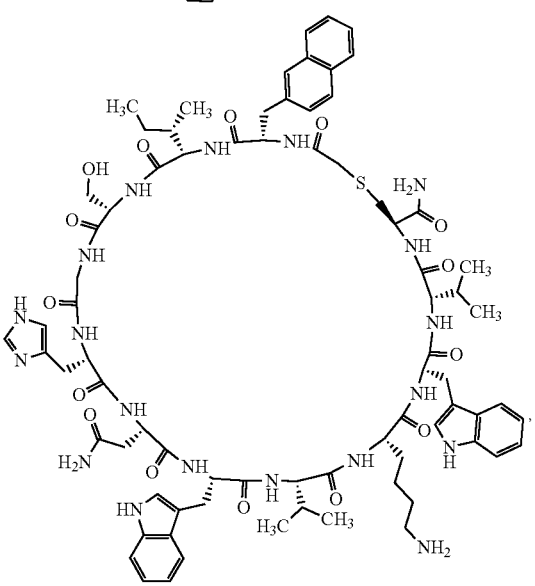
[Chem. 19]
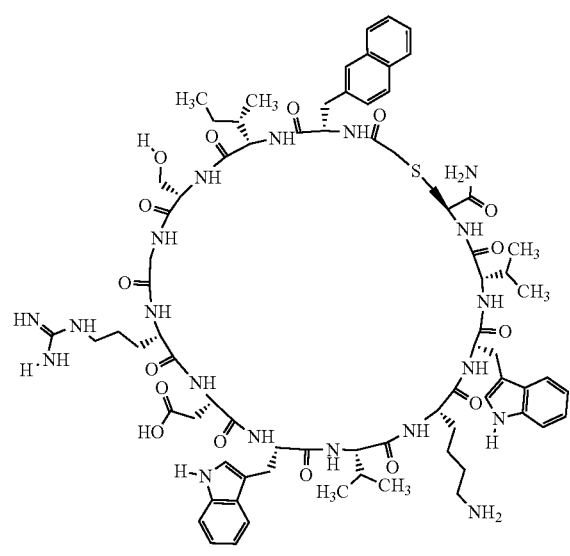
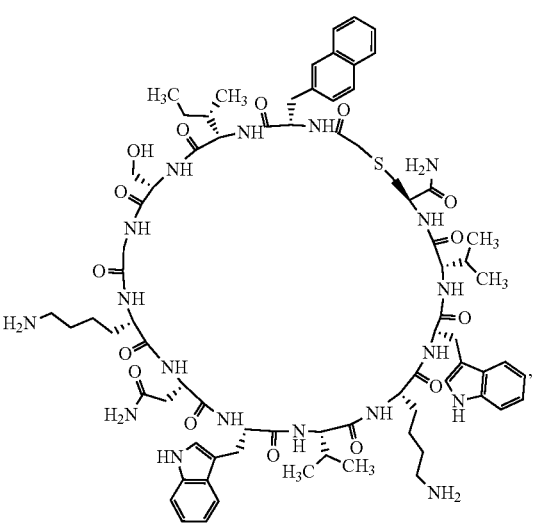

-continued
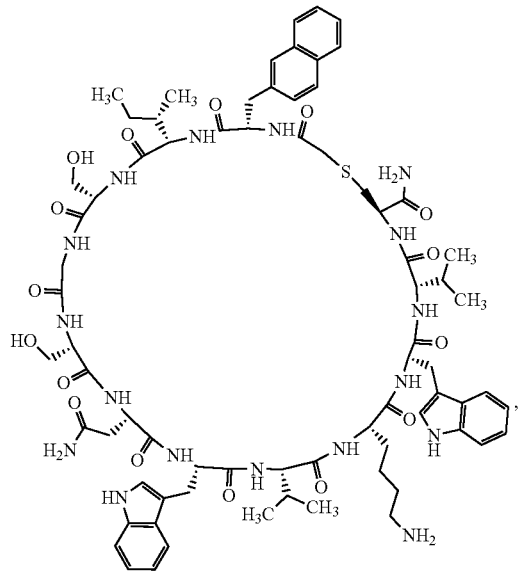
[Chem. 20]
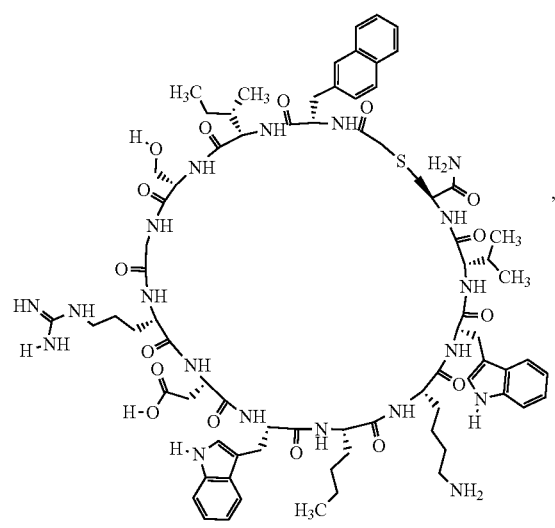
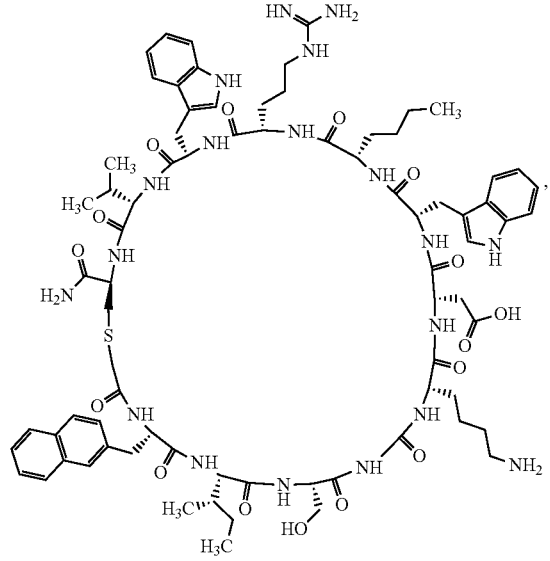
[Chem. 21]
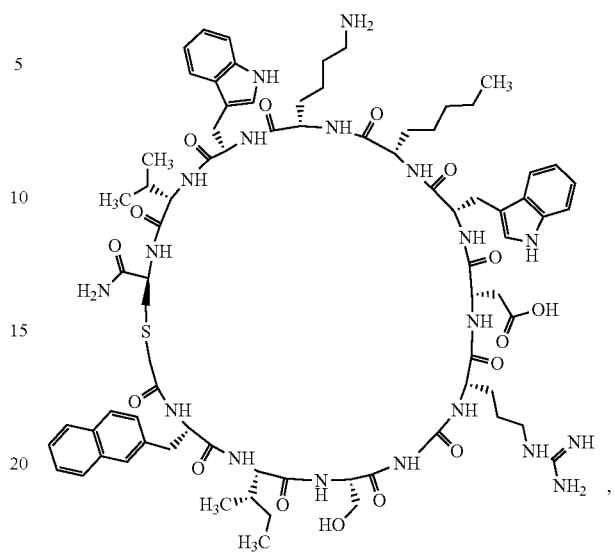
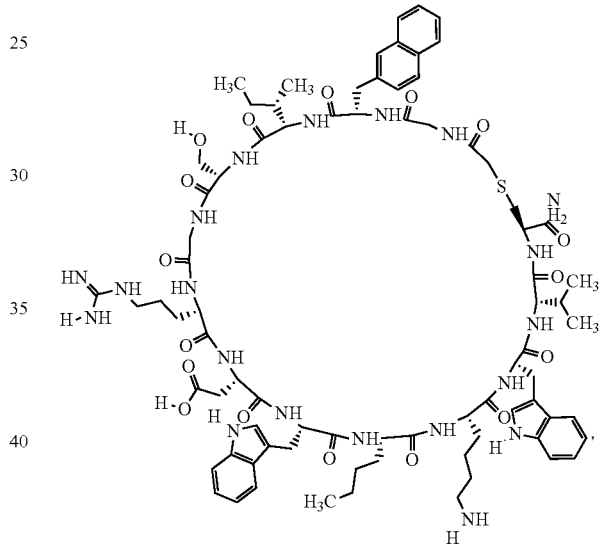
[Chem. 22]
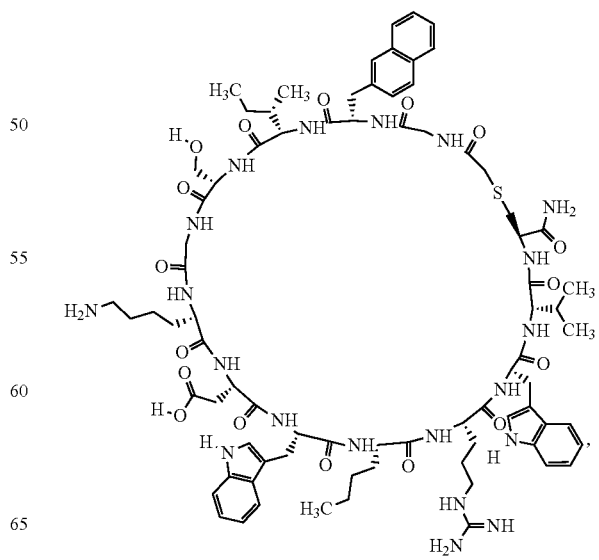

-continued
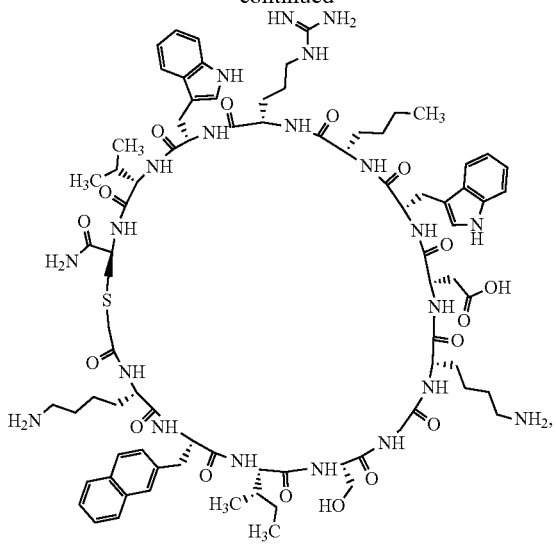
[Chem. 23]
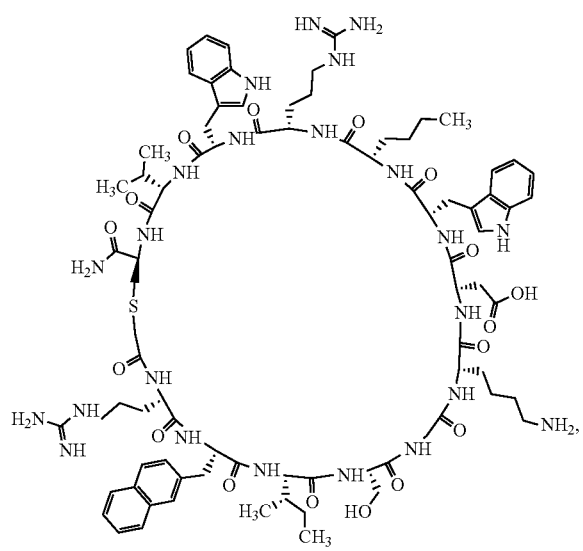
[Chem. 24]
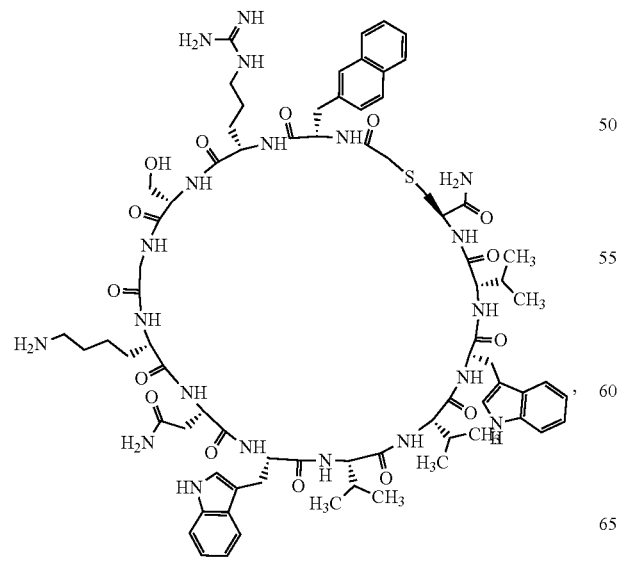
[Chem. 25]
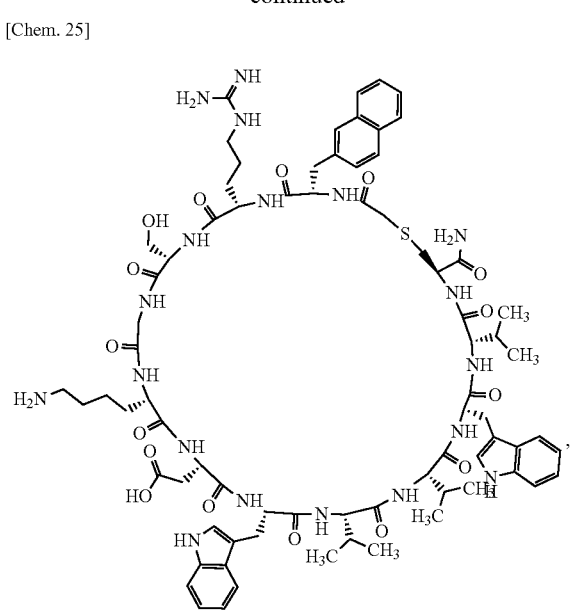
[Chem. 26]
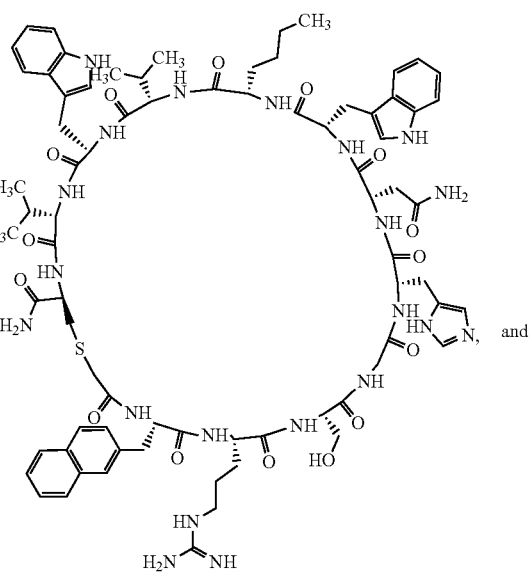

[Chem. 27]

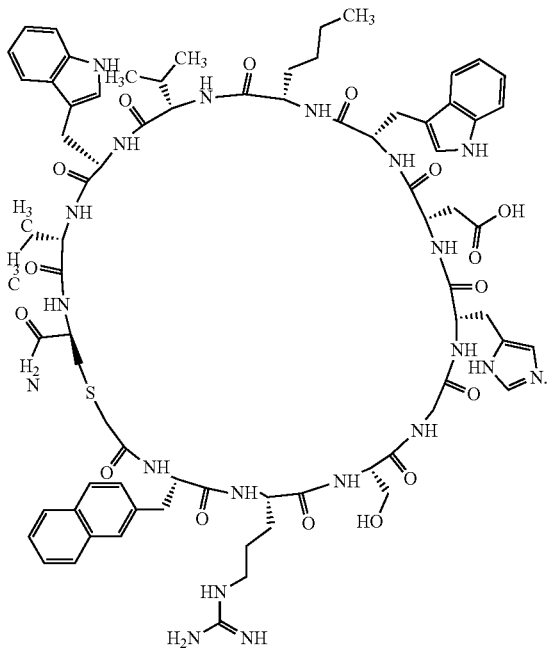

A pharmaceutical composition comprising, as an active component, the macrocyclic polypeptide or pharmacologically acceptable salt thereof as set forth in any of [1] to [27].

The pharmaceutical composition as set forth in [28], wherein the pharmaceutical composition is for use in the treatment or prophylaxis of critical limb ischemia or peripheral arterial disease.

An angiogenesis promoter comprising, as an active component, the macrocyclic polypeptide or pharmacologically acceptable salt thereof as set forth in any of [1] to [27].

A method for the treatment or prophylaxis of a disease or symptom, the method comprising administering to a human a therapeutically or prophylactically effective amount of the macrocyclic polypeptide or pharmacologically acceptable salt thereof as set forth in any of [1] to [27].

The method as set forth in [31], wherein the disease or symptom is critical limb ischemia or peripheral arterial disease.

The pharmaceutical composition as set forth in [28], wherein the pharmaceutical composition is for use in the treatment or prophylaxis of critical limb ischemia, peripheral vascular disorder, myocardial infarction, obesity-induced inflammation, inflammation during aortic aneurysm development, diabetic nephropathy, IgA nephropathy, chronic renal failure, acute renal failure, kidney injury, ischemia-reperfusion injury, angina, squamous cancer, breast cancer, pancreatic cancer, vaso-occlusive crisis associated with sickle cell disease, angiogenesis inhibition, tissue necrosis, insulin resistance, or common wounds.

The method as set forth in [31], wherein the disease or symptom is critical limb ischemia, peripheral vascular disorder, myocardial infarction, obesity-induced inflammation, inflammation during aortic aneurysm development, diabetic nephropathy, IgA nephropathy, chronic renal failure, acute renal failure, kidney injury, ischemia-reperfusion injury, angina, squamous cancer, breast cancer, pancreatic cancer, vaso-occlusive crisis associated with sickle cell disease, angiogenesis inhibition, tissue necrosis, insulin resistance, or common wounds.

The macrocyclic polypeptide or pharmacologically acceptable salt thereof as set forth in any of [1] to [27], for use in the treatment or prophylaxis of a disease or symptom.

The macrocyclic polypeptide or pharmacologically acceptable salt thereof as set forth in [35], wherein the disease or symptom is critical limb ischemia or peripheral arterial disease.

Further, the present invention provides [A1] to [A26] as follows. [A1] A macrocyclic polypeptide represented by formula (I)

[Chem. 28]

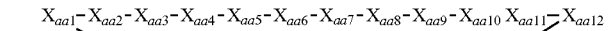

$X_{aa1}-X_{aa2}-X_{aa3}-X_{aa4}-X_{aa5}-X_{aa6}-X_{aa7}-X_{aa8}-X_{aa9}-X_{aa10}-X_{aa11}-X_{aa12}$

[wherein A is selected from the linking groups of the formulas:

[Chem. 29]

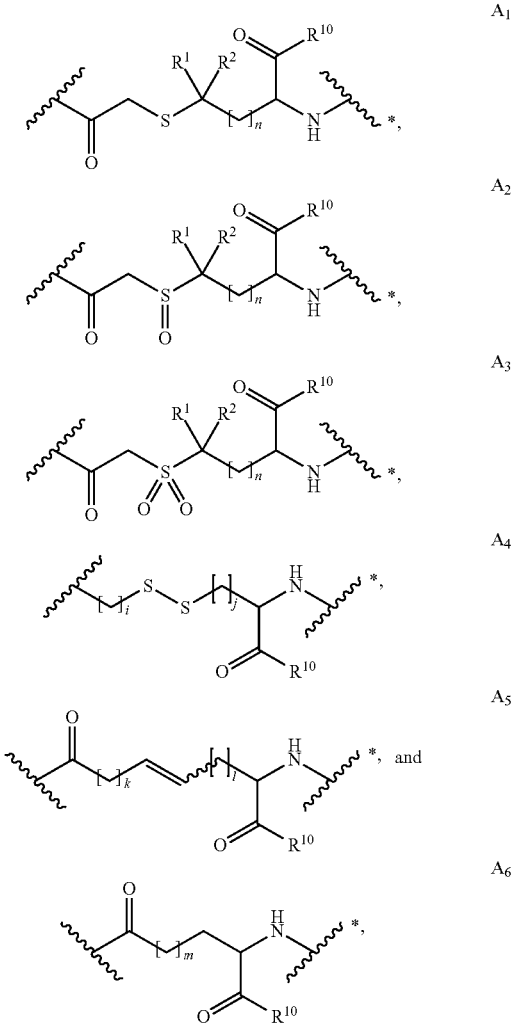

wherein

[Chem. 30]

represents a point of attachment to the N-terminal amino group of $X_{aa1}$, or in the absence of $X_{aa1}$, represents a point of attachment to the N-terminal amino group of $X_{aa2}$,

[Chem. 31]

represents a point of attachment to the C-terminal carbonyl group of $X_{aa12}$,

[Chem. 32]

represents a point of attachment to a carbon of $X_{aa1}$, or in the absence of $X_{aa1}$, represents a point of attachment to a carbon of $X_{aa2}$, $R^1$ and $R^2$ are each independently a hydrogen atom or $C_{1-3}$ alkyl, $R^{10}$ is amino or hydroxy, n is an integer of 0 to 3, i and j are each independently an integer of 1 to 3, k and l are each independently an integer of 0 to 3, m is an integer of 1 to 7;

$X_{aa1}$ is a residue of an aliphatic amino acid, an aromatic amino acid, a basic amino acid, a neutral amino acid, or an acidic amino acid, or is absent;

$X_{aa2}$ is a residue of an aromatic amino acid or a neutral amino acid;

$X_{aa3}$ is a residue of an aliphatic amino acid, an aromatic amino acid, or a basic amino acid;

$X_{aa4}$ is Ser, Thr, Ala, or $^mS$;

$X_{aa5}$ is Gly or Ser;

$X_{aa6}$ is a residue of a basic amino acid or a neutral amino acid;

$X_{aa7}$ is a residue of a neutral amino acid or an acidic amino acid;

$X_{aa8}$ is a residue of an aromatic amino acid;

$X_{aa9}$ is a residue of an aliphatic amino acid, a neutral amino acid, or an aromatic amino acid;

$X_{aa10}$ is a residue of a basic amino acid, an aliphatic amino acid, or a neutral amino acid;

$X_{aa11}$ is a residue of an aromatic amino acid;

$X_{aa12}$ is a residue of an aliphatic amino acid, an aromatic amino acid, or a basic amino acid;

wherein the aliphatic amino acid is an amino acid represented by formula (IIa)

[Chem. 33]

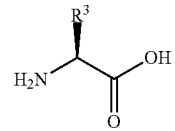

(IIa)

(wherein $R^3$ is $C_{1-6}$ alkyl, $C_{2-6}$ alkenyl or $C_{3-6}$ cycloalkyl);

the aromatic amino acid is an amino acid represented by formula (IIb)

[Chem. 34]

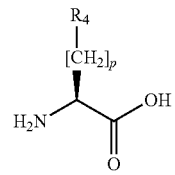

(IIb)

(wherein $R^4$ is an aromatic group selected from phenyl, thienyl, naphtyl, indolyl, benzofuranyl, and benzothienyl, wherein the aromatic group may be substituted with one or more substituents selected from $C_{1-3}$ alkyl, halogen atoms, hydroxy, and $C_{1-3}$ alkoxy; and p is an integer of 0 to 3);

the basic amino acid is an amino acid represented by formula (IIc)

[Chem. 35]

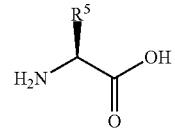

(IIc)

[wherein $R^5$ is a group represented by the formula —$(CH_2)_{qa}NH_2$ (wherein qa is an integer of 1 to 6), the formula

[Chem. 36]

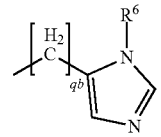

(wherein $R^6$ is a hydrogen atom or $C_{1-3}$ alkyl, and qb is an integer of 1 to 6), the formula —$(CH_2)_{qc}NHC(=NH)NH_2$ (wherein qc is an integer of 1 to 6), or the formula

[Chem. 37]

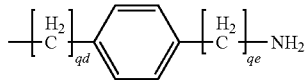

(wherein qd and qe are each independently an integer of 1 to 3)];

the neutral amino acid is an amino acid represented by the formula

[Chem. 38]

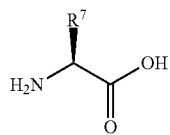

(IId)

[wherein $R^7$ is a group represented by the formula —$(CH_2)_{ra}NHCONH_2$ (wherein ra is an integer of 1 to 6) or the formula —$(CH_2)_{rb}SH$ (wherein rb is an integer of 1 to 3)], Gly, Met, MO1, MO2, Pro, 3Hyp, Asn, Gln, Ser, $^mS$, MS, Thr, C(O), C(O2), or Pen;

the acidic amino acid is an amino acid represented by the formula

[Chem. 39]

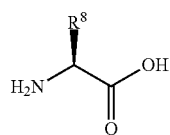

(IIe)

[wherein $R^8$ is a group represented by the formula —$(CH_2)_sCOOH$ (wherein s is an integer of 1 to 6)]], or a pharmacologically acceptable salt thereof.

[A2] The macrocyclic polypeptide or pharmacologically acceptable salt thereof as set forth in [A1], wherein $X_{aa4}$ is Ser.

[A3] The macrocyclic polypeptide or pharmacologically acceptable salt thereof as set forth in [A1] or [A2], wherein $X_{aa5}$ is Gly.

[A4] The macrocyclic polypeptide or pharmacologically acceptable salt thereof as set forth in any of [A1] to [A3], wherein $X_{aa8}$ is Trp, 2Nal, or 6CW.

[A5] The macrocyclic polypeptide or pharmacologically acceptable salt thereof as set forth in [A4], wherein $X_{aa8}$ is Trp.

[A6] The macrocyclic polypeptide or pharmacologically acceptable salt thereof as set forth in any of [A1] to [A5], wherein $X_{aa11}$ is Trp or 2Nal.

[A7] The macrocyclic polypeptide or pharmacologically acceptable salt thereof as set forth in [A6], wherein $X_{aa11}$ is Trp.

[A8] The macrocyclic polypeptide or pharmacologically acceptable salt thereof as set forth in any of [A1] to [A7], wherein $X_{aa1}$ is Arg, Lys, His, Gly, Ala, Asn, Thr, Ser, Met, Leu, Ile, Val, Gln, Phe, Tyr, Trp, or Cys, or is absent.

[A9] The macrocyclic polypeptide or pharmacologically acceptable salt thereof as set forth in [A8], wherein $X_{aa1}$ is Arg, Lys, or Gly, or is absent.

[A10] The macrocyclic polypeptide or pharmacologically acceptable salt thereof as set forth in any of [A1] to [A9], wherein $X_{aa2}$ is Phe, Tyr, Trp, 2Nal, 4CF, or DCF.

[A11] The macrocyclic polypeptide or pharmacologically acceptable salt thereof as set forth in [A10], wherein $X_{aa2}$ is 2Nal.

[A12] The macrocyclic polypeptide or pharmacologically acceptable salt thereof as set forth in any of [A1] to [A11], wherein $X_{aa3}$ is Ile, Leu, Nle, Tle, Trp, 2Nal, 4CF, or Arg.

[A13] The macrocyclic polypeptide or pharmacologically acceptable salt thereof as set forth in [A12], wherein $X_{aa3}$ is Ile.

[A14] The macrocyclic polypeptide or pharmacologically acceptable salt thereof as set forth in any of [A1] to [A13], wherein $X_{aa6}$ is Arg, Lys, His, Ser, Cit, or MO2.

[A15] The macrocyclic polypeptide or pharmacologically acceptable salt thereof as set forth in [A14], wherein $X_{aa6}$ is Arg, Lys, His, or Ser.

[A16] The macrocyclic polypeptide or pharmacologically acceptable salt thereof as set forth in any of [A1] to [A15], wherein $X_{aa7}$ is Asn or Asp.

[A17] The macrocyclic polypeptide or pharmacologically acceptable salt thereof as set forth in any of [A1] to [A16], wherein $X_{aa9}$ is Val, Nle, Ahp, or Met.

[A18] The macrocyclic polypeptide or pharmacologically acceptable salt thereof as set forth in [A17], wherein $X_{aa9}$ is Val, Nle, or Ahp.

[A19] The macrocyclic polypeptide or pharmacologically acceptable salt thereof as set forth in any of [A1] to [A18], wherein $X_{aa10}$ is Arg, Lys, His, AMF, or Val.

[A20] The macrocyclic polypeptide or pharmacologically acceptable salt thereof as set forth in [A19], wherein $X_{aa10}$ is Arg, Lys, or His.

[A21] The macrocyclic polypeptide or pharmacologically acceptable salt thereof as set forth in any of [A1] to [A20], wherein $X_{aa12}$ is Val, Tle, or Phe.

[A22] The macrocyclic polypeptide or pharmacologically acceptable salt thereof as set forth in [A21], wherein $X_{aa12}$ is Val.

[A23] The macrocyclic polypeptide or pharmacologically acceptable salt thereof as set forth in any of [A1] to [A22], wherein A is a linking group of the formula:

[Chem. 40]

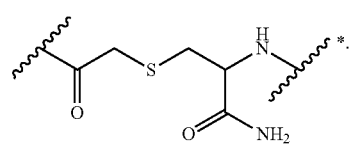

$A_{1a}$

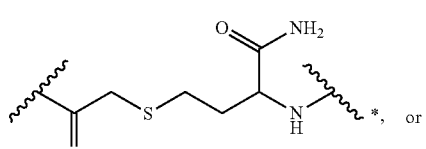

$A_{1b}$, or

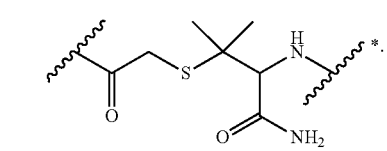

$A_{1c}$

[A24] The macrocyclic polypeptide or pharmacologically acceptable salt thereof as set forth in [A23], wherein A is

[Chem. 41]

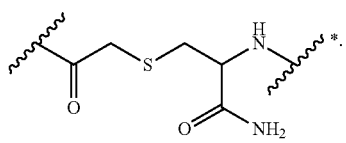

[A25] The macrocyclic polypeptide or pharmacologically acceptable salt thereof as set forth in [A1], wherein $X_{aa1}$ is Arg, Lys, His, Gly, Ala, Asn, Thr, Ser, Met, Leu, Ile, Val, Gln, Phe, Tyr, Trp, or Cys, or is absent;

$X_{aa2}$ is Phe, Tyr, Trp, 2Nal, 4CF, or DCF;
$X_{aa3}$ is Ile, Leu, Nle, Tle, Trp, 2Nal, 4CF, or Arg;
$X_{aa4}$ is Ser;
$X_{aa5}$ is Gly;
$X_{aa6}$ is Arg, Lys, His, Ser, Cit, or MO2;
$X_{aa7}$ is Asn or Asp;
$X_{aa8}$ is Trp, 2Nal, or 6CW;
$X_{aa9}$ is Val, Nle, Ahp, or Met;
$X_{aa10}$ is Arg, Lys, His, AMF, or Val;
$X_{aa11}$ is Trp or 2Nal;
$X_{aa12}$ is Val, Tle, or Phe;
A is a linking group of the formula:

[Chem. 42]

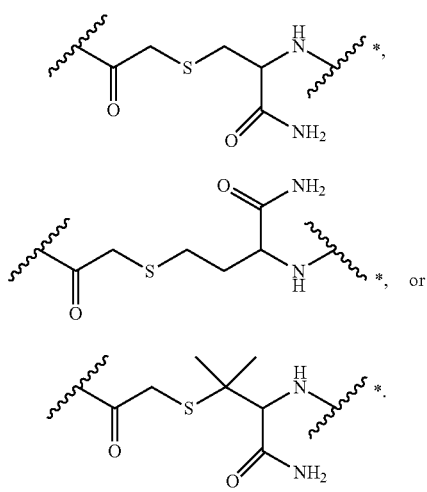

[A26] The macrocyclic polypeptide or pharmacologically acceptable salt thereof as set forth in [A25], wherein $X_{aa1}$ is Arg, Lys, or Gly, or is absent;

$X_{aa2}$ is 2Nal;
$X_{aa3}$ is Ile;
$X_{aa4}$ is Ser;
$X_{aa5}$ is Gly;
$X_{aa6}$ is Arg, Lys, His, or Ser;
$X_{aa7}$ is Asn or Asp;
$X_{aa8}$ is Trp;
$X_{aa9}$ is Val, Nle, or Ahp;
$X_{aa10}$ is Arg or Lys;
$X_{aa11}$ is Trp;
$X_{aa12}$ is Val;

A is

[Chem. 43]

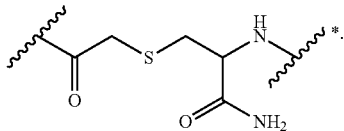

Advantageous Effects of Invention

The macrocyclic polypeptides or pharmacologically acceptable salts thereof of the present invention can bind to TSP1 to block the adhesion of cells such as vascular endothelial cells to TSP1. Therefore, the macrocyclic polypeptides or pharmacologically acceptable salts thereof of this invention are useful for the treatment or prophylaxis of diseases or symptoms induced by increased TSP1 expression. Also, the macrocyclic polypeptides or pharmacologically acceptable salts thereof of this invention are useful as angiogenesis promoters.

DESCRIPTION OF EMBODIMENTS (Definitions)

As referred to herein, natural amino acids mean unmodified amino acids commonly found in naturally occurring proteins, and more particularly mean alanine, arginine, asparagine, aspartic acid, cysteine, glutamic acid, glutamine, glycine, histidine, isoleucine, leucine, lysine, methionine, phenylalanine, proline, serine, threonine, tryptophane, tyrosine, and valine. Herein, the natural amino acids may be indicated by three-letter codes or one-letter codes (i.e., alanine: Ala or A; arginine: Arg or R; asparagine: Asn or N; aspartic acid: Asp or D; cysteine: Cys or C; glutamic acid: Glu or E; glutamine: Gin or Q; glycine: Gly or G; histidine: His or H; isoleucine: Ile or I; leucine: Leu or L; lysine: Lys or K; methionine: Met or M; phenylalanine: Phe or F; proline: Pro or P; serine: Ser or S; threonine: Thr or T; tryptophane: Trp or W; tyrosine: Tyr or Y; valine: Val or V).

As referred to herein, non-natural amino acids mean other amino acids than the natural amino acids, and also include modified versions of natural amino acids. The abbreviations for the non-natural amino acids referred to herein are listed below.

[Chem. 44]

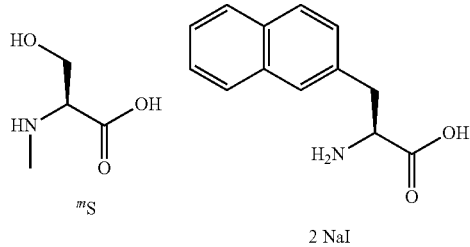

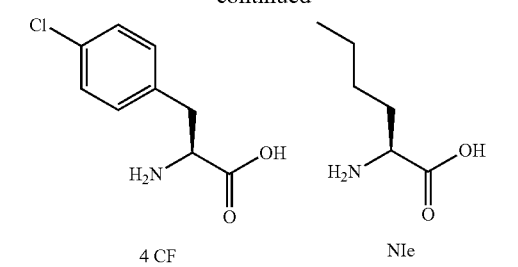
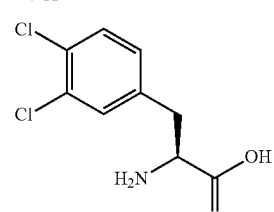
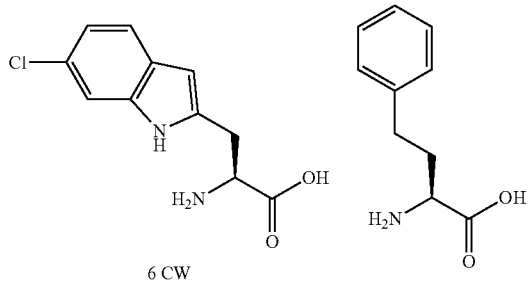
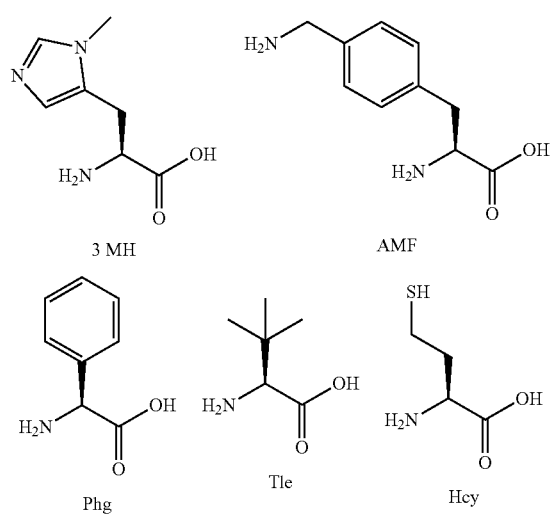
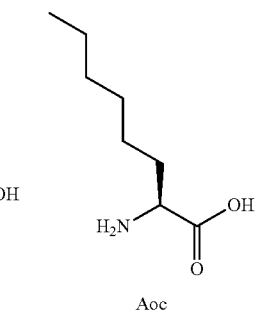
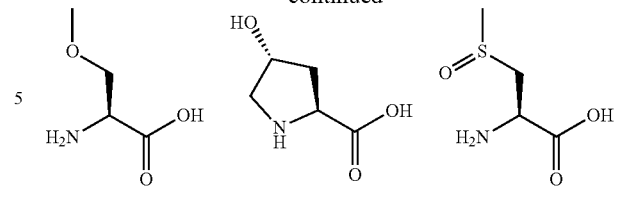
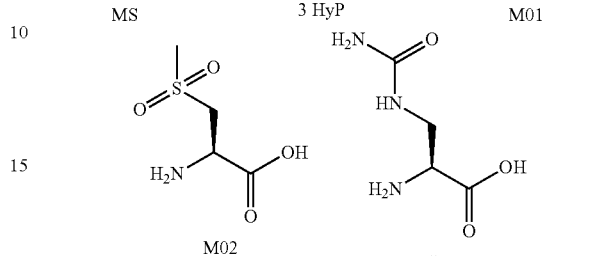
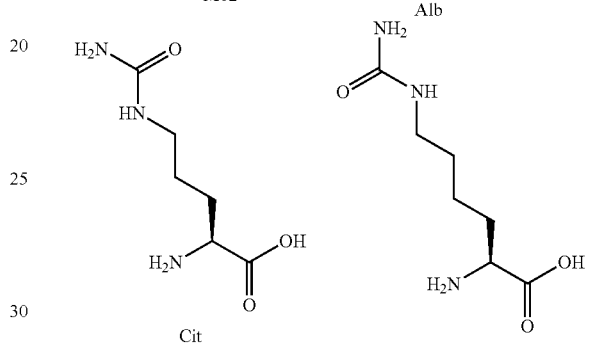
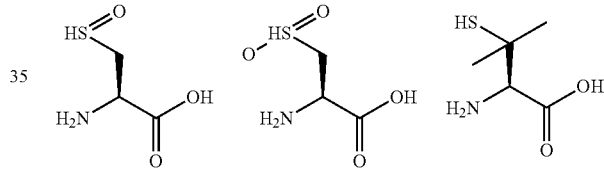
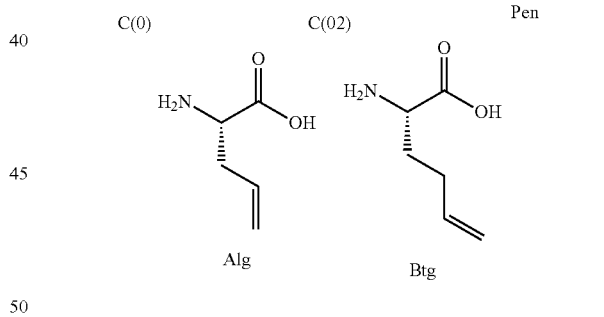
When the term "amino acid(s)" is used herein to describe a constitutional amino acid(s) of a polypeptide, this term refers to an amino acid residue(s). Unless otherwise specified, the amino acids as referred to herein are L-amino acids.
As referred to herein, the aliphatic amino acid is an amino acid represented by formula (IIa):
[Chem. 45]
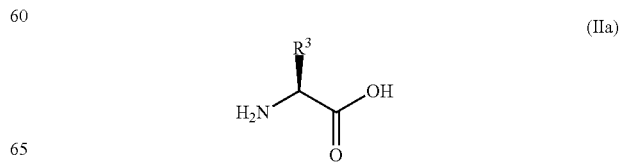
(IIa)

(wherein $R^3$ is $C_{1-6}$ alkyl, $C_{2-6}$ alkenyl or $C_{3-6}$ cycloalkyl).

Examples of natural aliphatic amino acids include Ala, Val, Leu, and Ile. Examples of non-natural aliphatic amino acids include, but are not limited to, Nle, Tle, Ahp, Aoc, Alg, and Btg.

As referred to herein, the aromatic amino acid is an amino acid represented by formula (IIb)

[Chem.46]

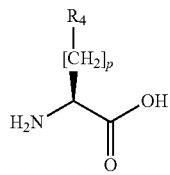

(IIb)

(wherein $R^4$ is an aromatic group selected from phenyl, thienyl, naphtyl, indolyl, benzofuranyl, and benzothienyl, wherein the aromatic group may be substituted with one or more substituents independently selected from the group consisting of $C_{1-3}$ alkyl, halogen atoms, hydroxy, and $C_{1-3}$ alkoxy; and p is an integer of 0 to 3).

Examples of natural aromatic amino acids include Phe, Tyr, and Trp. Examples of non-natural aromatic amino acids include, but are not limited to, 2Nal, 4CF, DCF, 6CW, HF, and Phg.

As referred to herein, the basic amino acid is an amino acid represented by formula (IIc)

[Chem. 47]

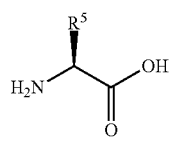

(IIc)

[wherein $R^5$ is a group represented by
the formula —$(CH_2)_{qa}NH_2$ (wherein qa is an integer of 1 to 6),
the formula

[Chem. 48]

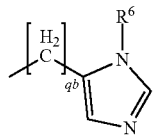

(wherein IV is a hydrogen atom or $C_{1-3}$ alkyl, and qb is an integer of 1 to 6),
the formula —$(CH_2)_{qc}NHC(=NH)NH_2$ (wherein qc is an integer of 1 to 6), or
the formula Chem. 49]

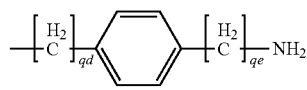

(wherein qd and qe are each independently an integer of 1 to 3)].

Examples of natural basic amino acids include Lys, His, and Arg. Examples of non-natural basic amino acids include, but are not limited to, 3MH, and AMF.

As referred to herein, the neutral amino acid is an amino acid represented by formula (IId)

[Chem. 50]

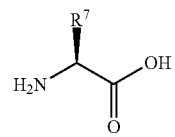

(IId)

[wherein $R^7$ is a group represented by the formula —$(CH_2)_m NHCONH_2$ (wherein ra is an integer of 1 to 6 (e.g., 1, 2, 3, 4, 5, or 6)), or the formula —$(CH_2)_{rb}SH$ (wherein rb is an integer of 1 to 3 (e.g., 1, 2, or 3))], Gly, Met, MO1, MO2, Fro, 3HyP, Asn, Gln, Ser, $^m$S, MS, Thr, C(O), C(O2), or Pen.

Examples of natural neutral amino acids include Gly, Ser, Thr, Cys, Met, Pro, Asn, and Gln. Examples of non-natural neutral amino acid include, but are not limited to, MO1, MO2, 3HyP, $^m$S, MS, Alb, Cit, Hct, Hcy, C(O), C(O2), and Pen.

As referred to herein, the acidic amino acid is an amino acid represented by formula (IIe)

[Chem. 51]

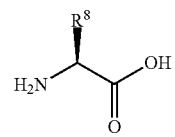

(IIe)

[wherein $R^8$ is a group represented by the formula —$(CH_2)_s COOH$ (wherein s is an integer of 1 to 6)].

Examples of natural acidic amino acids include Asp and Glu.

As referred to herein, $C_{1-3}$ alkyl refers to a straight or branched chain alkyl having 1 to 3 carbon atoms, such as methyl, ethyl, 1-propyl, or 2-propyl.

As referred to herein, $C_{1-6}$ alkyl refers to a straight or branched chain alkyl having 1 to 6 carbon atoms, such as methyl, ethyl, 1-propyl, 2-propyl, 1-butyl, 2-butyl, 2-methyl-1-propyl, 2-methyl-2-propyl, 1-pentyl, 2-pentyl, 3-pentyl, 2-methyl-2-butyl, 3-methyl-2-butyl, 1-hexyl, 2-hexyl, 3-hexyl, 2-methyl-1-pentyl, 3-methyl-1-pentyl, 2-ethyl-1-butyl, 2,2-dimethyl-1-butyl, or 2,3-dimethyl-1-butyl.

As referred to herein, $C_{2-6}$ alkenyl refers to a straight or branched chain alkenyl having 2 to 6 carbon atoms and containing one or more double bonds, such as vinyl, 1-propenyl, 2-propenyl(allyl), 1-butenyl, 2-butenyl, 3-butenyl, 1-methyl-2-propenyl, 2-methyl-2-propenyl, 1-pentenyl, 2-pentenyl, 3-pentenyl, 4-pentenyl, 1-methyl-2-butenyl, 2-methyl-2-butenyl, 1-hexenyl, 2-hexenyl, 3-hexenyl, 4-hexenyl, 5-hexenyl, or 3-methyl-2-pentenyl, with vinyl, 2-propenyl(allyl), 3-butenyl, 4-pentenyl, or 5-hexenyl being preferred.

As referred to herein, $C_{3-6}$ cycloalkyl refers to a cyclic alkyl group having 3 to 6 carbon atoms, such as cyclopropyl group, cyclobutyl group, cyclopentyl group, or cyclohexyl group.

As referred to herein, the halogen atoms are F, Cl, Br, or I.

As referred to herein, $C_{1-3}$ alkoxy refers to a hydroxyl group substituted with one $C_{1-3}$ alkyl group as defined above, such as methoxy, ethoxy, 1-propoxy, or 2-propoxy.

As referred to herein, the TSP1 inhibitory activity refers to the activity to inhibit one or more effects of TSP1, including angiostatic effect. The TSP1 inhibitory activity is measured by a cell adhesion inhibition assay using human TSP1 and vascular endothelial cells as described hereinbelow in the Examples section. In this assay, when the 50% inhibitory concentration ($IC_5O$) of a test substance is 200 nM or less, the test substance is determined to have TSP1 inhibitory activity.

(Macrocyclic Polypeptide(s) of the Present Invention)

The present invention relates to novel macrocyclic polypeptides having TSP inhibitory activity.

In one mode, the compound of the present invention is a macrocyclic polypeptide represented by formula (I)

[Chem. 52]

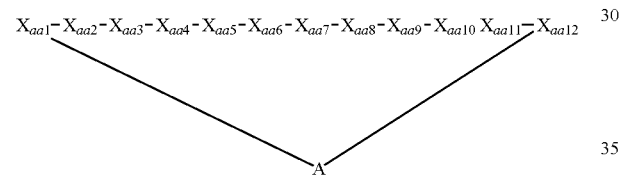

(hereinafter referred to as "the macrocyclic polypeptide of the present(this) invention"). The macrocyclic polypeptide of this invention has formed therein a macrocyclic structure in which the amino acids $X_{aa1}$ to $X_{aa12}$, or if $X_{aa1}$ is absent, the amino acids $X_{aa2}$ to $X_{aa12}$, are joined together by amide bonds to form a polypeptide chain, and the N-terminal amino acid ($X_{aa1}$ or $X_{aa2}$) and the C-terminal amino acid ($X_{aa12}$) of the polypeptide chain are joined together via a linking group A.

In formula (I), A is selected from the following linking groups $A_1$ to $A_6$ having an amino acid structure:

[Chem. 53]

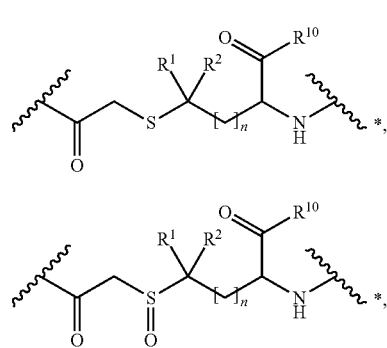

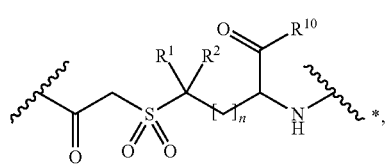

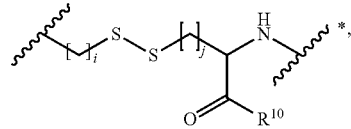

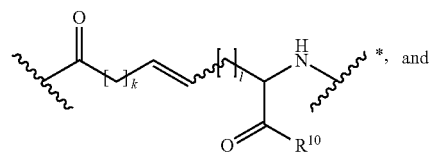

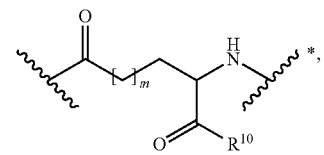

As found in either terminus of A,

[Chem. 54]

represents a point of attachment to the N-terminal amino group of $X_{aa1}$, or in the absence of $X_{aa1}$, represents a point of attachment to the N-terminal amino group of $X_{aa2}$,

[Chem. 55]

represents a point of attachment to the C-terminal carbonyl group of $X_{aa12}$, and

[Chem. 56]

represents a point of attachment to a carbon of $X_{aa1}$, or in the absence of $X_{aa1}$, represents a point of attachment to a carbon of $X_{aa2}$. The asymmetric centers in the amino acid structures contained in the aforementioned linking groups may have the R- or S-configuration.

In one mode, A is

[Chem. 57]

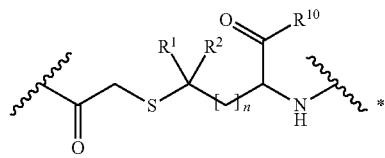

(hereinafter referred to as "$A_1$"). In the linking group $A_1$, n is an integer of 0 to 3 (e.g., 0, 1, 2, or 3), $R^1$ and $R^2$ are each independently a hydrogen atom or $C_{1-3}$ alkyl, and $R^{10}$ is amino or hydroxy. $C_{1-3}$ alkyl is preferably methyl.

A preferred mode of $A_1$ is a linking group of the formula:

[Chem. 58]

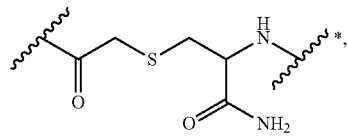

wherein $R^1$ and $R^2$ are each a hydrogen atom, $R^{10}$ is amino, and n is 0 (hereinafter referred to as "$A_{1a}$"). $A_{1a}$ can be obtained by, for example, allowing the —SH group of Cys (provided that the carboxy group is converted to amide) which is amide-bonded to the C-terminus of $X_{aa12}$ to react with —COCH$_2$X (wherein X is a leaving group such as Cl) which is bonded to the N-terminal amino group of $X_{aa1}$ or $X_{aa2}$. In such a linking group, the Cys may be an L-amino acid or a D-amino acid. In particular, that version of the linking group Ata, where the Cys (provided that the carboxy group is converted to amide) which is amide-bonded to the C-terminus of $X_{aa12}$ is an L-amino acid, is referred to as "$A_{1a1}$".

Another preferred mode of $A_1$ is a linking group of the formula:

[Chem. 59]

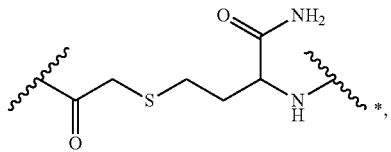

wherein $R^1$ and $R^2$ are each a hydrogen atom, $R^{10}$ is amino, and n is 1 (hereinafter referred to as "$A_{1b}$"). $A_{1b}$ can be obtained by, for example, allowing the —SH group of Hcy (provided that the carboxy group is converted to amide) which is amide-bonded to the C-terminus of $X_{aa12}$ to react with —COCH$_2$X (wherein X is a leaving group such as Cl) which is bonded to the N-terminal amino group of $X_{aa1}$ or $X_{aa2}$. In such a linking group, the Hcy may be an L-amino acid or a D-amino acid. In particular, that version of the linking group $A_{1b}$, where the Hcy (provided that the carboxy group is converted to amide) which is amide-bonded to the C-terminus of $X_{aa12}$ is an L-amino acid, is referred to as "$A_{1b1}$".

Another preferred mode of the linking group $A_1$ is a linking group of the formula:

[Chem. 60]

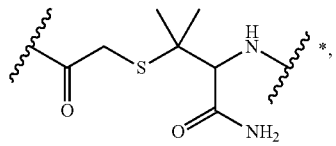

wherein $R^1$ and $R^2$ are each methyl, $R_{10}$ is amino, and n is 0 (hereinafter referred to as "$A_{1c}$"). $A_{1c}$ can be obtained by, for example, allowing the —SH group of Pen (provided that the carboxy group is converted to amide) which is amide-bonded to the C-terminus of $X_{aa12}$ to react with —COCH$_2$X (wherein X is a leaving group such as Cl) which is bonded to the N-terminal amino group of $X_{aa1}$ or $X_{aa2}$. In such a linking group, the Pen may be an L-amino acid or a D-amino acid. In particular, that version of the linking group $A_{1c}$, where the Pen (provided that the carboxy group is converted to amide) which is amide-bonded to the C-terminus of $X_{aa12}$ is an L-amino acid, is referred to as "$A_{1c1}$".

In another mode, the linking group A is

[Chem. 61]

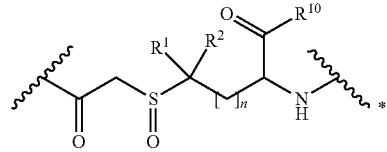

(hereinafter referred to as "$A_2$"). In the linking group $A_2$, n is an integer of 0 to 3 (e.g., 0, 1, 2, or 3), $R^1$ and $R^2$ are each independently a hydrogen atom or $C_{1-3}$ alkyl, and $R^{10}$ is amino or hydroxy.

A preferred mode of $A_2$ is that version of said linking group, where $R^1$ and $R^2$ are each a hydrogen atom, $R^{10}$ is amino, and n is 0 (hereinafter referred to as "$A_{2a}$"). $A_{2a}$ can be obtained by, for example, oxidizing the sulfide group of the linking group $A_{1a}$ as shown above to sulfoxide. In particular, the linking group obtained by oxidizing the sulfide group of $A_{1a1}$ to sulfoxide is referred to as "$A_{2a1}$".

In another mode, A is

[Chem. 62]

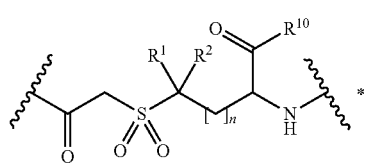

(hereinafter referred to as "$A_3$"). In the linking group $A_3$, n is an integer of 0 to 3 (e.g., 0, 1, 2, or 3), and $R^2$ are each independently a hydrogen atom or $C_{1-3}$ alkyl, and $R^{10}$ is amino or hydroxy.

A preferred mode of A3 is that version of said linking group, where $R^1$ and $R^2$ are each a hydrogen atom, $R^{10}$ is amino, and n is 0 (hereinafter referred to as "$A_{3a}$"). $A_{3a}$ can be obtained by, for example, oxidizing the sulfide group of the linking group $A_{1a}$ as shown above to sulfone. In particular, the linking group obtained by oxidizing the sulfide group of $A_{1a1}$ to sulfone is referred to as "$A_{3a1}$".

In another mode, A is

[Chem. 63]

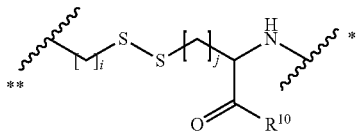

(hereinafter referred to as "$A_4$"). In the linking group $A_4$, i and j are each independently an integer of 1 to 3 (e.g., 1, 2, or 3), and $R^{10}$ is amino or hydroxy.

When A is $A_4$, $X_{aa1}$ or $X_{aa2}$ is a residue of an amino acid represented by

[Chem. 64]

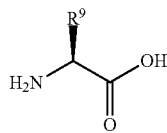

[wherein $R^9$ is a group represented by the formula —$(CH_2)_tSH$ (wherein t is an integer of 1 to 3 (e.g., 1, 2, or 3))].

In a preferred mode of A4, i and j are each 1, and $R^{10}$ is amino (hereinafter, this version of linking group is referred to as "$A_{4a}$"). $A_{4a}$ can be obtained by, for example, allowing the —SH group of Cys (provided that the carboxy group is converted to amide) which is amide-bonded to the C-terminus of $X_{aa12}$ to react with the —SH group of $X_{aa1}$ or $X_{aa2}$. In such a linking group, the Cys may be an L-amino acid or a D-amino acid. In particular, that version of the linking group $A_{4a}$, where the Cys (provided that the carboxy group is converted to amide) which is amide-bonded to the C-terminus of $X_{aa12}$ is an L-amino acid, is referred to as "$A_{4a1}$".

In another mode, A is

[Chem. 65]

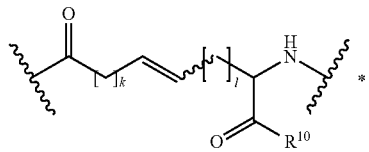

(hereinafter referred to as "$A_5$"). In the linking group $A_5$, k and l are each independently an integer of 0 to 3 (e.g., 0, 1, 2, or 3), and $R^{10}$ is amino or hydroxy. The linking group $A_5$ can be obtained by, for example, olefin metathesis of the amino acid (provided that the carboxy group may be converted to amide) which has the group —$(CH_2)_lCH=CH_2$ on its side chain and is amide-bonded to the C-terminus of $X_{aa12}$, and the group —$CO(CH_2)_kCH=CH_2$ which is boned to the N-terminal amino group of $X_{aa1}$ or $X_{aa2}$. In such a linking group, the amino acid which is amide-bonded to the C-terminus of $X_{aa12}$ may be an L-amino acid or a D-amino acid.

In another mode, A is

[Chem. 66]

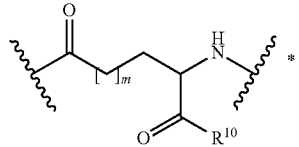

(hereinafter referred to as "$A_6$"). In the linking group $A_6$, m is an integer of 1 to 7 (e.g., 1, 2, 3, 4, 5, 6, or 7), and $R^{10}$ is amino or hydroxy. $A_6$ can be obtained by, for example, reducing the carbon-carbon double bond of $A_s$.

In formula (I), $X_{aa1}$ is a residue of an aliphatic amino acid, an aromatic amino acid, a basic amino acid, a neutral amino acid, or an acidic amino acid, or is absent. In a preferred mode, $X_{aa1}$ is Arg, Lys, His, Gly, Ala, Asn, Thr, Ser, Met, Leu, Ile, Val, Gln, Phe, Tyr, Trp, or Cys, or is absent, and more preferably is Arg, Lys, or Gly, or is absent.

In formula (I), $X_{aa2}$ is a residue of an aromatic amino acid or a neutral amino acid. In a preferred mode, $X_{aa2}$ is a residue of an aromatic amino acid, more preferably Phe, Tyr, Trp, 2Nal, 4CF, or DCF, even more preferably 2Nal.

In formula (I), $X_{aa3}$ is a residue of an aliphatic amino acid, an aromatic amino acid, or a basic amino acid. In a preferred mode, $X_{aa3}$ is Ile, Leu, Nle, Tle, Trp, 2Nal, 4CF, or Arg, more preferably Ile, or Arg.

In formula (I), $X_{aa4}$ is Ser, Thr, Ala, or $^mS$. In a preferred mode, $X_{aa4}$ is Ser.

In formula (I), $X_{aa5}$ is Gly or Ser. In a preferred mode, $X_{aa5}$ is Gly.

In formula (I), $X_{aa6}$ is a residue of a basic amino acid or a neutral amino acid. In a preferred mode, $X_{aa6}$ is Arg, Lys, His, Cit, Ser, or MO2, more preferably Arg, Lys, His, or Ser.

In formula (I), $X_{aa7}$ is a residue of a neutral amino acid or an acidic amino acid. In a preferred mode, $X_{aa7}$ is Asn or Asp.

In formula (I), $X_{aa8}$ is a residue of an aromatic amino acid. In a preferred mode, $X_{aa8}$ is Trp, 2Nal, or 6CW, more preferably Trp.

In formula (I), $X_{aa9}$ is a residue of an aliphatic amino acid, a neutral amino acid, or an aromatic amino acid. In a preferred mode, $X_{aa9}$ is Val, Nle, Ahp, or Met, more preferably Val, Nle, or Ahp.

In formula (I), $X_{aa10}$ is a residue of a basic amino acid, an aliphatic amino acid, an aromatic amino acid, or a neutral amino acid. In a preferred mode, $X_{aa10}$ is Arg, Lys, His, AMF, Phg, or Val, more preferably Arg, Lys, His, Phg, or Val.

In formula (I), $X_{aa11}$ is a residue of an aromatic amino acid. In a preferred mode, $X_{aa11}$ is Trp or 2Nal, more preferably Tip.

In formula (I), $X_{aa12}$ is a residue of an aliphatic amino acid, an aromatic amino acid, or a basic amino acid. In a preferred mode, $X_{aa12}$ is Val, Tle, or Phe, more preferably Val.

A preferred mode of the macrocyclic polypeptide of the present invention is a macrocyclic polypeptide represented by formula (I), wherein A is the linking group $A_{1a}$, $A_{1b}$, or $A_{1c}$;

$X_{aa1}$ is Arg, Lys, His, Gly, Ala, Asn, Thr, Ser, Met, Leu, Ile, Val, Gln, Phe, Tyr, Trp, or Cys, or is absent;

$X_{aa2}$ is Phe, Tyr, Trp, 2Nal, 4CF, or DCF;

$X_{aa3}$ is Ile, Leu, Nle, Tle, Trp, 2Nal, 4CF, or Arg;

$X_{aa4}$ is Ser;

$X_{aa5}$ is Gly;

$X_{aa6}$ is Arg, Lys, His, Ser, Cit, or MO2;

$X_{aa7}$ is Asn or Asp;

$X_{aa8}$ is Trp, 2Nal, or 6CW;

$X_{aa9}$ is Val, Nle, Ahp, or Met;

$X_{aa10}$ is Arg, Lys, His, AMF, Phg, or Val;

$X_{aa11}$ is Trp or 2Nal; and $X_{aa12}$ is Val, Tle, or Phe.

A more preferred mode of the macrocyclic polypeptide of the present invention is a macrocyclic polypeptide represented by formula (I), wherein A is the linking group $A_{1a}$;

$X_{aa1}$ is Arg, Lys, or Gly, or is absent;

$X_{aa2}$ is 2Nal;

$X_{aa3}$ is Ile, or Arg;

$X_{aa4}$ is Ser;

$X_{aa5}$ is Gly;

$X_{aa6}$ is Arg, Lys, His, or Ser;

$X_{aa7}$ is Asn or Asp;

$X_{aa8}$ is Trp;

$X_{aa9}$ is Val, Nle, or Ahp;

$X_{aa10}$ is Arg, Lys, His, Phg, or Val;

$X_{aa11}$ is Trp; and $X_{aa12}$ is Val.

A yet more preferred mode of the macrocyclic polypeptide of the present invention is a macrocyclic polypeptide selected from the groups of the compounds represented by the following formulas:

[Chem. 67]

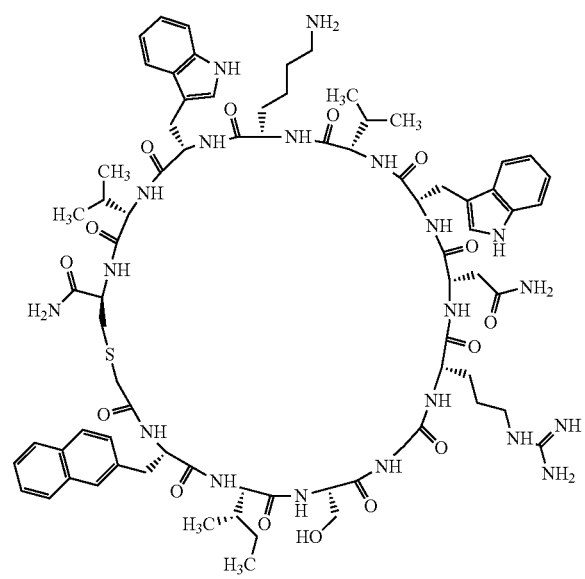

-continued

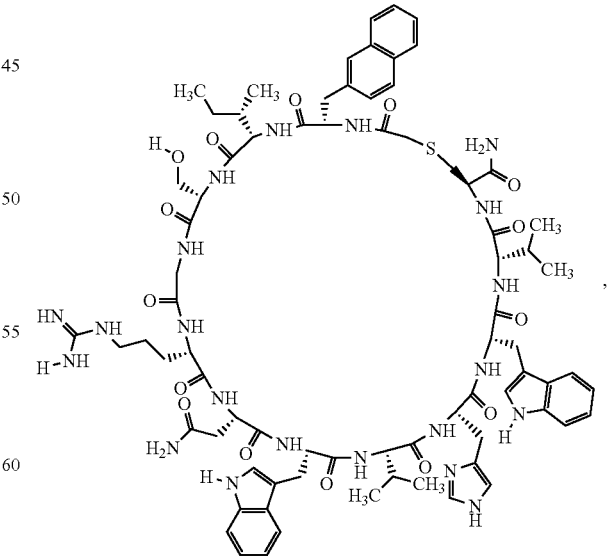

[Chem. 68]

35
-continued
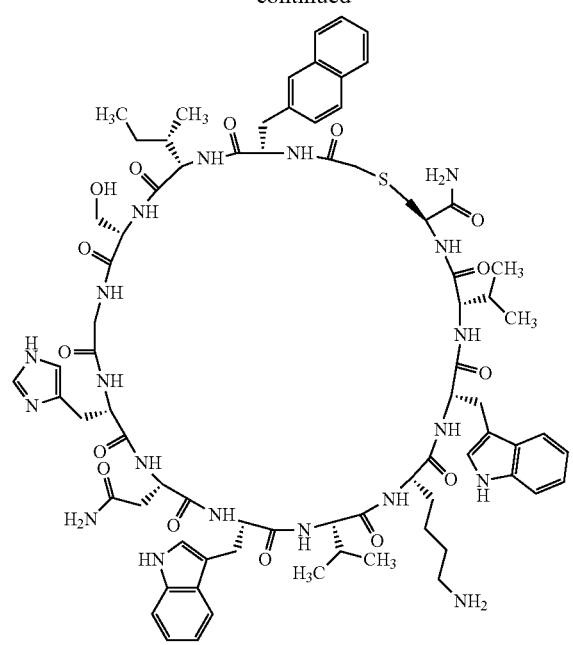
36
-continued
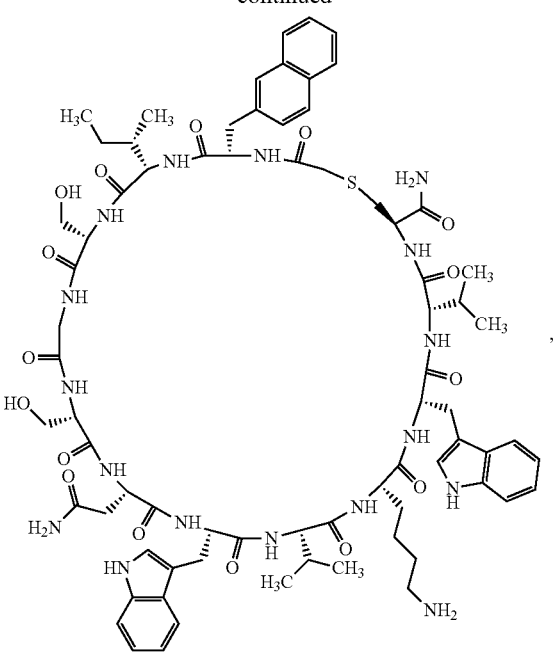
[Chem. 69]
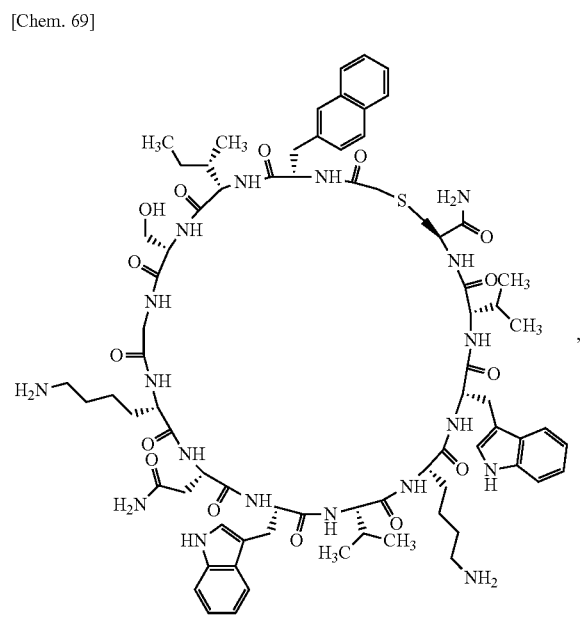
[Chem. 70]
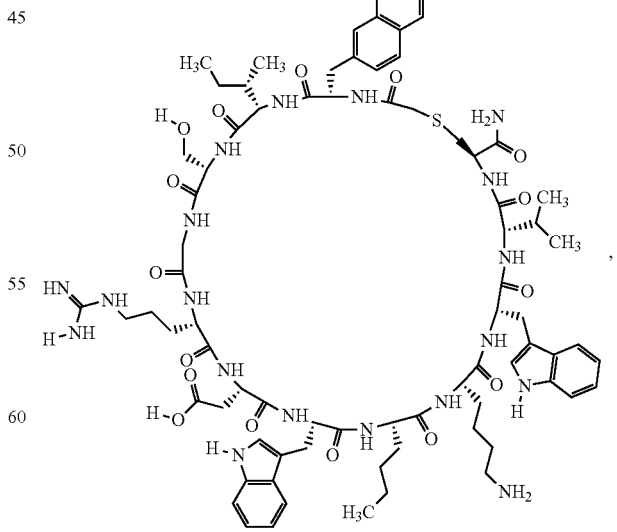

37
-continued
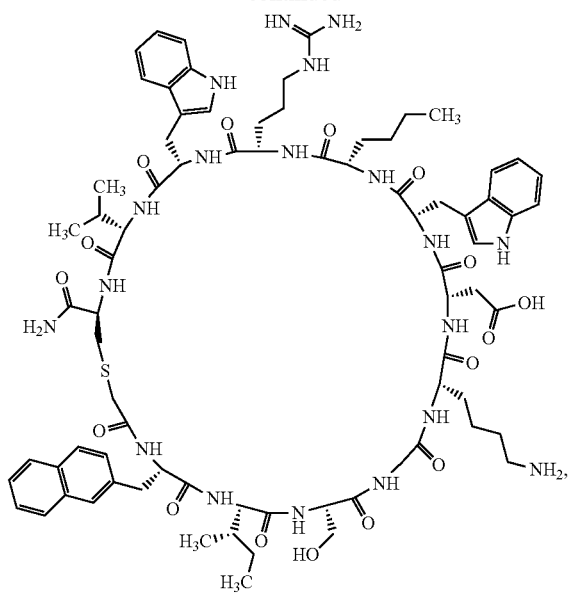
38
-continued
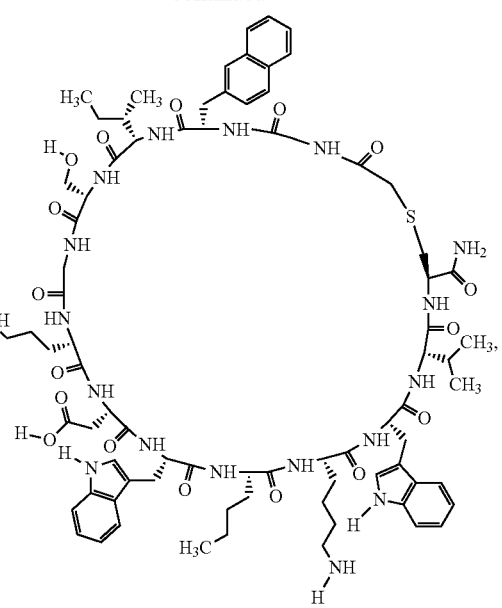
[Chem. 71]
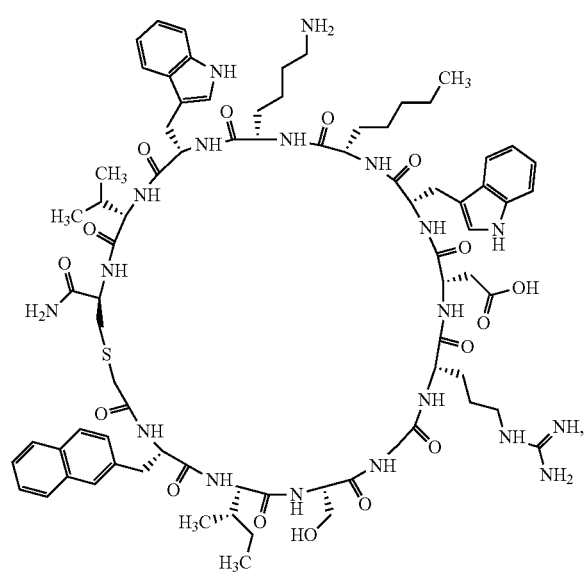
[Chem. 72]
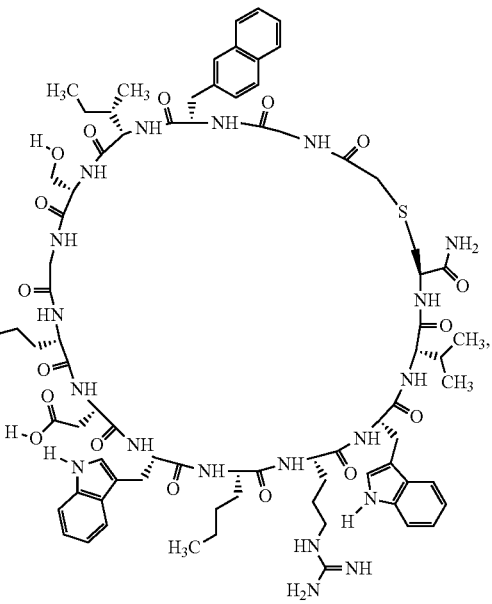

39
-continued
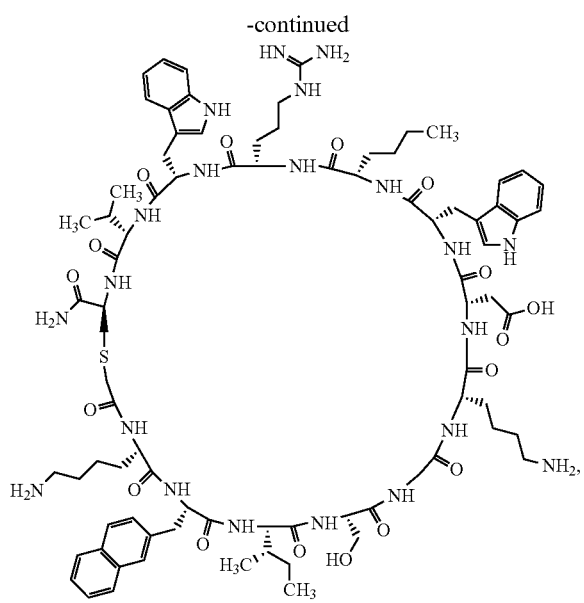
[Chem. 73]
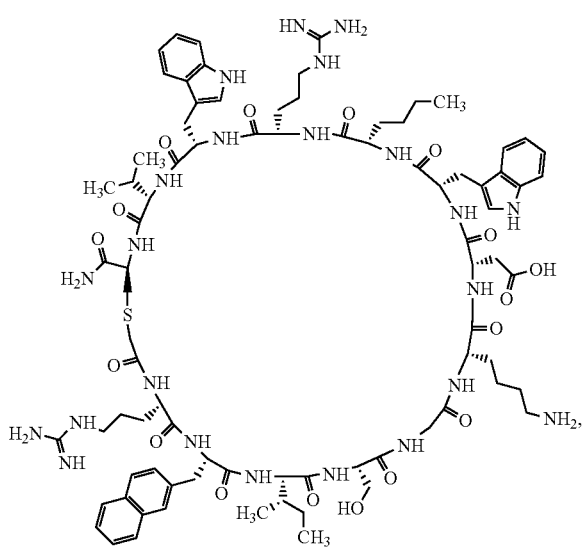
40
-continued
[Chem. 74]
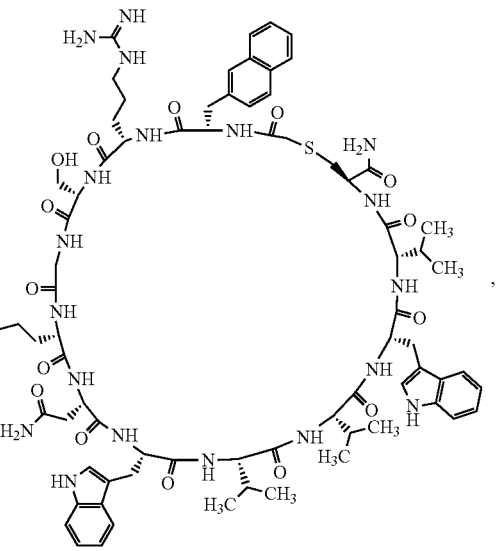
[Chem. 75]
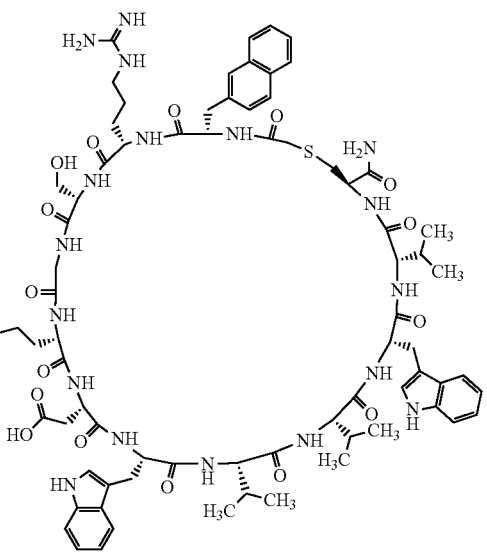

[Chem. 76]

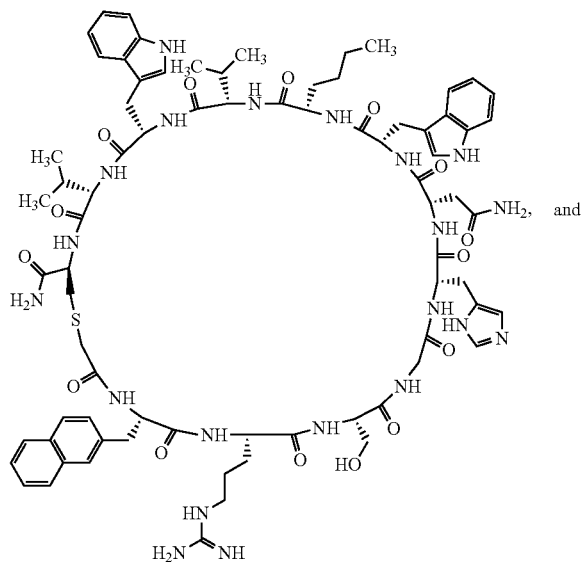

[Chem. 77]

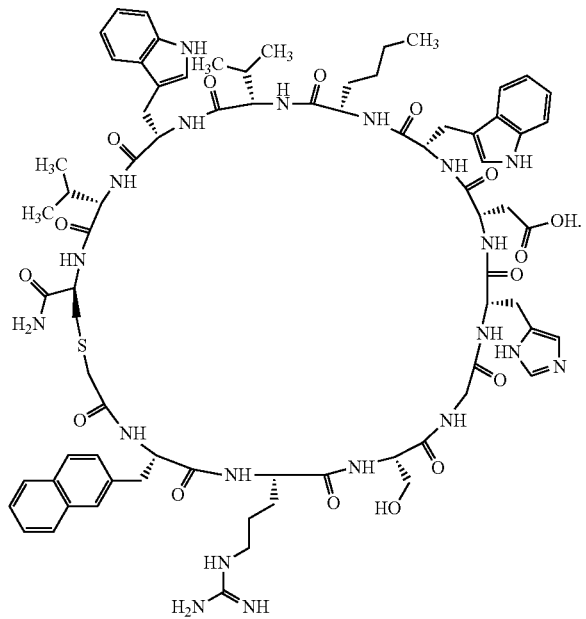

The polypeptides shown above are the compounds of Examples 24, 40, 41, 42, 43, 44, 45, 58, 60, 75, 76, 95, 96, and 98 to 101 as shown hereinbelow. In all of these polypeptides, A is the linking group $A_{1a1}$.

When the macrocyclic polypeptide of the present invention contains a basic group, the macrocyclic polypeptide can combine with an acid to form a salt thereof, and such a salt is included in this invention. Examples of such a salt include inorganic acid salt, organic acid salt, amino acid salt, and sulfonate. Examples of the inorganic acid salt include hydrochloride, hydrobromate, sulfate, nitrate, and phosphate. Example of the organic acid salt include acetate, oxalate, malonate, fumarate, maleate, phthalate, and trifluoroacetate. Examples of the amino acid salt include glutamate, and aspartate. Examples of the sulfonate include methanesulfonate, benzenesulfonate, p-toluenesulfonate, 2,4-dimethylbenzenesulfonate, 2,4,6-trimethylbenzenesulfonate, 4-ethylbenzenesulfonate, and naphthalenesulfonate. A preferred mode of the pharmacologically acceptable salt of the macrocyclic polypeptide of this invention is an acetate, a hydrochloride, or a trifluoroacetate, more preferably an acetate.

When the macrocyclic polypeptide of the present invention contains an acidic group, the macrocyclic polypeptide can combine with a base to form a salt thereof, and such a salt is also included in this invention. Examples of such a salt include metal salt, inorganic amine salt, organic amine salt, and amino acid salt. Examples of the metal salt include: alkali metal salts such as sodium salt, potassium salt, and lithium salt; alkaline-earth metal salts such as calcium salt and magnesium salt; as well as aluminum salt, iron salt, zinc salt, copper salt, nickel salt, and cobalt salt. Examples of the inorganic amine salt include ammonium salt. Examples of the organic amine salt include morpholine salt, glucosamine salt, ethylenediamine salt, guanidine salt, diethylamine salt, triethylamine salt, dicyclohexylamine salt, diethanolamine salt, piperazine salt, and tetramethylammonium salt. Examples of the amino acid salt include lysine salt, and arginine salt.

The macrocyclic polypeptide or pharmacologically acceptable salt thereof of the present invention may be used in a crystalline form. Such a crystal may be formed exclusively of the macrocyclic polypeptide or pharmacologically acceptable salt thereof of this invention, or the macrocyclic polypeptide or pharmacologically acceptable salt thereof may be formed as a cocrystal or a solvate (e.g., hydrate). One type of the macrocyclic polypeptide or the pharmacologically acceptable salt thereof of this invention may be used alone, or two or more types thereof may be used in combination as appropriate.

The macrocyclic polypeptide or pharmacologically acceptable salt thereof of the present invention can form an isotopic compound in which one or more constitutional atom is substituted with an isotopic atom in a non-natural proportion. The isotopic atom may be radioactive or non-radioactive, and examples thereof include deuterium ($^2$H; D), tritium ($^3$H; T), carbon-14 ($^{14}$C), and iodine-125 ($^{125}$I). Compounds labeled with a radioactive isotopic atom can be used as therapeutic or prophylactic agents for various diseases, research reagents (e.g., assay reagent), diagnostic agents (e.g., image diagnostic agent), or the like. This invention also includes such a radioactive or non-radioactive isotopic compound.

The macrocyclic polypeptide or pharmacologically acceptable salt thereof of the present invention can be prepared by a method known in the art, such as chemical synthesis or cell-free translation system. For example, chemical synthesis of the macrocyclic polypeptide of this invention can be carried out according to a common solid-phase synthesis method using a 9-fluorenylmethoxycarbonyl group (Fmoc group) as an α-amino group-protecting group. Solid-phase synthesis can be performed using a commercially available automatic synthesizer (e.g., Syro II (produced by Biotage Japan), Liberty Blue (produced by CEM)).

To cite some examples, the macrocyclic polypeptide of the present invention containing the linking group $A_1$ can be obtained by following, for example, the procedure described below.

With the use of an automatic peptide synthesizer, amino acids protected with an amino group-protecting group (e.g., Fmoc group) are coupled to a solid support (e.g., Rink Amide Resin AM (produced by Novaviochem), 2-chlorotrityl chloride resin (produced by Novaviochem)) in a stepwise manner starting with the C-terminal amino acid (the C-terminal amino acid is a thiol-containing amino acid). Deprotection of amino groups is performed by a method known to skilled artisans (e.g., using 20% piperidine/1-methyl-2-pyrrolidinone to remove Fmoc groups). After the N-terminal amino acid is coupled and the amino group of this amino acid is deprotected, a linking group-forming group (e.g., chloromethylcarbonyl group) is introduced (e.g., to allow chloroacetic acid to react with the N-terminal amino group) to form a macrocyclic peptide. Then, the resulting peptide is cleaved from the peptide resin by a conventional procedure (e.g., using trifluoroacetic acid/ethanedithiol/triisopropylsilane/water to cleave from Rink Amide Resin AM). After a crude peptide is recovered by ether precipitation, the peptide of interest is purified by a conventional procedure (e.g., reverse-phase high-performance liquid chromatography). The resulting peptide of interest can be converted to a desired salt by a conventional procedure.

The macrocyclic polypeptide of the present invention containing the linking group A4 can be prepared by, for example, coupling an —SH-containing amino acid serving as an N-terminal amino acid at the end of the aforementioned procedure, and thereby forming a macrocyclic peptide without the need to introduce a further linking group-forming group.

The macrocyclic polypeptide or pharmacologically acceptable salt thereof of the present invention containing the linking group A2 or A3 can be obtained by, for example, oxidizing the macrocyclic polypeptide or pharmacologically acceptable salt thereof of this invention containing the linking group $A_1$ with an oxidizing agent (e.g., m-chloroperoxybenzoic acid, hydrogen peroxide, or dimethyldioxirane).

For example, the macrocyclic polypeptide of the present invention containing the linking group $A_5$ or $A_6$ can be obtained by following the procedure described below.

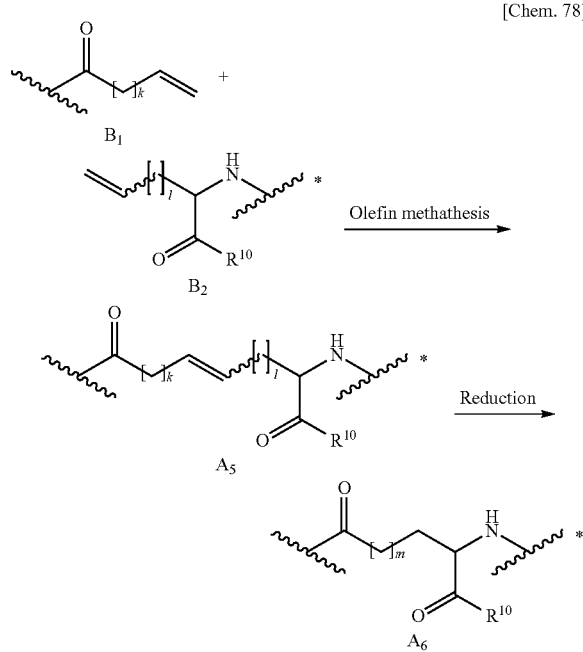

[Chem. 78]

A polypeptide containing the terminal groups $B_1$ and $B_2$ can be prepared using an automatic peptide synthesizer by taking the steps of coupling amino acids protected with an amino group-protecting group (e.g., Fmoc group) to a solid support in a stepwise manner starting with the C-terminal amino acid (the C-terminal amino acid is an olefin-containing amino acid), deprotecting the amino group of the N-terminal amino acid, and introducing a linking group-forming group (e.g., 2-propenyl group).

After the polypeptide containing the terminal groups $B_1$ and $B_2$ is prepared, said polypeptide is subjected to olefin metathesis reaction in the presence of an appropriate catalyst (e.g., 2nd generation Grubbs' catalyst), whereby the macrocyclic polypeptide containing the linking group $A_5$ can be prepared. When the macrocyclic polypeptide containing the linking group $A_5$ is subjected to reduction reaction under appropriate conditions (e.g., in the presence of hydrogen and a Wilkinson's catalyst), the macrocyclic polypeptide containing the linking group $A_6$ can be obtained.

The macrocyclic polypeptides or pharmacologically acceptable salts thereof of the present invention have TSP1 inhibitory activity and the ability to block the adhesion of vascular endothelial cells to TSP1, and are thus useful as angiogenesis inhibitors.

(Pharmaceutical Composition)

The present invention further provides a pharmaceutical composition comprising, as an active component, the macrocyclic polypeptide or pharmacologically acceptable salt thereof of this invention. The pharmaceutical composition of this invention has excellent TSP1 inhibitory activity, and is useful for the treatment or prophylaxis of diseases or symptoms induced by increased TSP1 expression (e.g., various diseases, including diseases caused by angiogenesis inhibition, diseases caused by increased thrombogenesis, inflammatory diseases, diseases caused by deterioration of renal cellular function, diseases caused by suppression of vasorelaxation, ischemic diseases, and cancerous diseases; and various symptoms, including vaso-occlusive crisis associated with sickle cell disease, angiogenesis inhibition, tissue necrosis, insulin resistance, and common wounds). Examples of the diseases caused by angiogenesis inhibition include critical limb ischemia, and peripheral vascular disorder. Examples of the diseases caused by increased thrombogenesis include myocardial infarction, and peripheral vascular disorder (PAD). Examples of the inflammatory diseases include obesity-induced inflammation, and inflammation during aortic aneurysm development. Examples of the diseases caused by deterioration of renal cellular function include diabetic nephropathy, IgA nephropathy, chronic renal failure, and acute renal failure. Examples of the diseases caused by suppression of vasorelaxation include kidney injury, and ischemia-reperfusion injury. Examples of the ischemic diseases include myocardial infarction, and angina. Examples of the cancerous diseases include squamous cancer, breast cancer, and pancreatic cancer. TSP1 is reported to promote the progress of squamous cancer, breast cancer, and pancreatic cancer (refer to e.g., NPL 21, p. 39 left col. line 14 from bottom to right cal. line 3, and Table 4). In a preferred mode, the pharmaceutical composition of this invention is useful for the treatment or prophylaxis of critical limb ischemia or peripheral arterial disease, and is, for example, useful for the acceleration of wound healing in critical limb ischemia patients and for the improvement of prognosis after endovascular treatment for critical limb ischemia.

It is known that the expression of TSP1 increases in the lower-limb skeletal muscles of critical limb ischemia patients. Although not wishing to be bound by any theory, it is believed that the pharmaceutical composition of the present invention blocks the adhesion of vascular endothelial cells to TSP1, and thereby can promote angiogenesis inhibited by TSP1. By virtue of this function, the pharmaceutical composition of this invention can accelerate wound healing in critical limb ischemia patients and improve prognosis (e.g., prevent restenosis) when combined with endovascular treatment with a catheter or the like.

In the present invention, the treatment or prophylaxis of diseases or symptoms include prevention of the onset of diseases or suppression or inhibition of the exacerbation or progress of such diseases, alleviation of one or more symptoms found in individuals suffering from diseases or suppression of the exacerbation or progress of such symptoms, and treatment or prophylaxis of secondary diseases.

The pharmaceutical composition of the present invention can be formulated into a pharmaceutical preparation by mixing the macrocyclic polypeptide or pharmacologically acceptable salt thereof of this invention with any appropriate pharmacologically acceptable additives. For example, the pharmaceutical composition of this invention can be administered as oral preparations such as tablets, capsules and granules, or as parenteral preparations such as injectables and percutaneous absorption agents.

Such pharmaceutical preparations are prepared by a well-known method using different additives, including excipient, binder, disintegrant, lubricant, emulsifier, stabilizer, diluent, injectable solvent, solubilizer, suspending agent, isotonizing agent, buffer, analgesic, antiseptic, and antioxidant.

Examples of the excipient include organic excipients or inorganic excipients. Examples of the organic excipients include sugar derivatives such as lactose and saccharose; starch derivatives such cornstarch and potato starch; cellulose derivatives such as crystalline cellulose; and gum Arabic. Examples of the inorganic excipients include sulfates such as calcium sulfate.

Examples of the binder include such excipients as mentioned above; gelatin; polyvinylpyrrolidone; and polyethylene glycol.

Examples of the disintegrant include such excipients as mentioned above; chemically modified starch or cellulose derivatives such as sodium croscarmellose and sodium carboxymethyl starch; and crosslinked polyvinylpyrrolidone.

Examples of the lubricant include talc; stearic acid; colloidal silica; waxes such as beeswax and spermaceti wax; sulfates such as sodium sulfate; lauryl sulfates such as sodium lauryl sulfate; and such starch derivatives as mentioned above as excipients.

Examples of the emulsifier include colloidal clays such as bentonite and veegum; anionic detergents such as sodium lauryl sulfate; cationic detergents such as benzalkonium chloride; and nonionic detergents such as polyoxyethylene alkyl ether.

Examples of the stabilizer include p-hydroxybenzoic esters such as methylparaben and propylparaben; alcohols such as chlorobutanol; and phenolic compounds such as phenol and cresol.

Examples of the diluent include water, ethanol, and propylene glycol.

Examples of the injectable solvent include water, ethanol, and glycerin.

Examples of the solubilizer include polyethylene glycol, propylene glycol, D-mannitol, benzyl benzoate, ethanol, trisaminomethane, cholesterol, triethanolamine, sodium carbonate, and sodium citrate.

Examples of the suspending agent include various detergents such as stearyl triethanolamine, sodium lauryl sulfate, lauryl aminopropionic acid, lecithin, benzalkonium chloride, benzethonium chloride, and glyceryl monostearate; and hydrophilic polymers such as polyvinyl alcohol, polyvinylpyrrolidone, carboxymethylcellulose sodium, methylcellulose, hydroxymethylcellulose, hydroxyethylcellulose, and hydroxypropylcellulose.

Examples of the isotonizing agent include sodium chloride, glycerin, and D-mannitol.

Examples of the buffer include phosphate, acetate, carbonate, citrate and other buffers.

Examples of the analgesic include benzyl alcohol.

Examples of the antiseptic include p-hydroxybenzoic esters, chlorobutanol, benzyl alcohol, phenethyl alcohol, dehydroacetic acid, and sorbic acid.

Examples of the antioxidant include sulfites and ascorbic acid.

The subject to be administered the pharmaceutical composition of the present invention is, for example, a mammalian animal, preferably a human.

The administration route of the pharmaceutical composition of the present invention can be either of oral and parenteral routes, and a suitable route can be selected depending on the disease to be treated. Further, the administration route of said inventive pharmaceutical composition can be either of systemic and topical administrations. Examples of parenteral administrations include intravenous administration, intraarterial administration, intramuscular administration, intracutaneous administration, subcutaneous administration, intraperitoneal administration, percutaneous administration, intraosseous administration, and intraarticular administration. A preferred mode of the administration route of said inventive pharmaceutical composition is intravenous administration, subcutaneous administration, or percutaneous administration.

The macrocyclic polypeptide or pharmacologically acceptable salt thereof of the present invention is administered to a subject in a therapeutically or prophylactically effective amount. The term "therapeutically or prophylactically effective amount" means an amount required for an active agent to exhibit a therapeutic or prophylactic effect in consideration of particular disease, dosage form, and administration route, and is determined, as appropriate, depending on the species of a subject, type of a disease, symptom, sex, age, pre-existing condition, and other elements.

The dose of the macrocyclic polypeptide or pharmacologically acceptable salt thereof of the present invention is determined, as appropriate, depending on the species of a subject, type of a disease, symptom, sex, age, pre-existing condition, and other elements. Human adults can take medication with said inventive macrocyclic polypeptide or pharmacologically acceptable salt thereof in a dose of generally 0.1 to 1000 mg/kg, preferably 0.1 to 10 mg/kg, once every 1 to 7 days, or two or three or more times daily.

The pharmaceutical composition of the present invention may be combined with at least one known therapeutic agent or therapy. For example, during critical limb ischemia treatment, the pharmaceutical composition of this invention can be administered before, after or simultaneously with endovascular treatment with a catheter or the like.

The macrocyclic polypeptide or pharmacologically acceptable salt thereof of this invention can be delivered by means of a drug-eluting stent (DES). The drug-eluting stent refers to a stent that has an active drug carried on its surface so that it can gradually elute the active drug after being placed into a blood vessel.

Furthermore, the present invention is directed to a method for the treatment or prophylaxis of a disease or symptom, the method comprising administering a therapeutically or prophylactically effective amount of the macrocyclic polypeptide or pharmacologically acceptable salt thereof of this invention to a subject in need thereof.

As referred to in the present invention, the term "therapeutically or prophylactically effective amount" means an amount required for an active agent to exhibit a therapeutic or prophylactic effect in consideration of particular disease or symptom, dosage form, and administration route, and is determined, as appropriate, depending on the species of a subject, type of a disease or symptom, symptom, sex, age, pre-existing condition, and other elements.

As referred to in the present invention, the "subject" is, for example, a mammalian animal, preferably a human.

As referred to in the present invention, the term "administration" includes oral and parenteral administrations, and can be either of systemic and topical administrations. Examples of parenteral administrations include intravenous administration, intraarterial administration, intramuscular administration, intracutaneous administration, subcutaneous administration, intraperitoneal administration, percutaneous administration, intraosseous administration, and intraarticular administration. A preferred mode of the "administration" as referred to in this invention is intravenous administration, subcutaneous administration, or percutaneous administration.

Examples of the "disease(s) or symptom(s)" as referred to in the present invention include diseases or symptoms induced by increased TSP1 expression. According to this invention, the treatment or prophylaxis of critical limb ischemia or peripheral arterial disease can be achieved.

Hereunder, the present invention will be described in more detail with reference to working and test examples, but the scope of this invention is not limited to these examples.

EXAMPLES

Examples 1 to 104

The following shows the structural formulas of the macrocyclic polypeptides of Examples 1 to 104.

[Chem. 79]

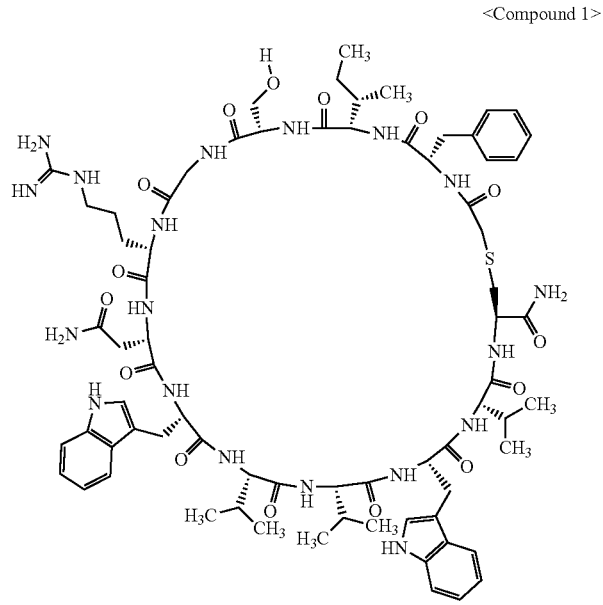

<Compound 1>

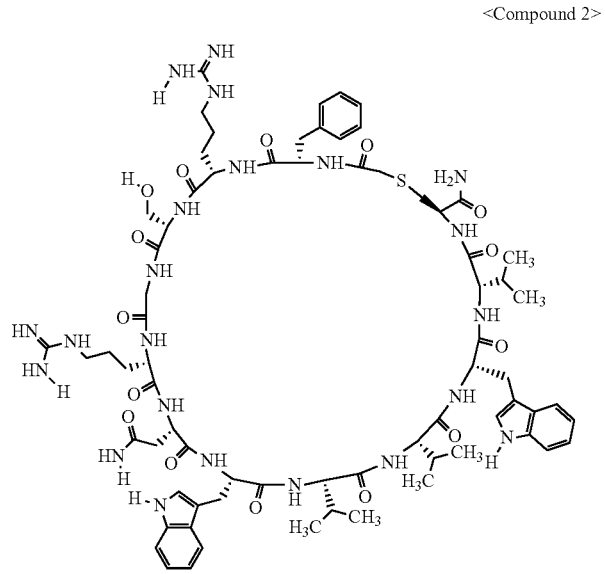

<Compound 2>

[Chem. 80]

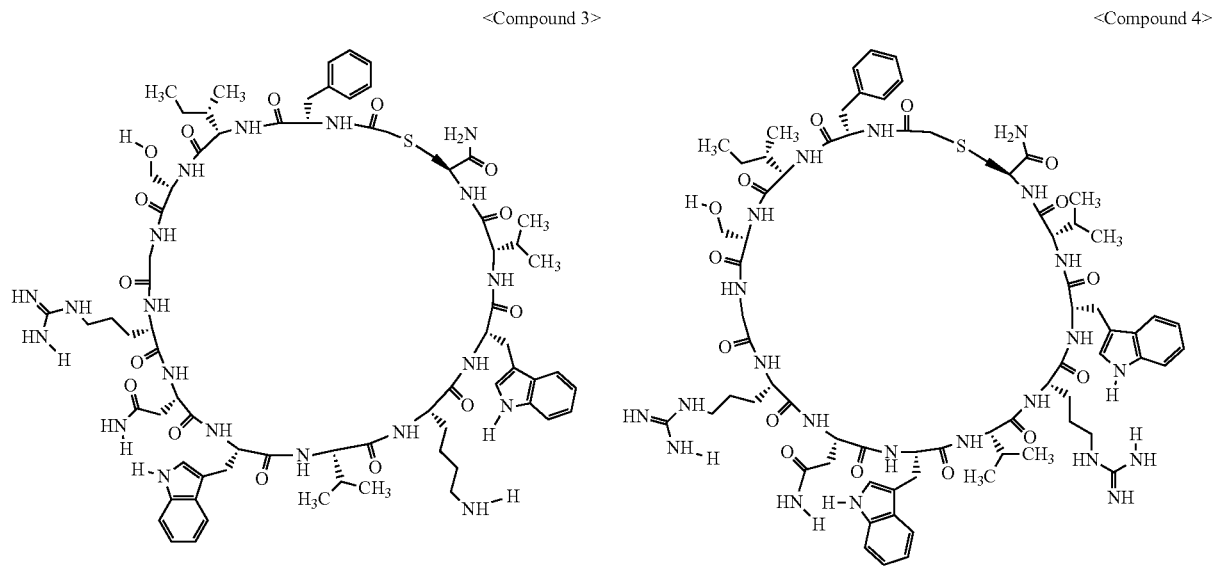

<Compound 3>      <Compound 4>

[Chem. 81]
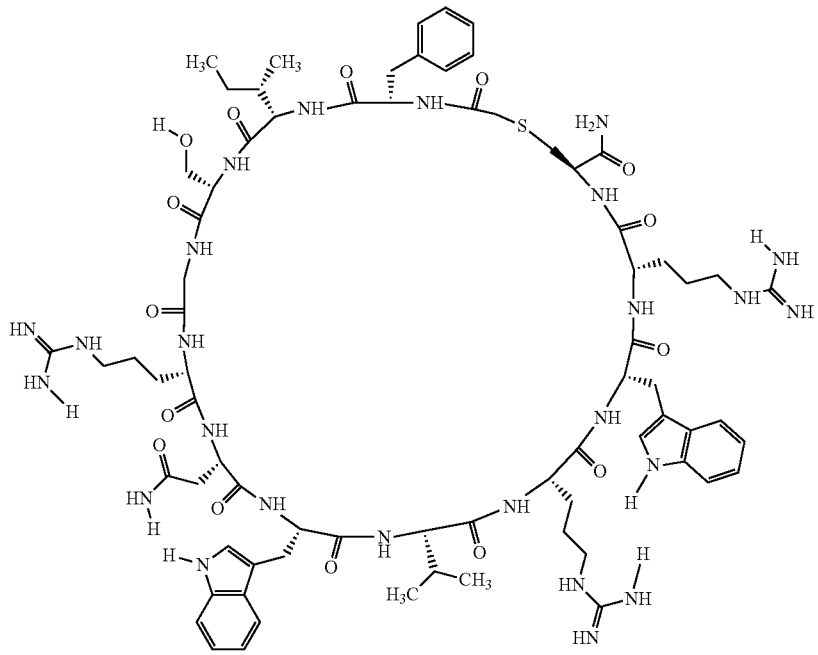
<Compound 5>
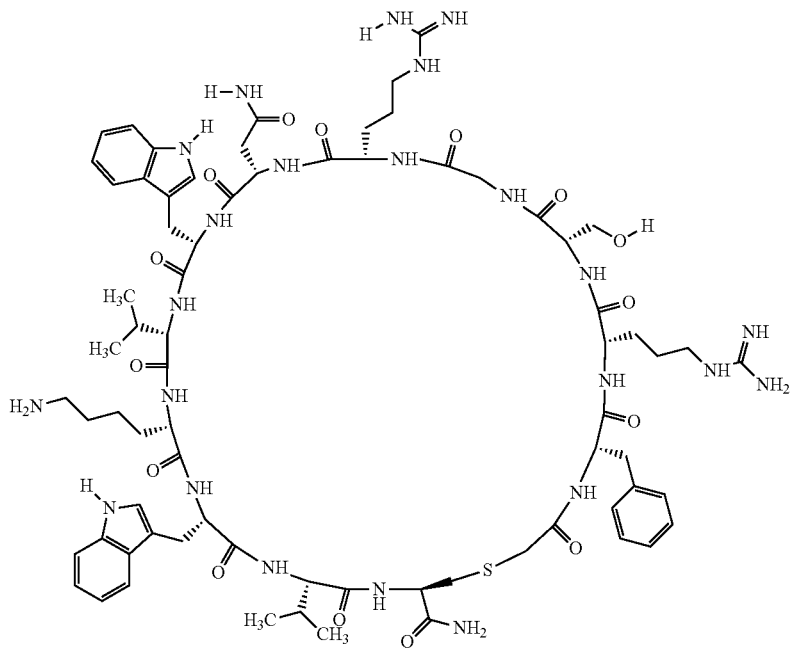
<Compound 6>

-continued
<Compound 7>
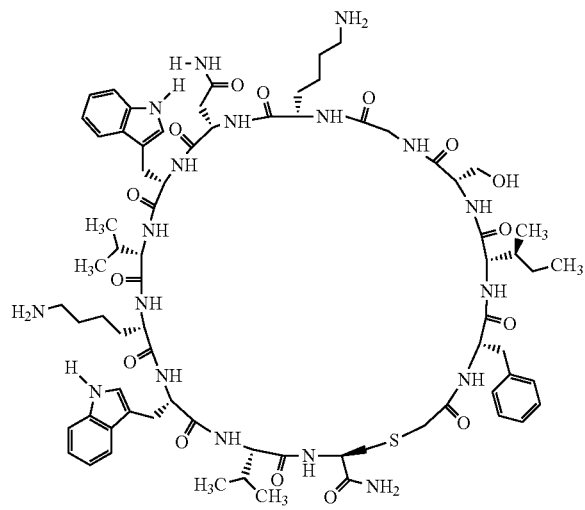
<Compound 8>
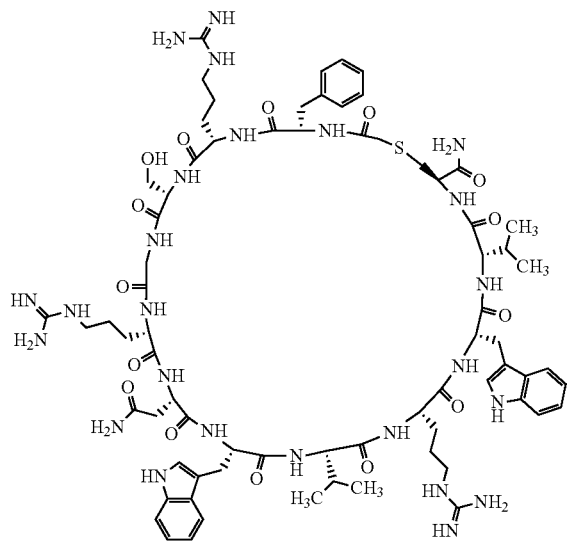
<Compound 9>
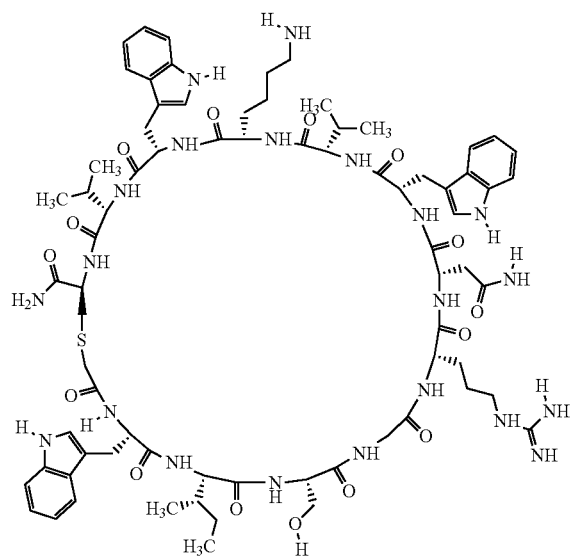
<Compound 10>
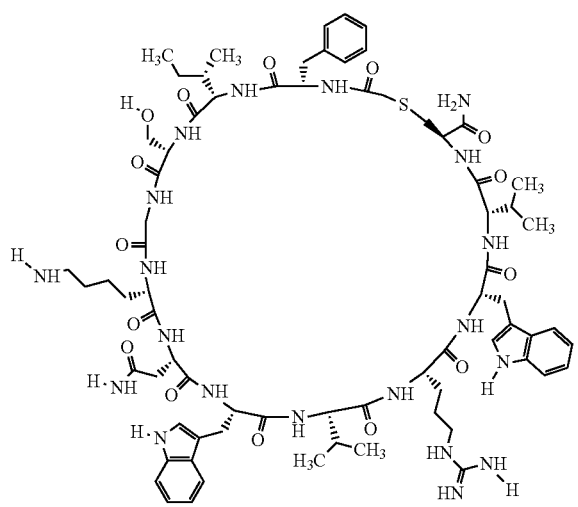

-continued
[Chem. 84]
<Compound 11>
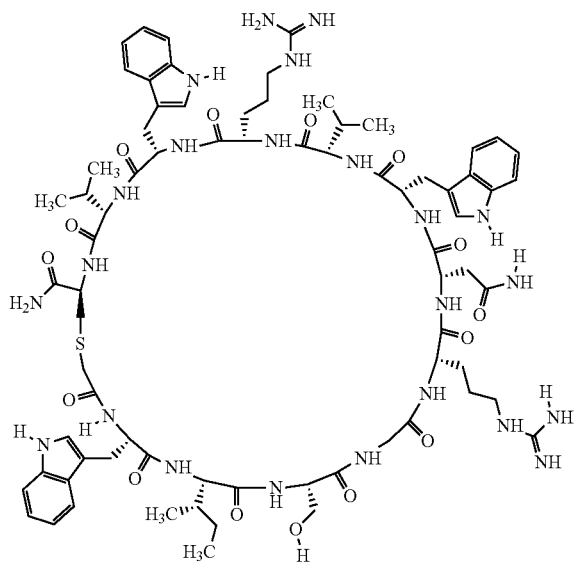
<Compound 12>
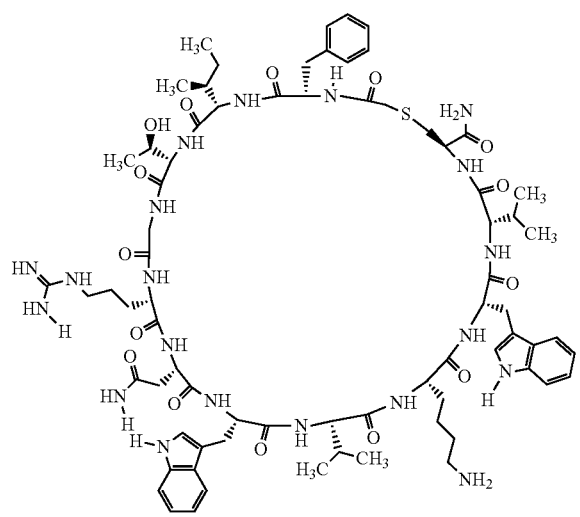
[Chem. 85]
<Compound 13>
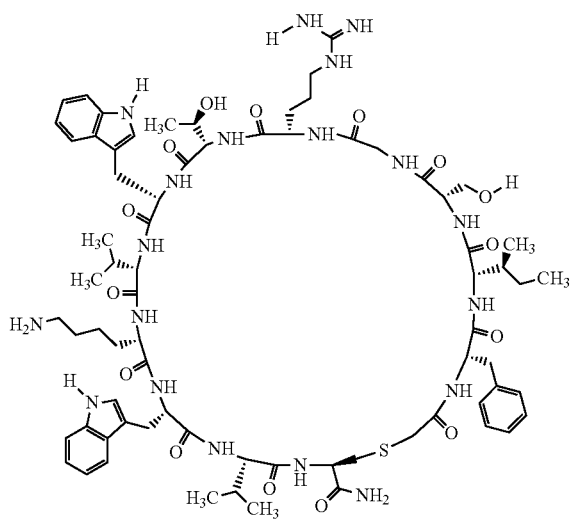
<Compound 14>
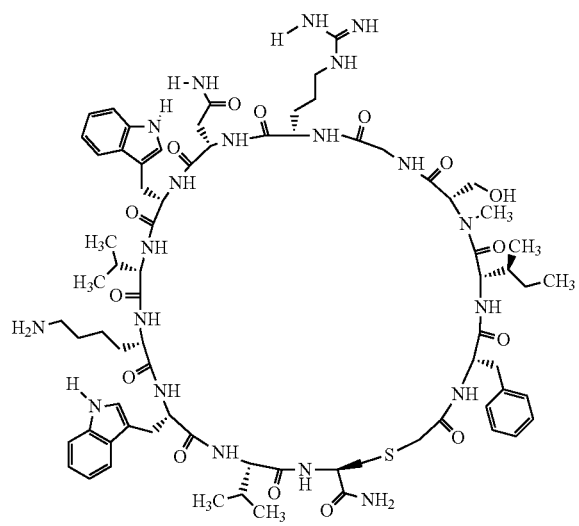

-continued
[Chem. 86]
<Compound 15>
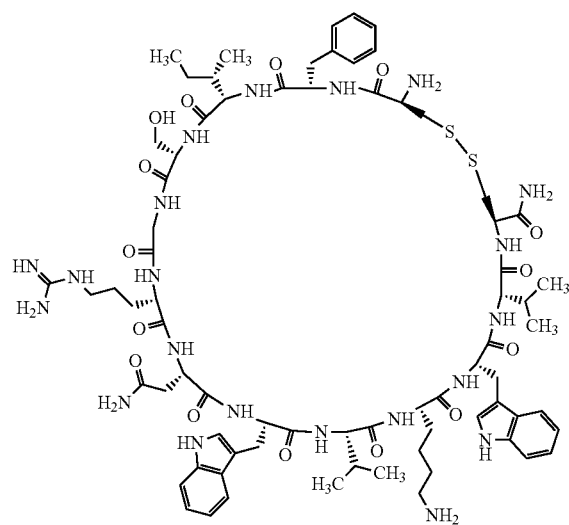
<Compound 16>
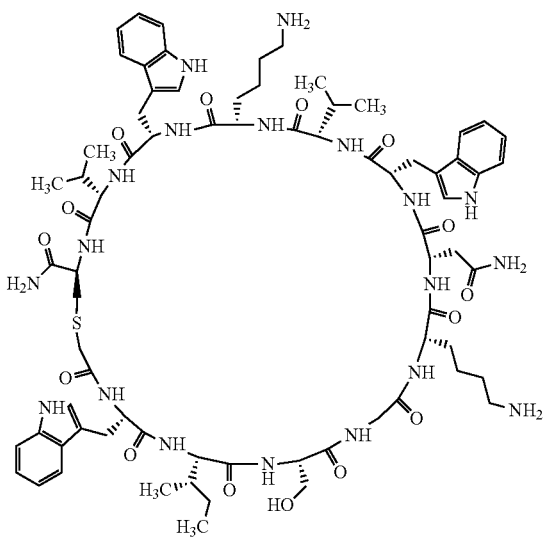
[Chem. 87]
<Compound 17>
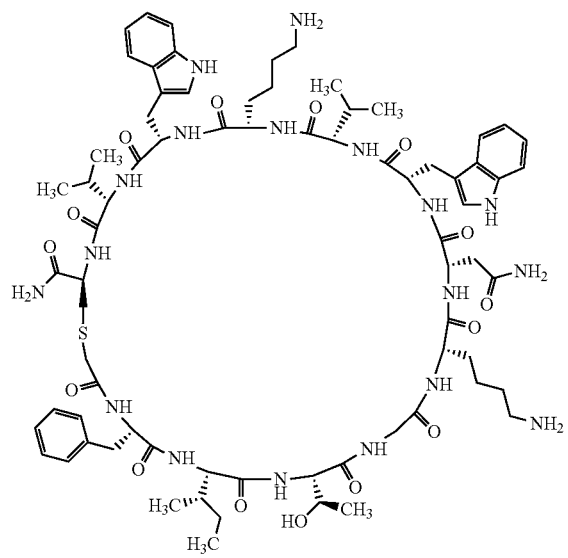
<Compound 18>
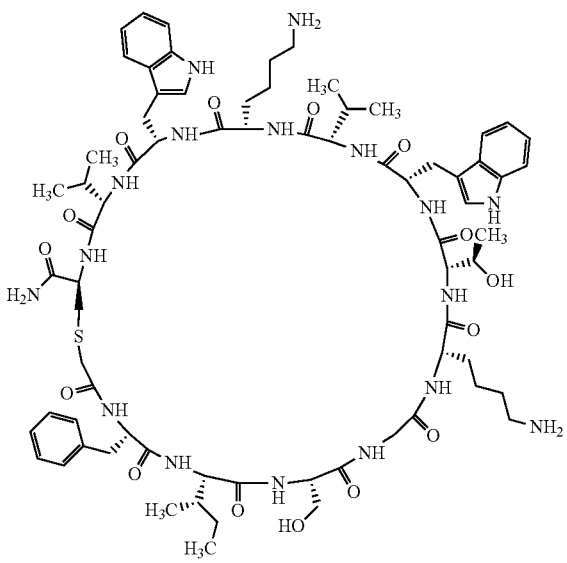

[Chem. 88]
<Compound 19>          <Compound 20>
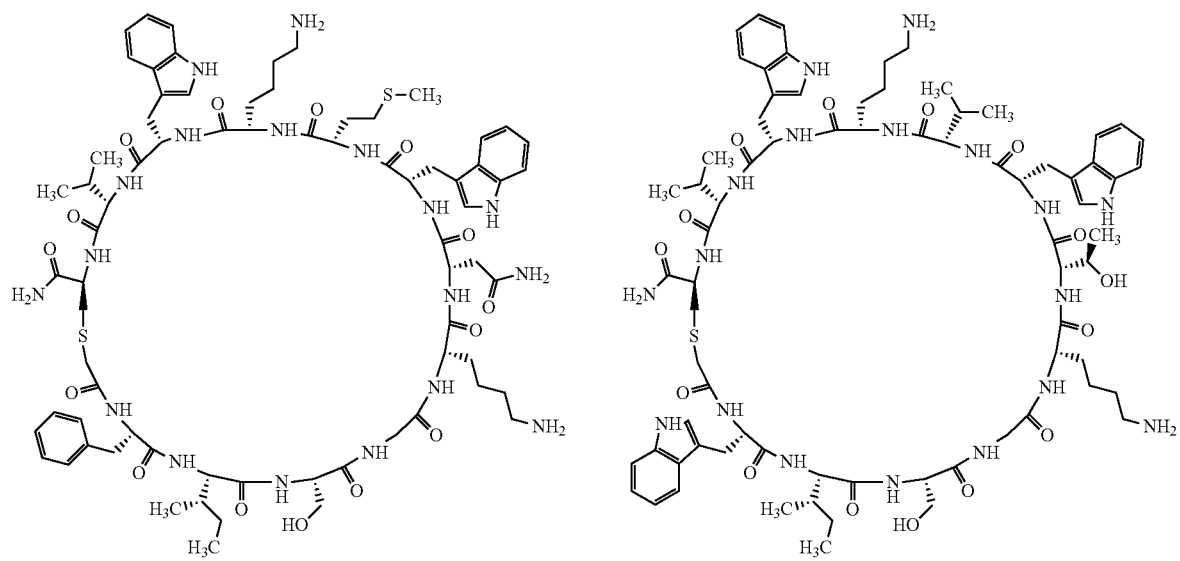
[Chem. 89]
<Compound 21>          <Compound 22>
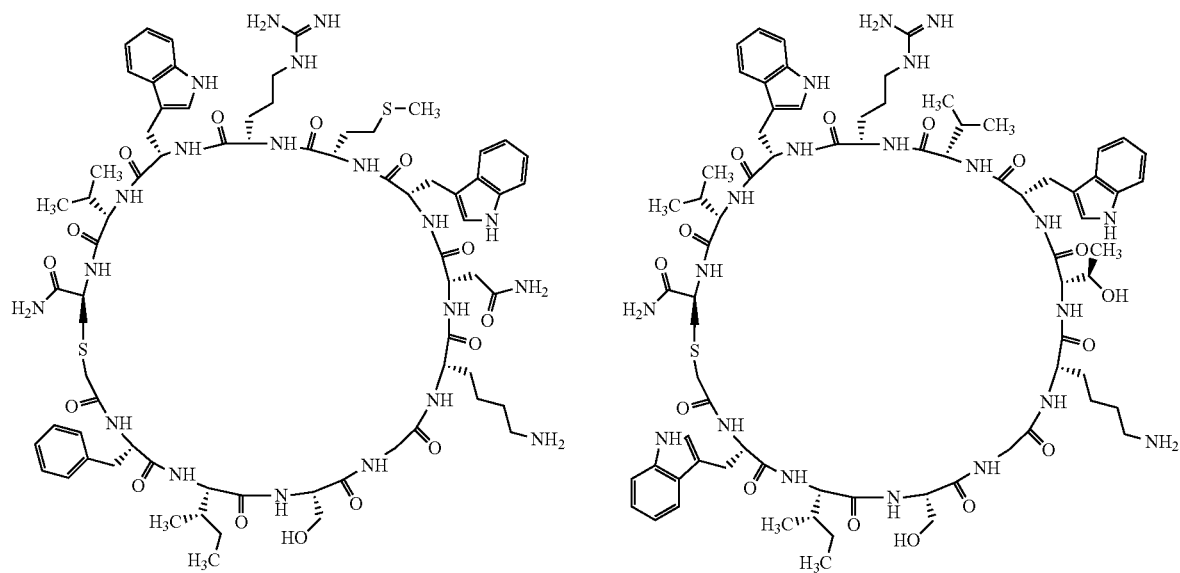

-continued
[Chem. 90]
<Compound 23>
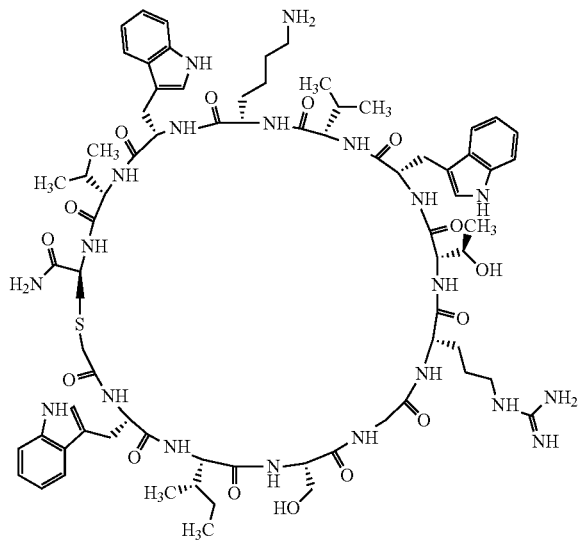
<Compound 24>
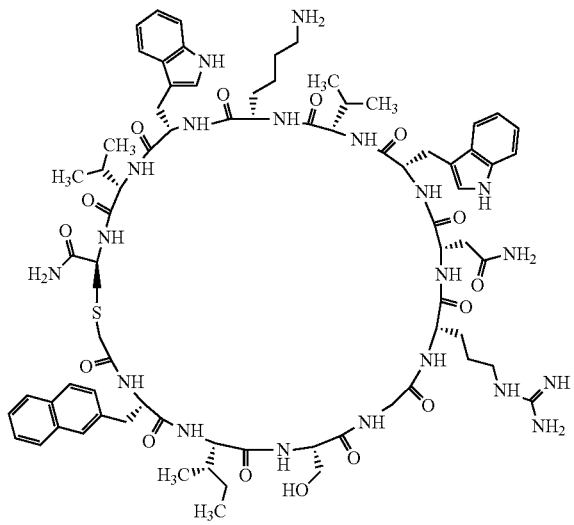
[Chem. 91]
<Compound 25>
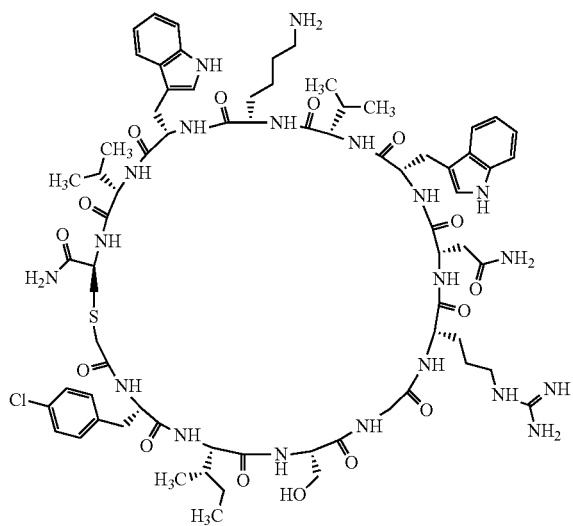
<Compound 26>
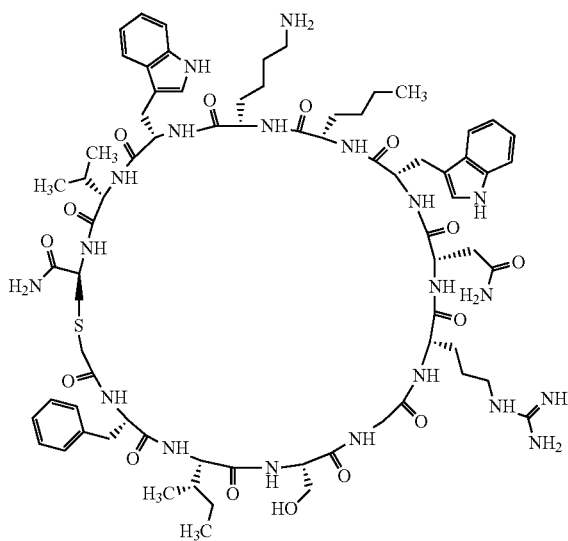

<Compound 27>
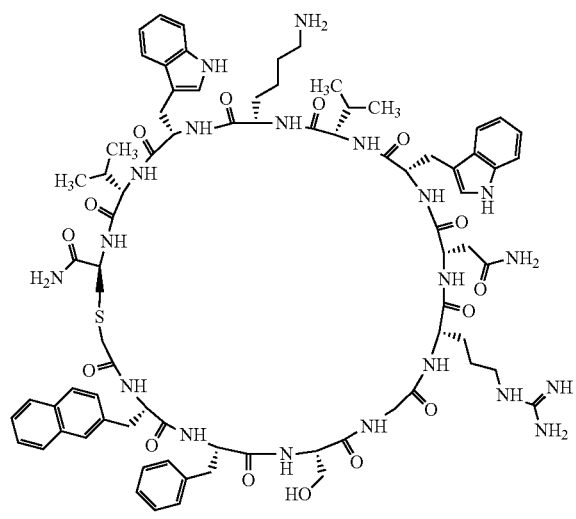
<Compound 28>
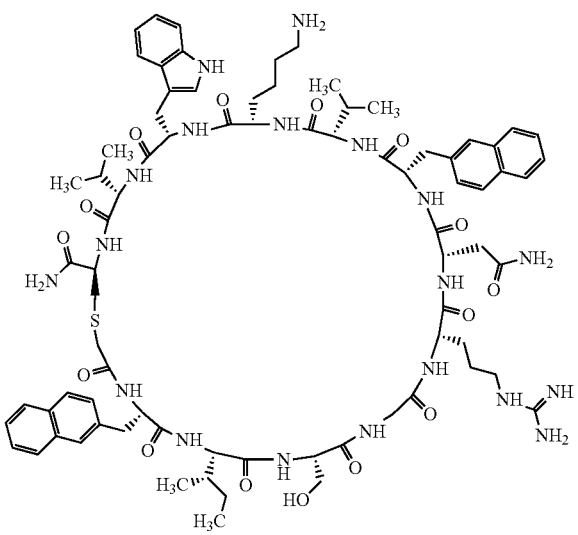
<Compound 29>
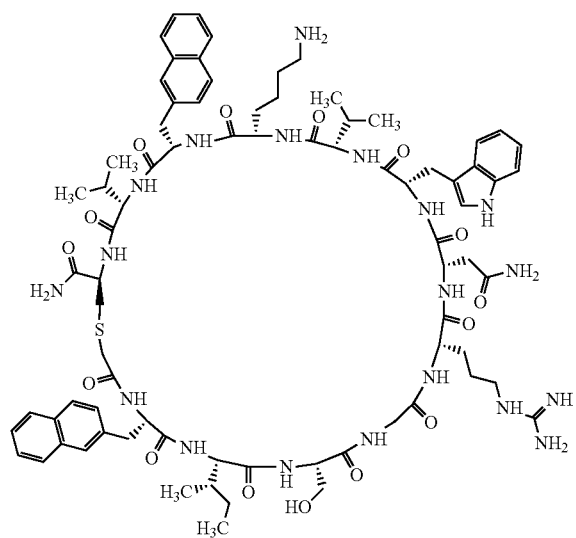
<Compound 30>
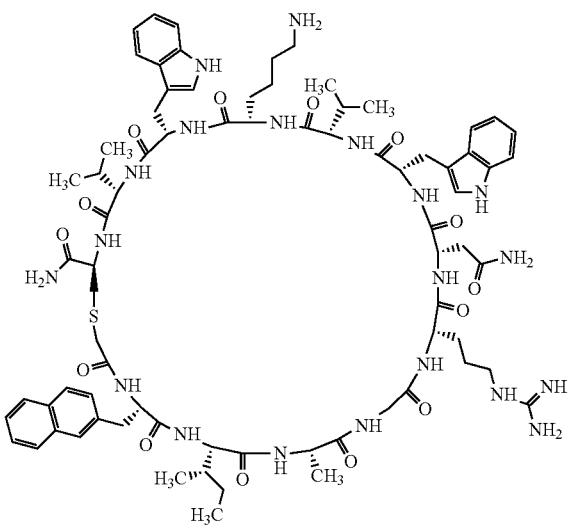

[Chem. 96]
<Compound 35>
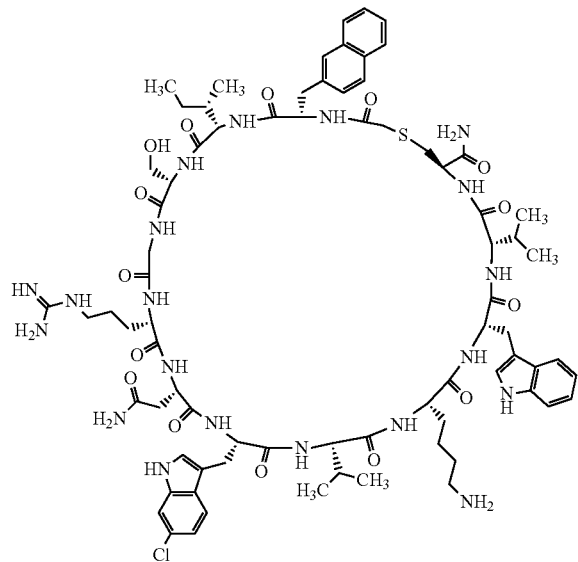
<Compound 36>
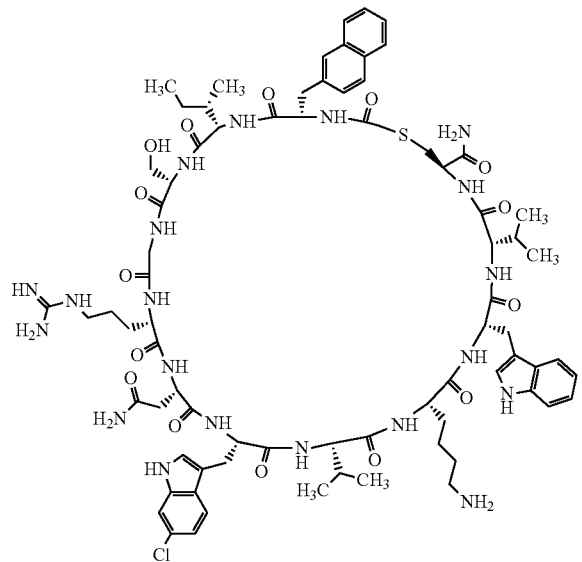
[Chem. 97]
<Compound 37>
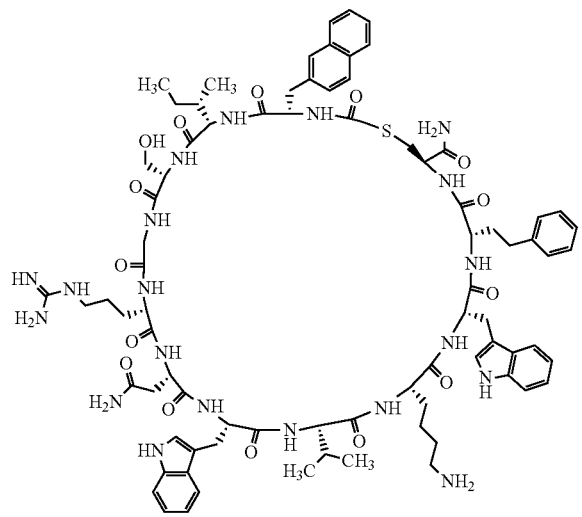
<Compound 38>
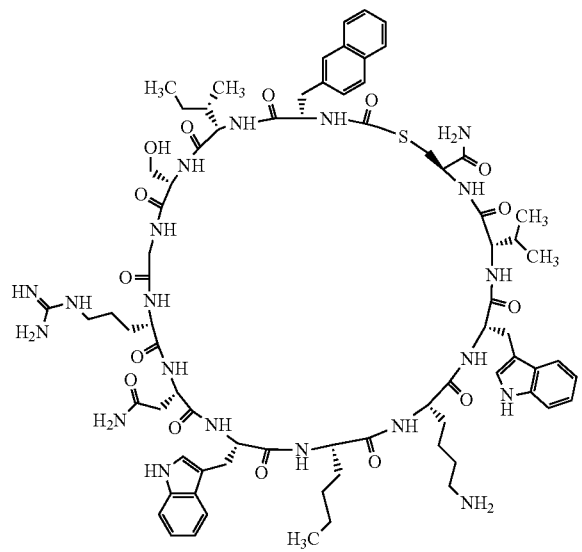

[Chem. 98]
<Compound 39>
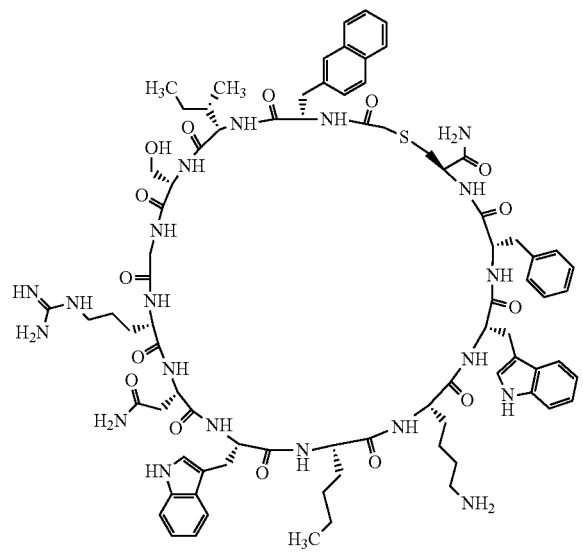
<Compound 40>
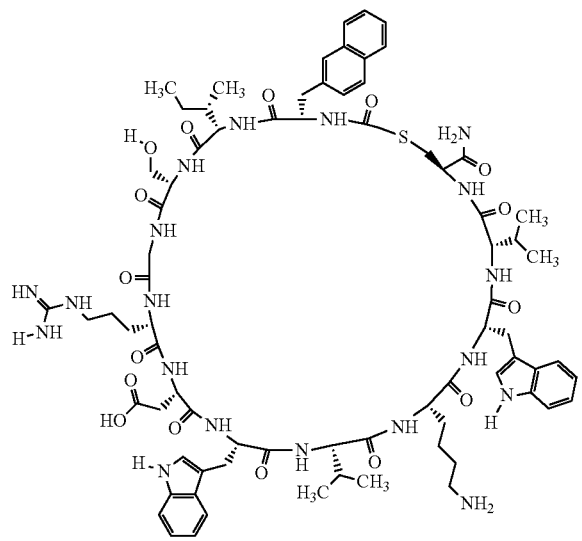
[Chem. 99]
<Compound 41>
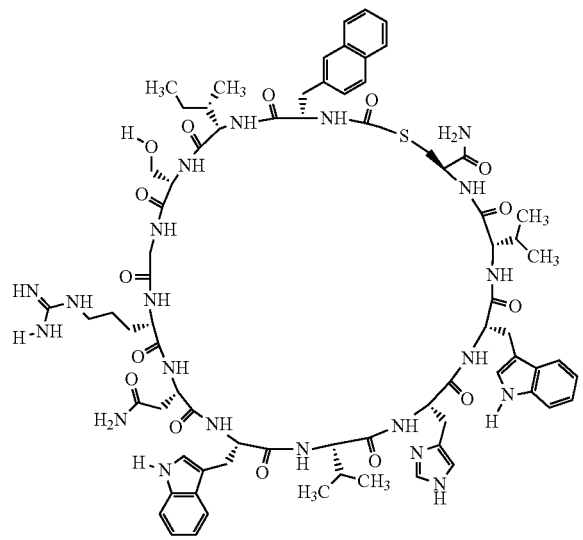
<Compound 42>
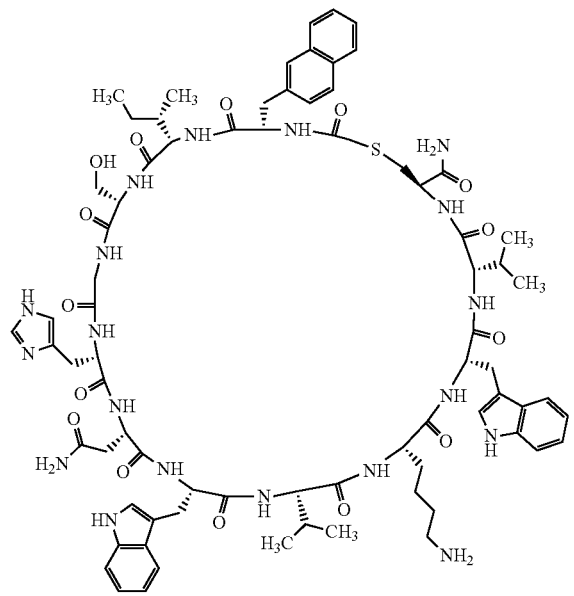

-continued
[Chem. 100]
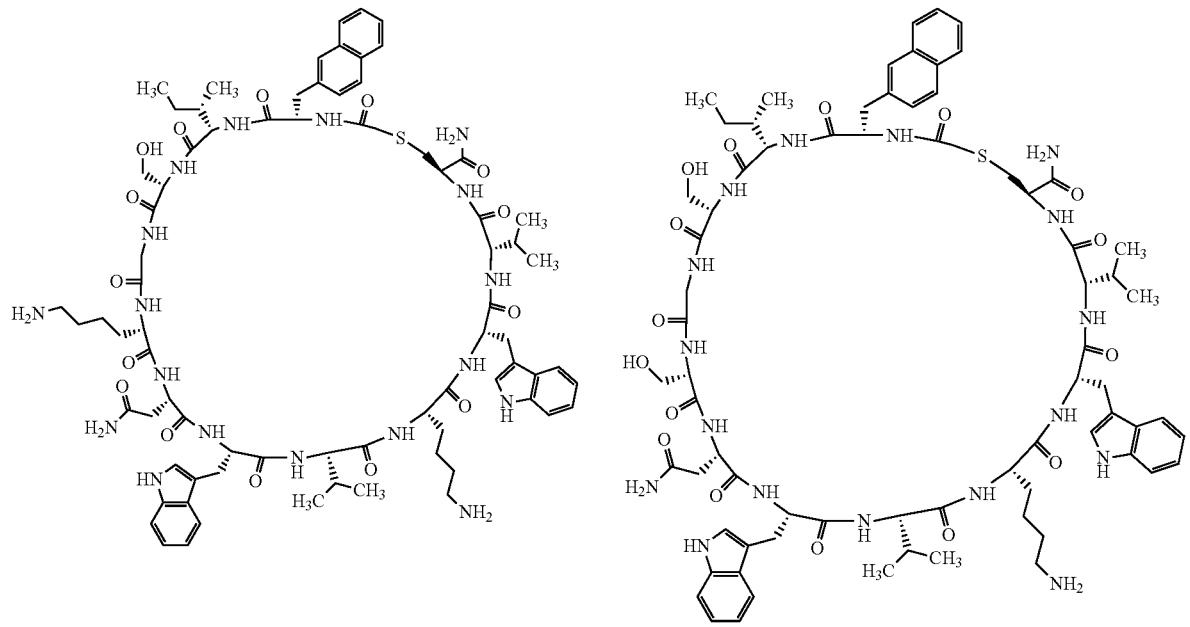
<Compound 43>  <Compound 44>
[Chem. 101]
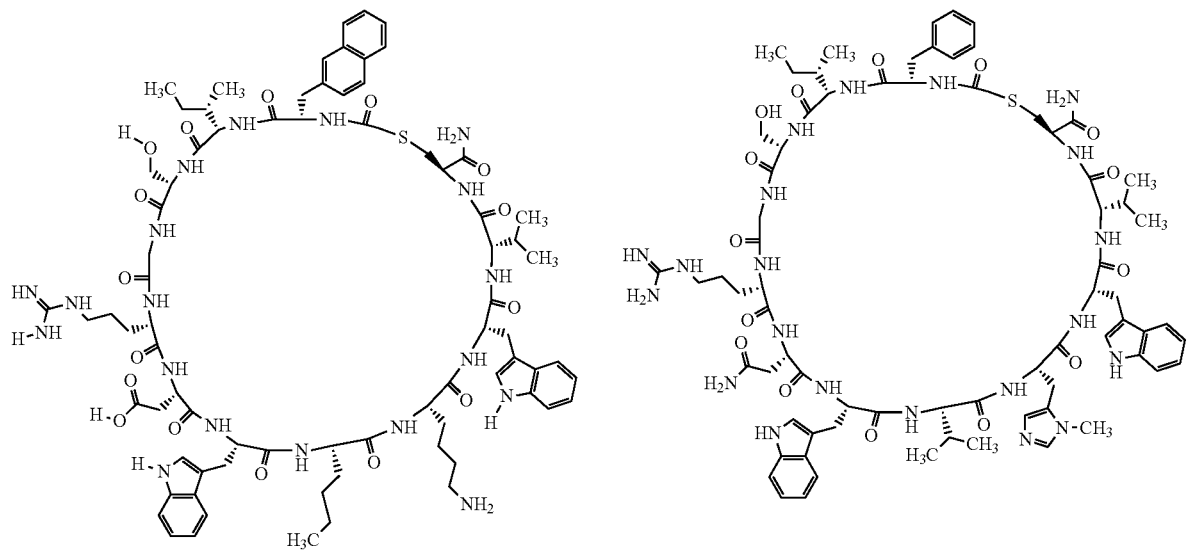
<Compound 45>  <Compound 46>

-continued
[Chem. 102]
<Compound 47>
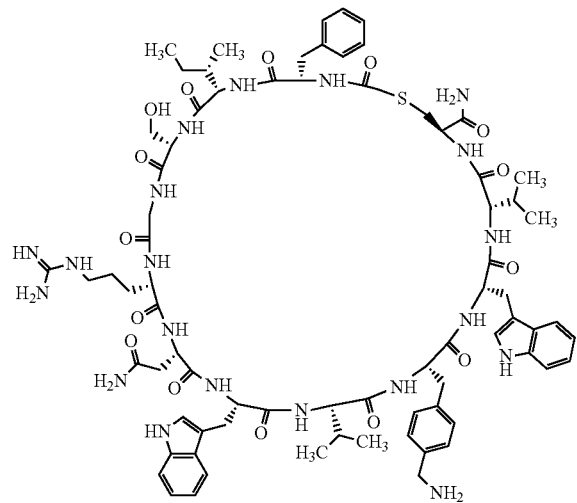
<Compound 48>
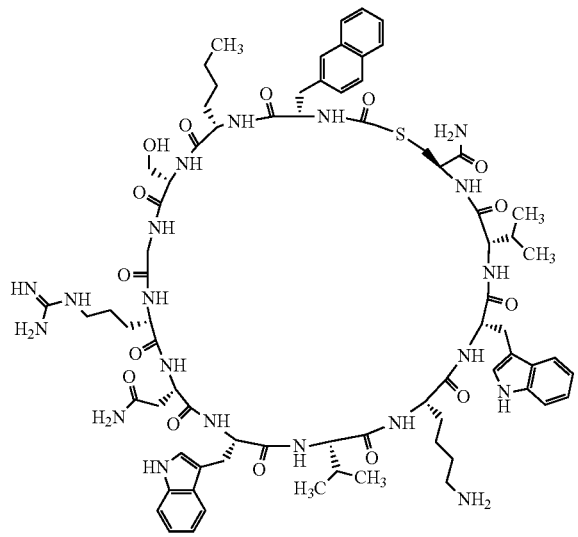
[Chem. 103]
<Compound 49>
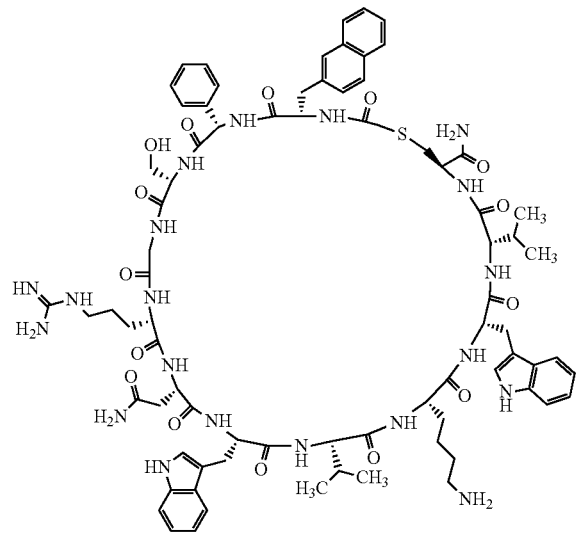
<Compound 50>
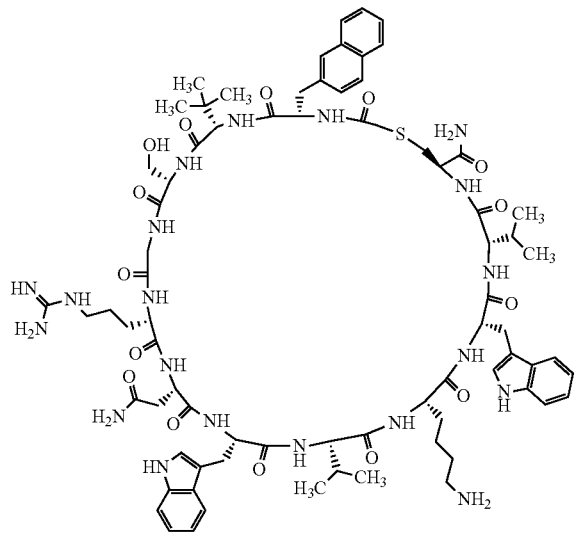

[Chem. 104]
<Compound 51>
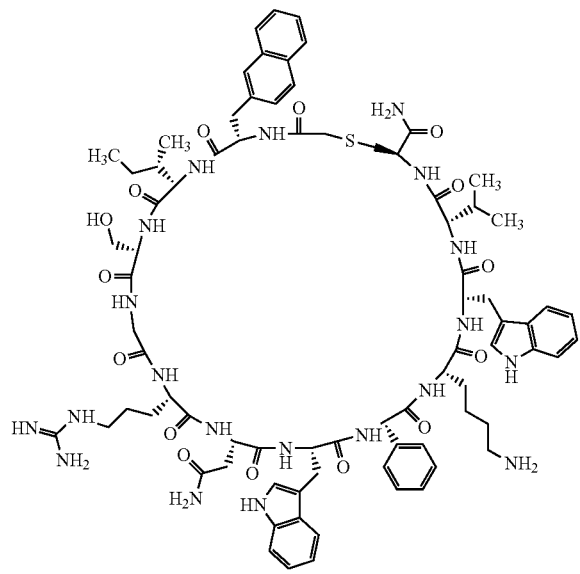
<Compound 52>
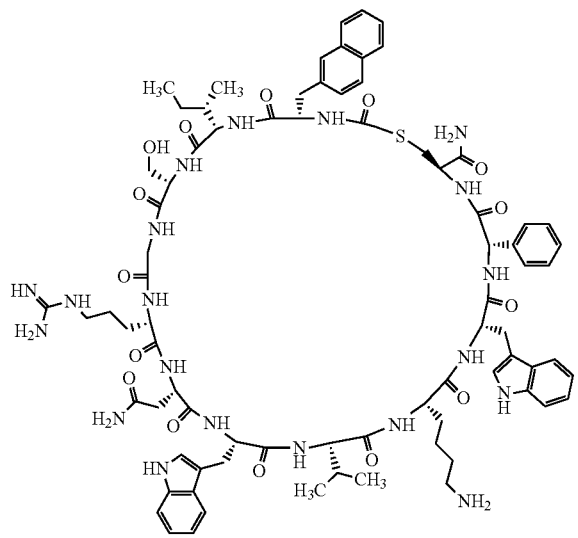
[Chem. 105]
<Compound 53>
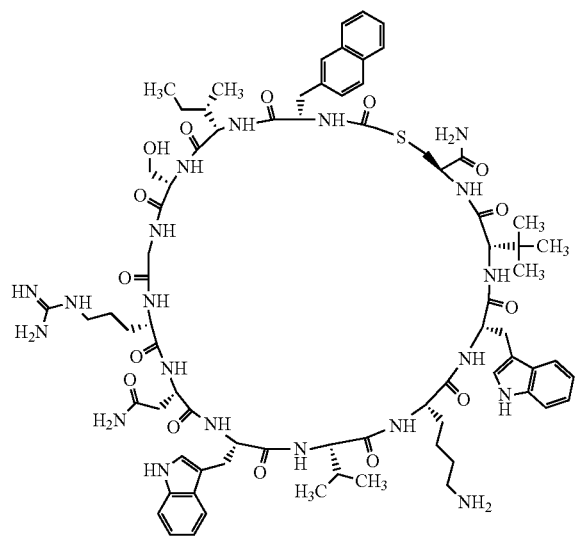
<Compound 54>
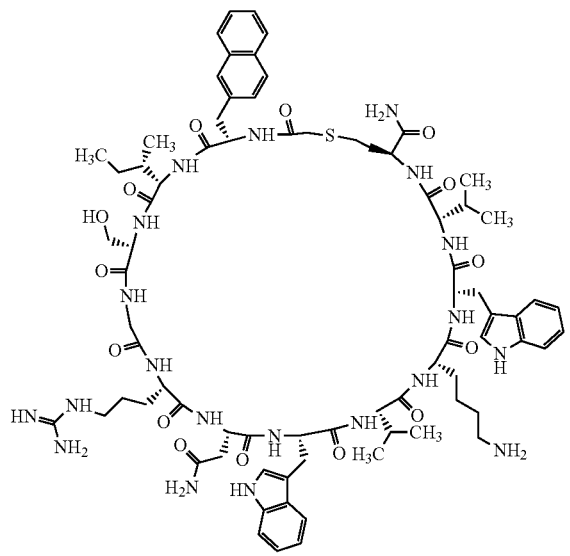

-continued
[Chem. 106]
<Compound 55>
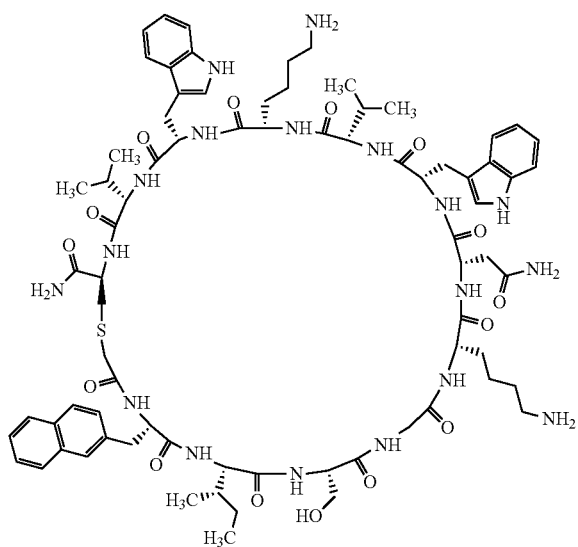
<Compound 56>
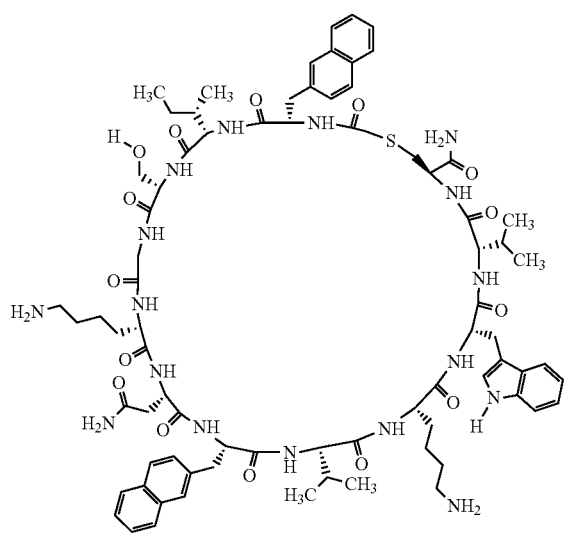
[Chem. 107]
<Compound 57>
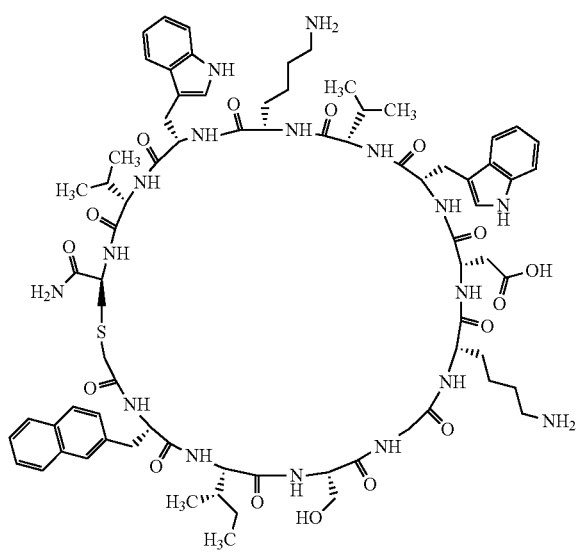
<Compound 58>
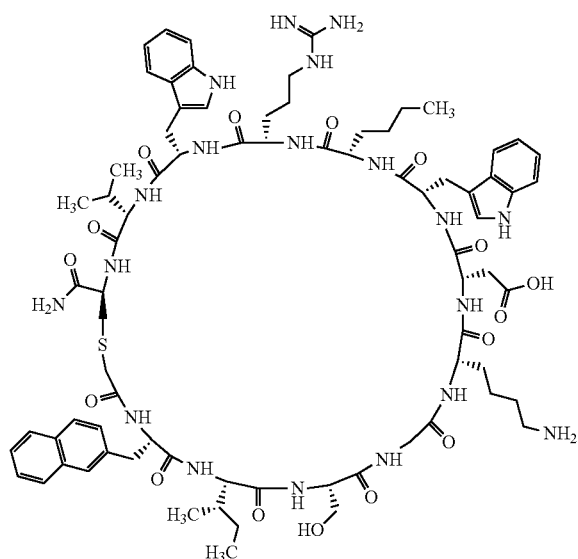

-continued
[Chem. 108]
<Compound 59>
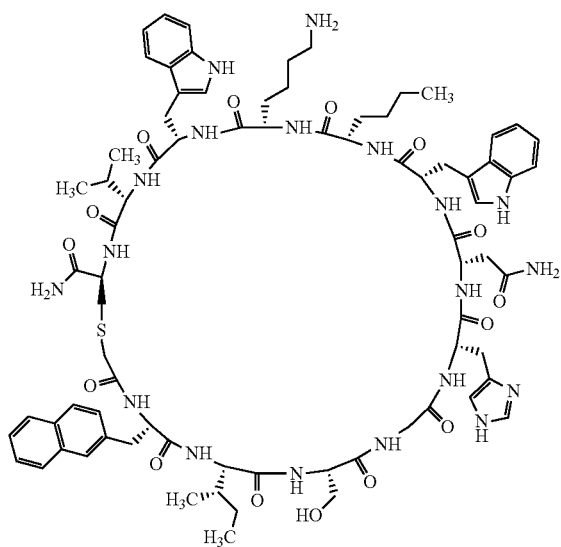
<Compound 60>
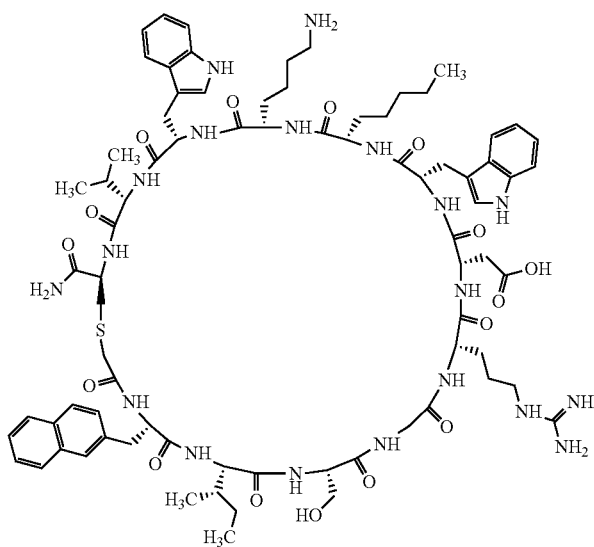
[Chem. 109]
<Compound 61>
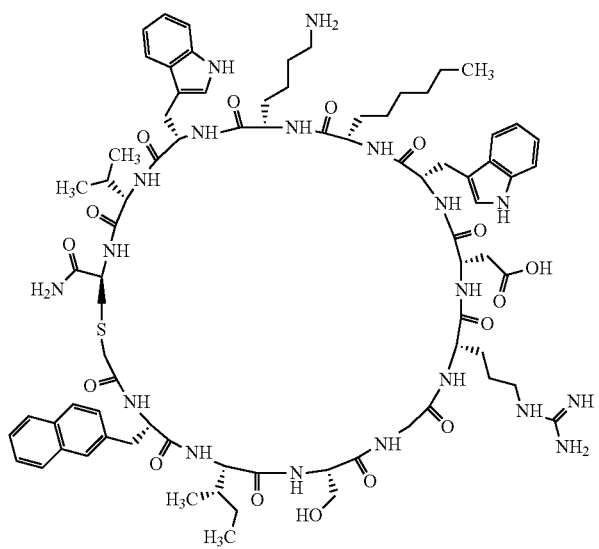
<Compound 62>
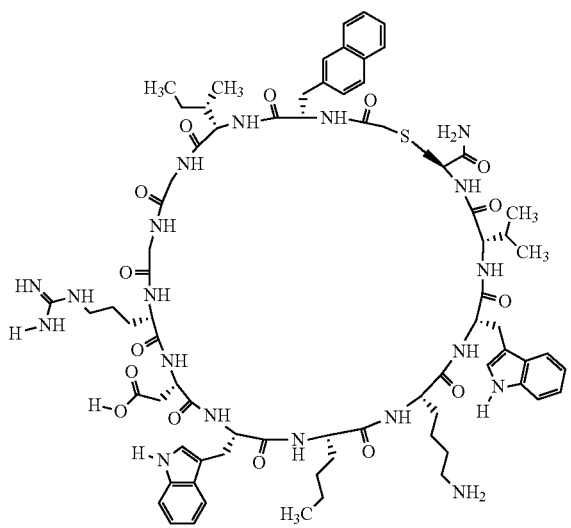

-continued
[Chem. 110]
<Compound 63>
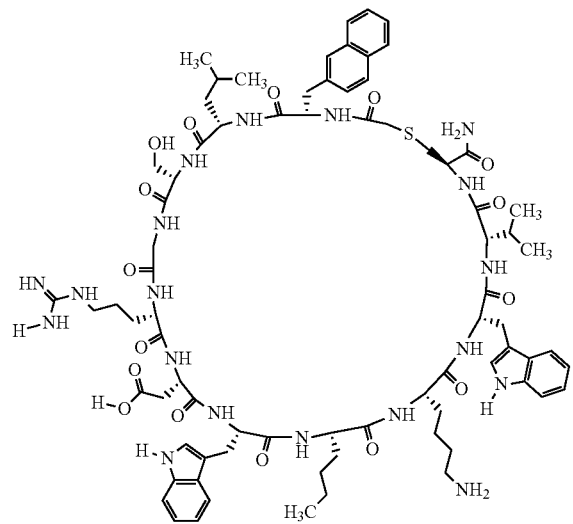
<Compound 64>
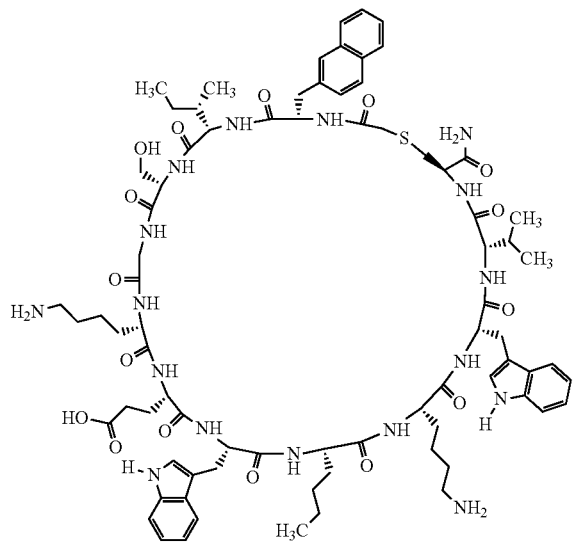
[Chem. 111]
<Compound 65>
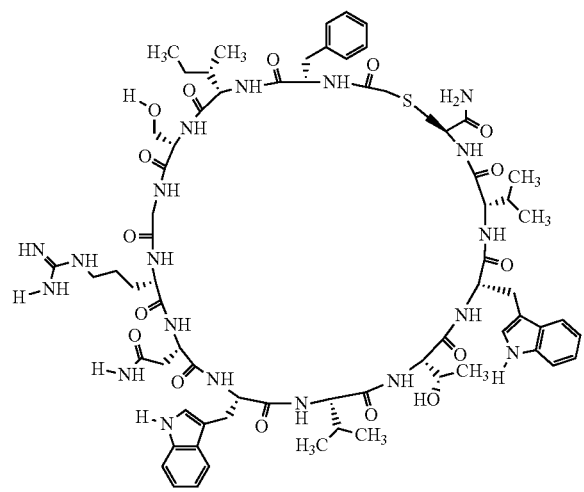
<Compound 66>
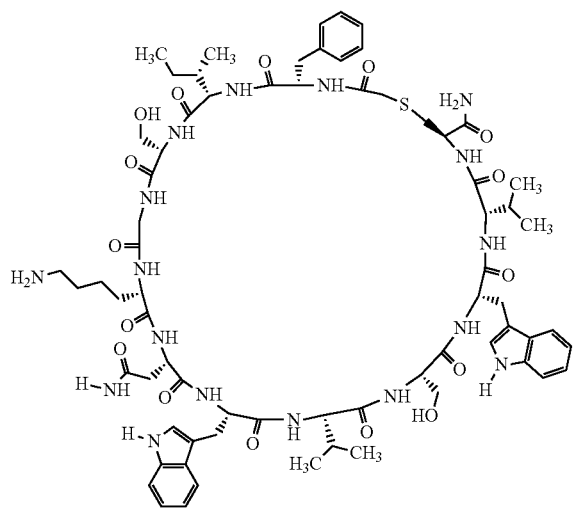

[Chem. 112]
<Compound 67>
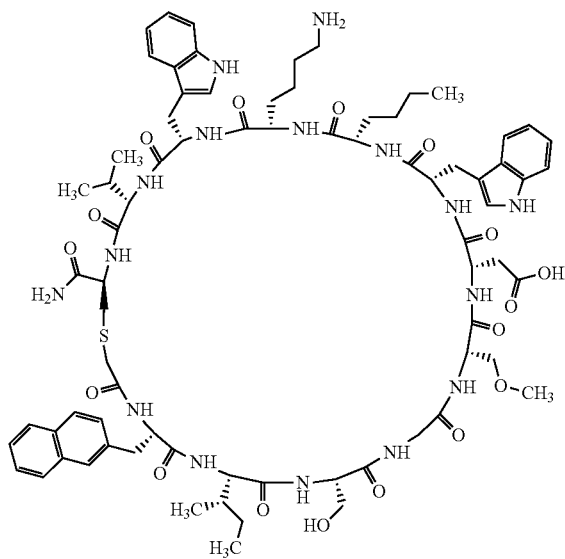
<Compound 68>
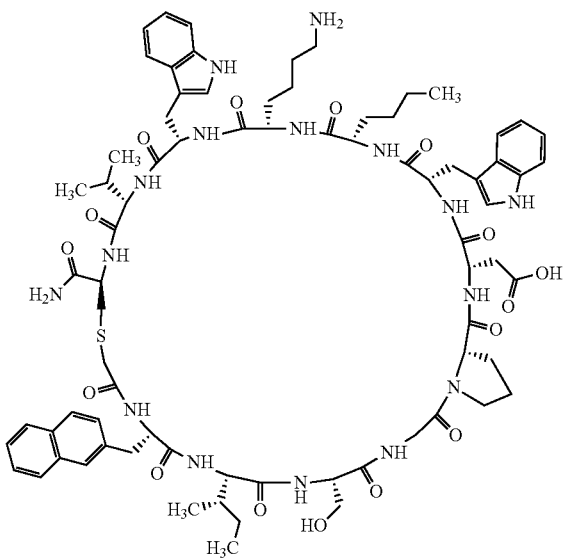
[Chem. 113]
<Compound 69>
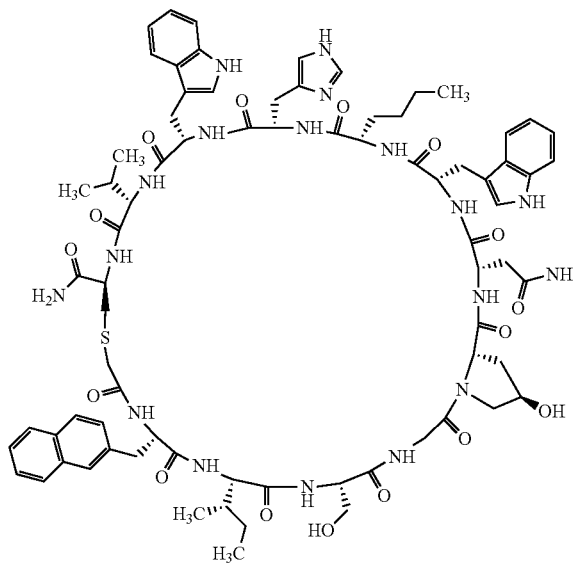
<Compound 70>
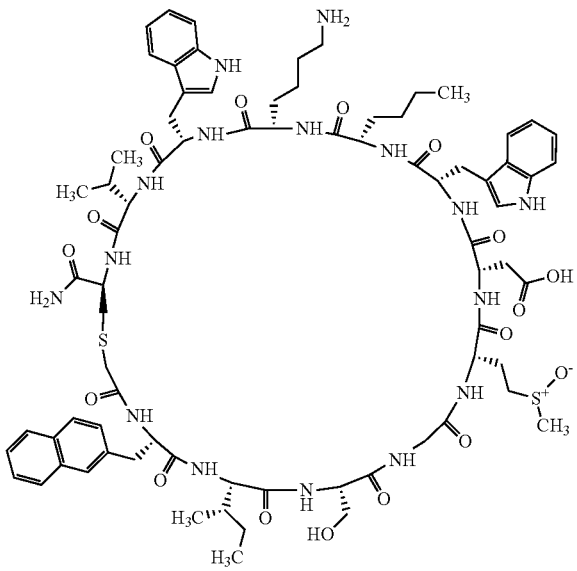

-continued
[Chem. 114]
<Compound 71>
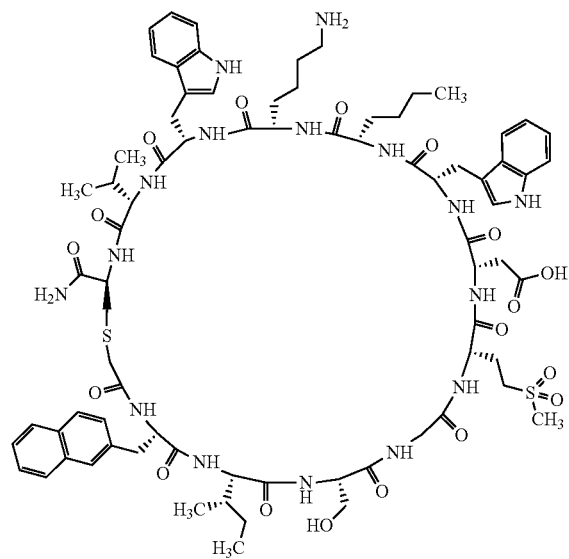
<Compound 72>
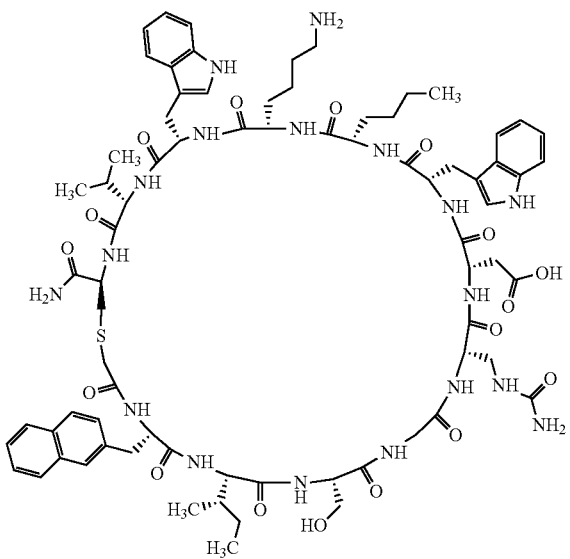
[Chem. 115]
<Compound 73>
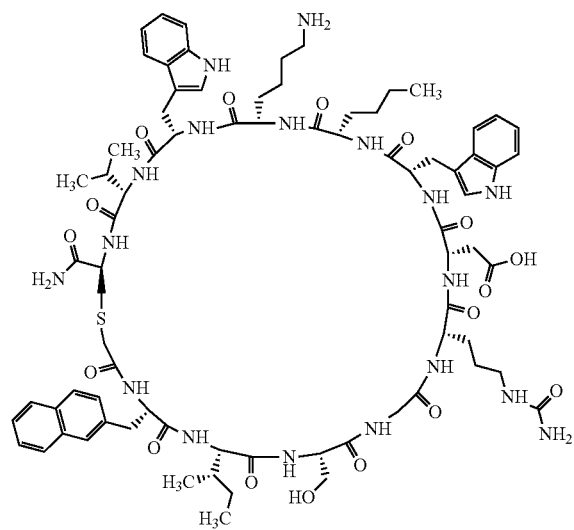
<Compound 74>
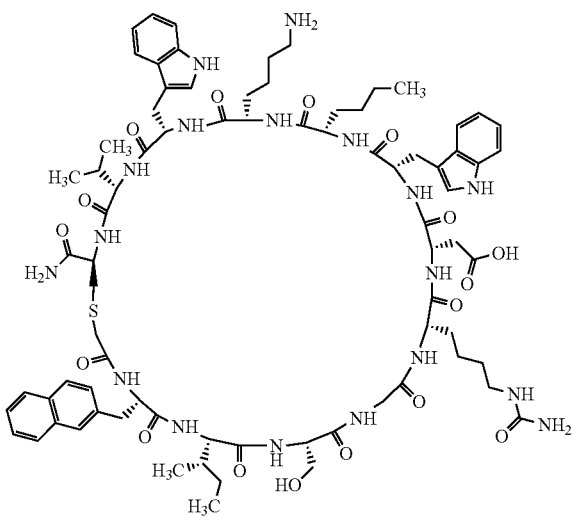

[Chem. 116]
<Compound 75>
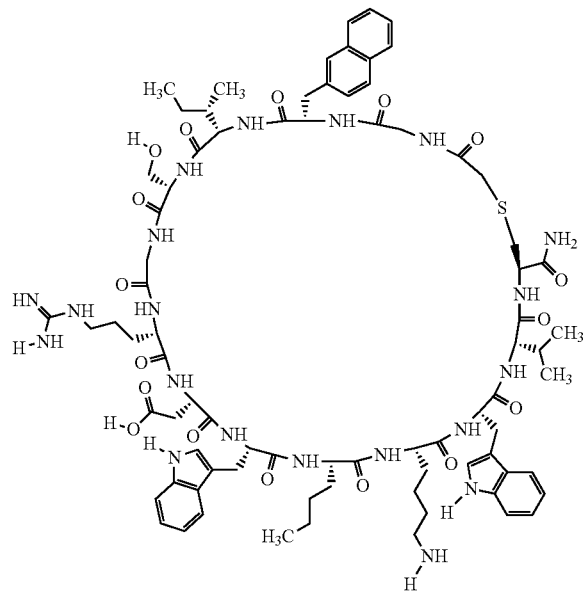
<Compound 76>
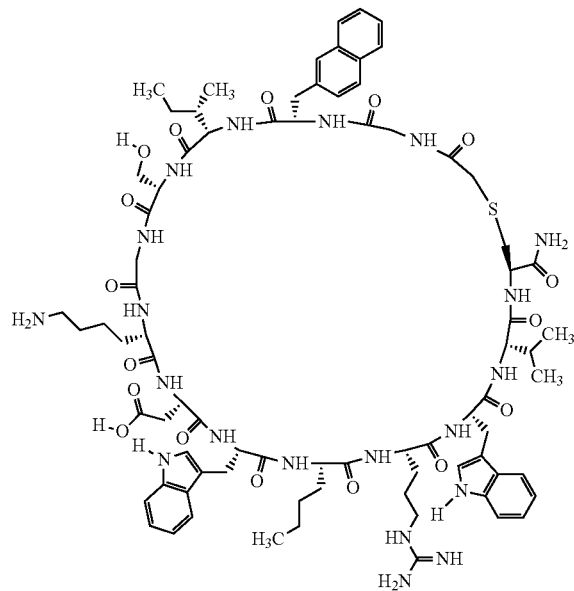
[Chem. 117]
<Compound 77>
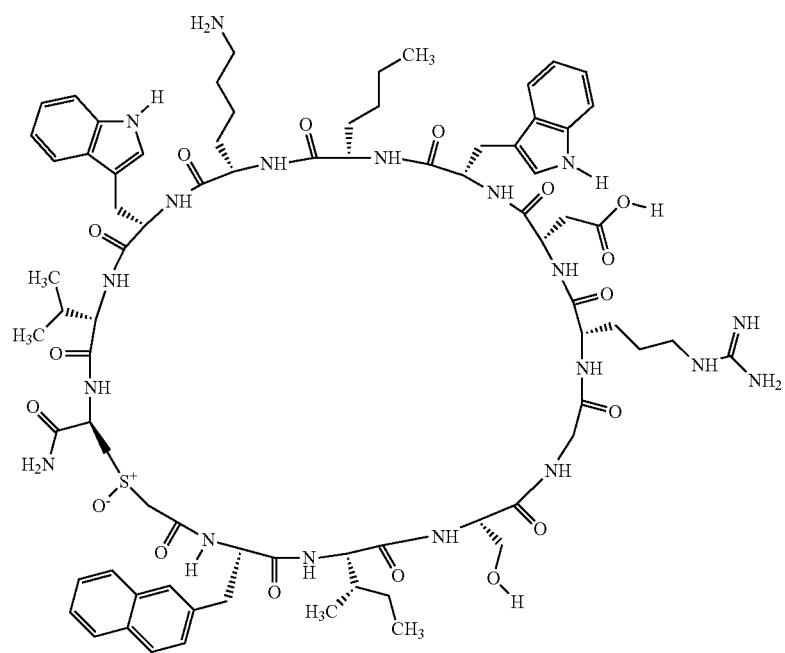

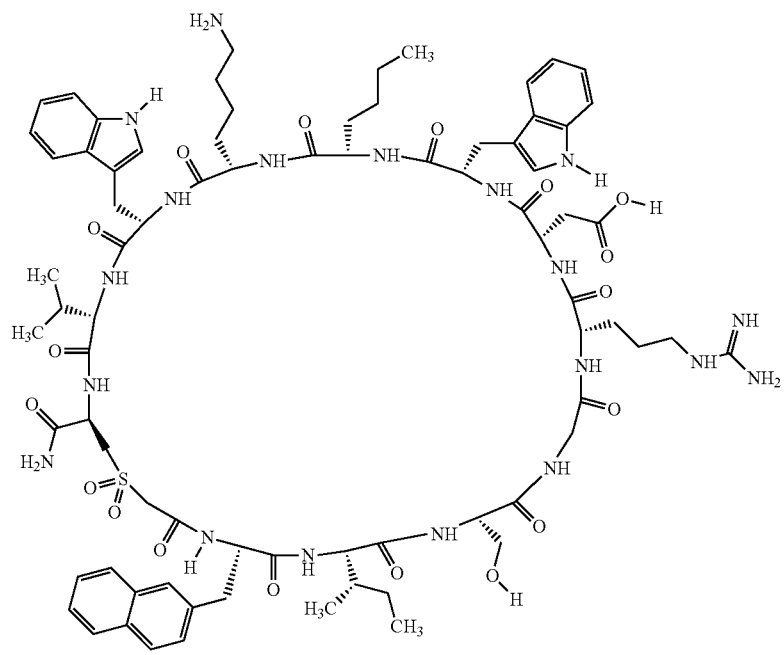
<Compound 78>
[Chem. 118]
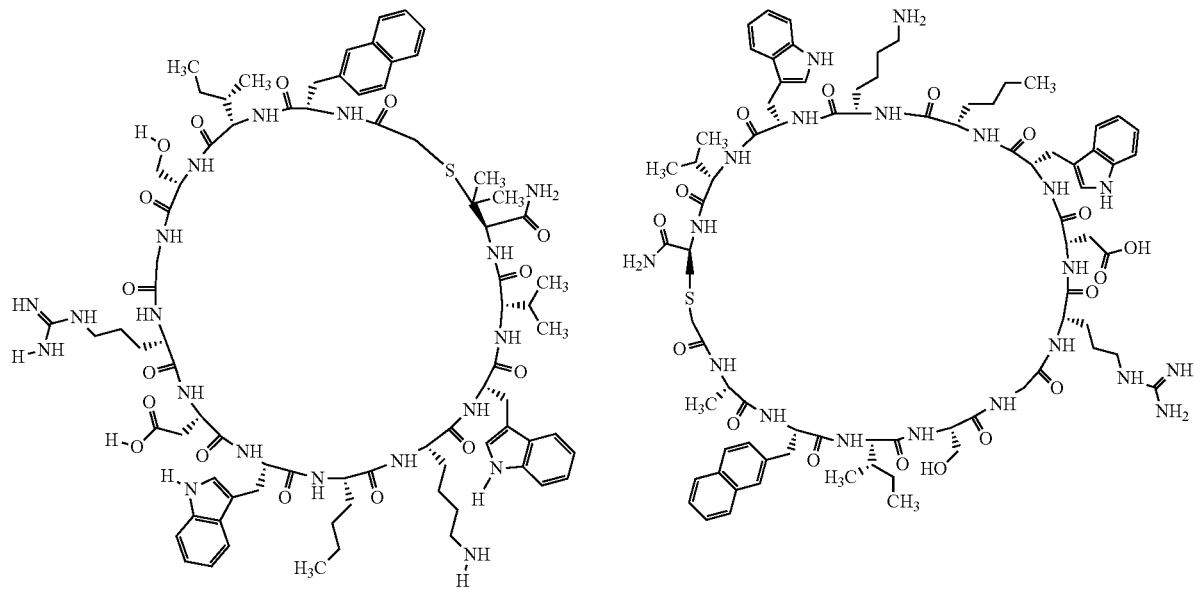
<Compound 79>  <Compound 80>

[Chem. 119]
<Compound 81>                          <Compound 82>
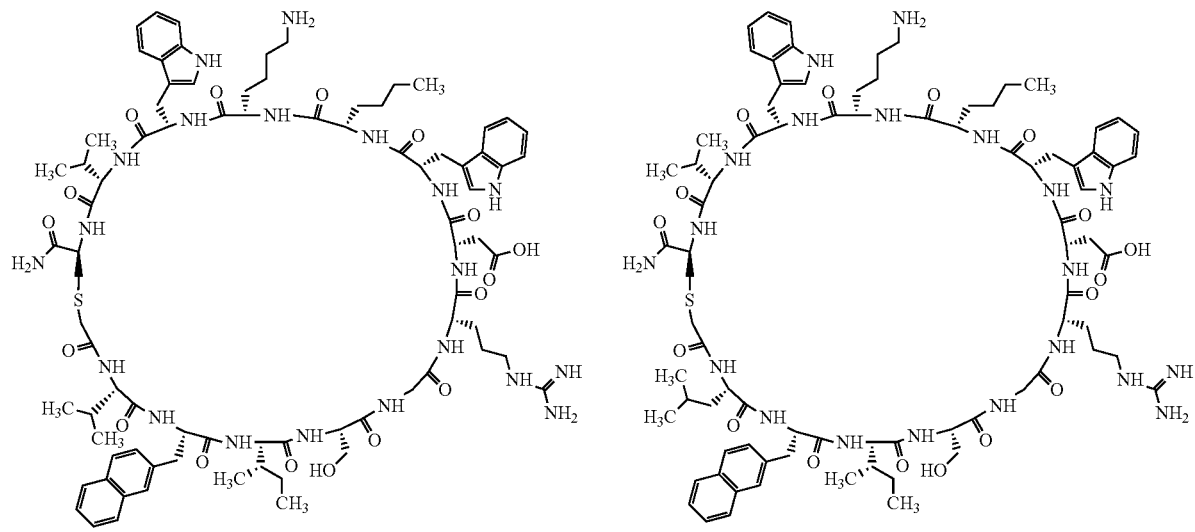
[Chem. 120]
<Compound 83>                          <Compound 84>
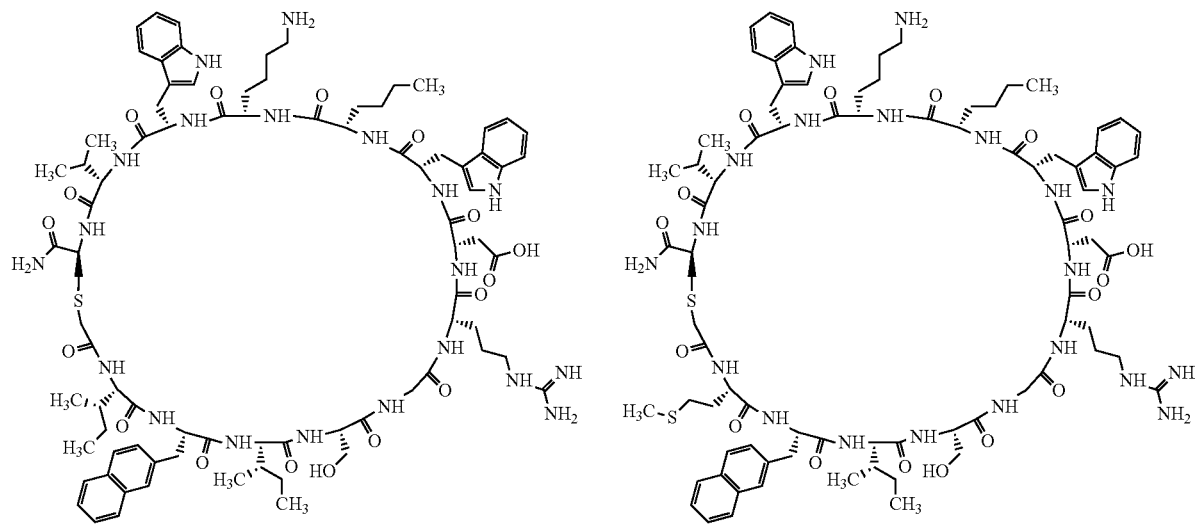

[Chem. 121]
<Compound 85>
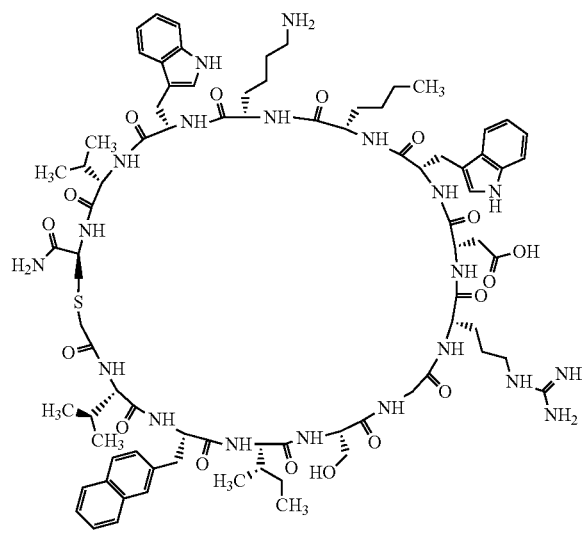
<Compound 86>
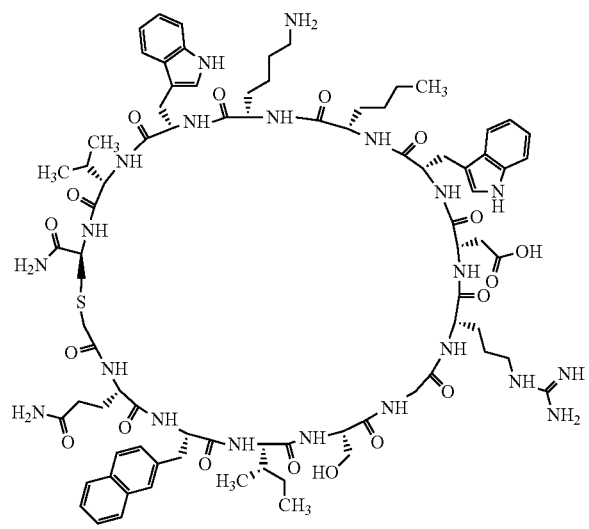
[Chem. 122]
<Compound 87>
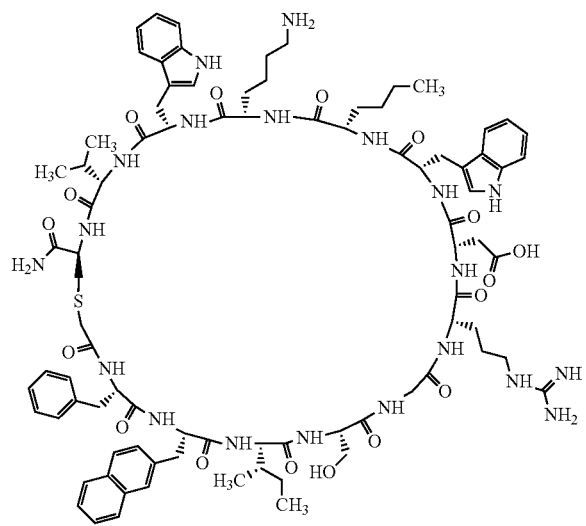
<Compound 88>
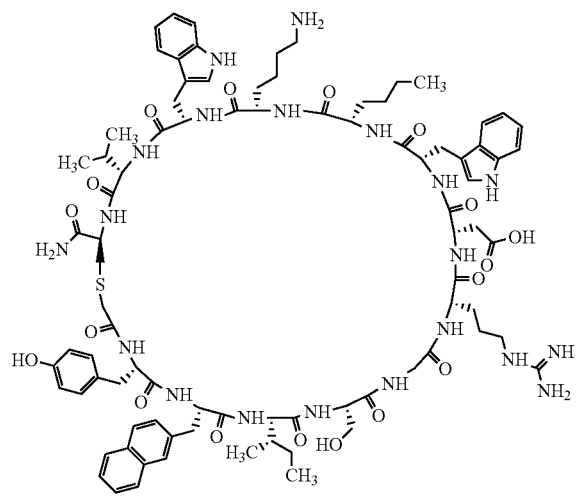

-continued
[Chem. 123]
<Compound 89>
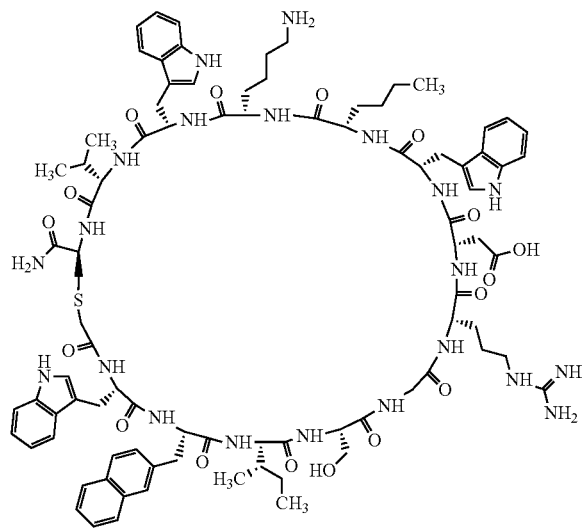
<Compound 90>
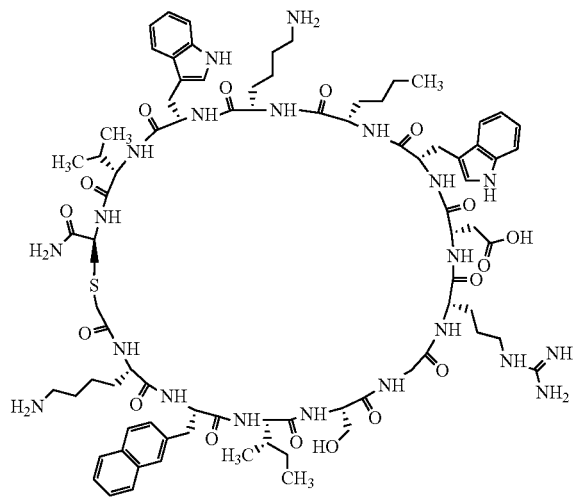
[Chem. 124]
<Compound 91>
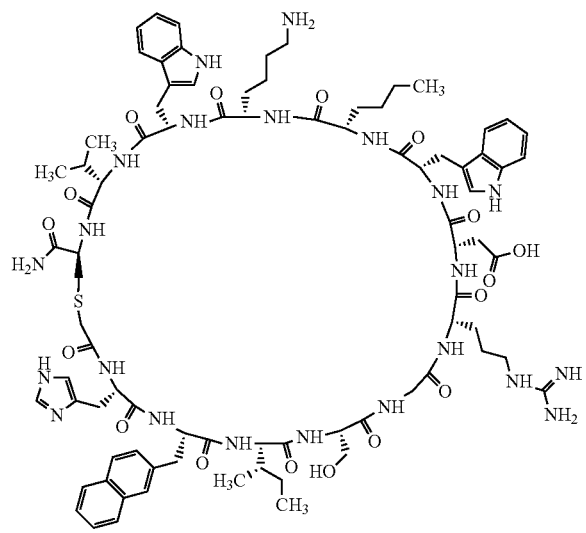
<Compound 92>
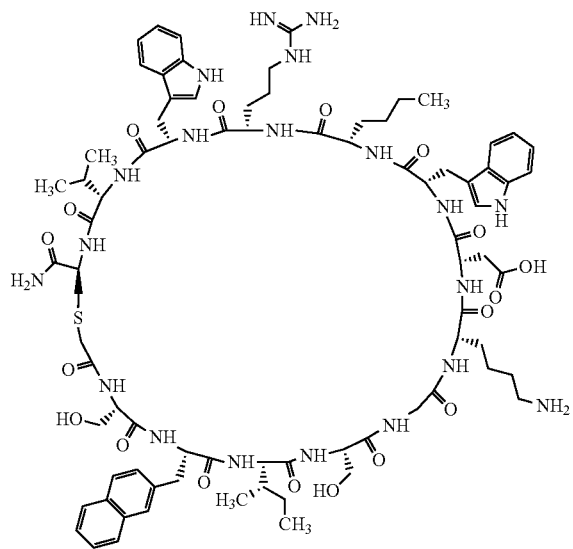

[Chem. 125]
<Compound 93>
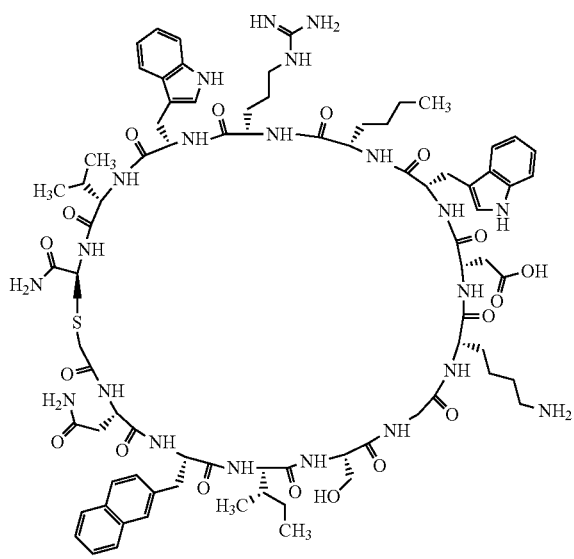
<Compound 94>
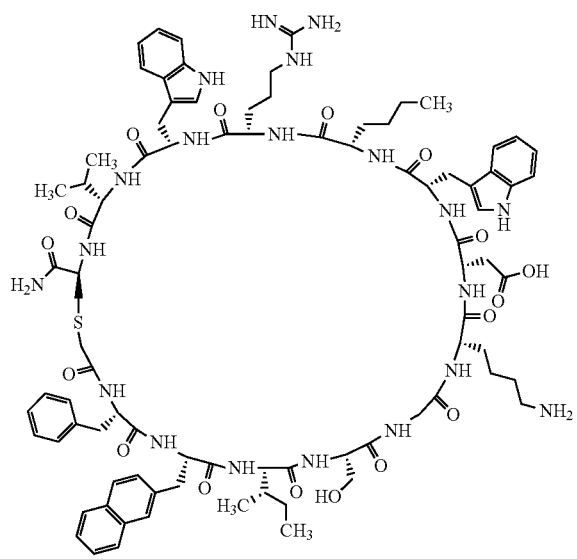
[Chem. 126]
<Compound 95>
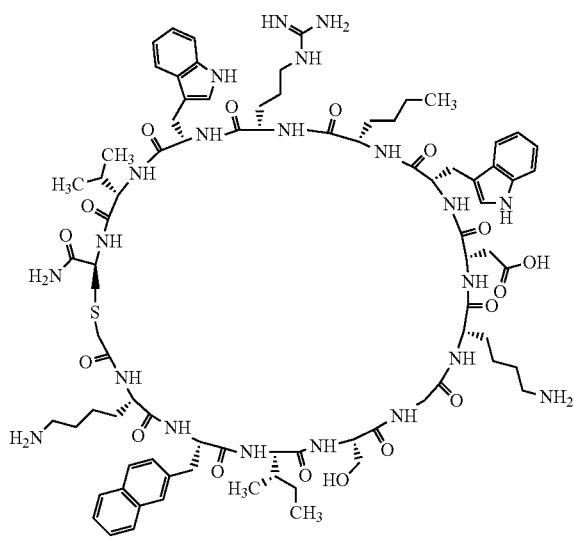
<Compound 96>
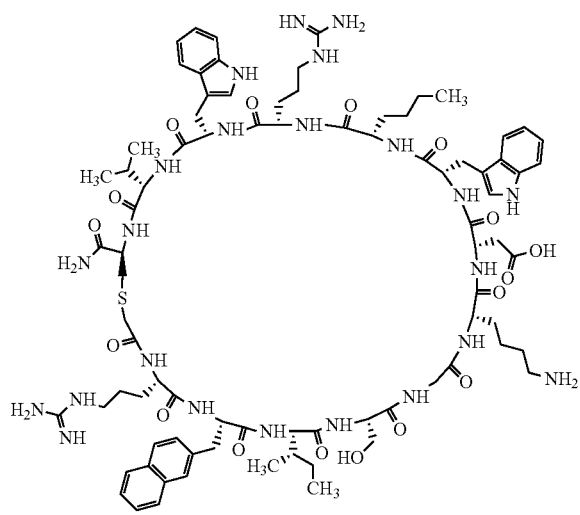

[Chem. 127]
<Compound 97>
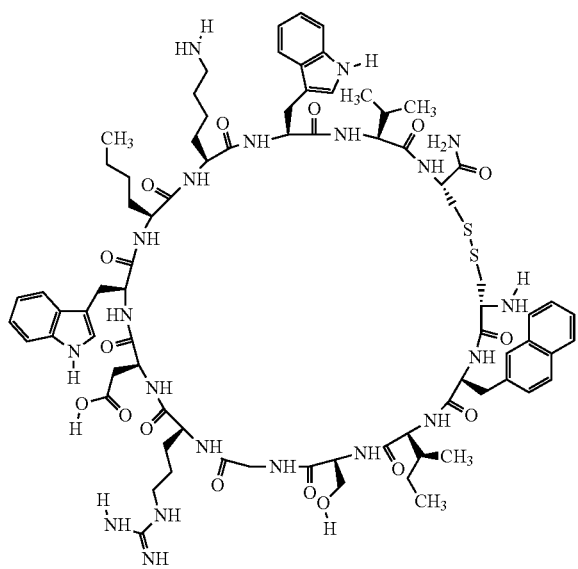
<Compound 98>
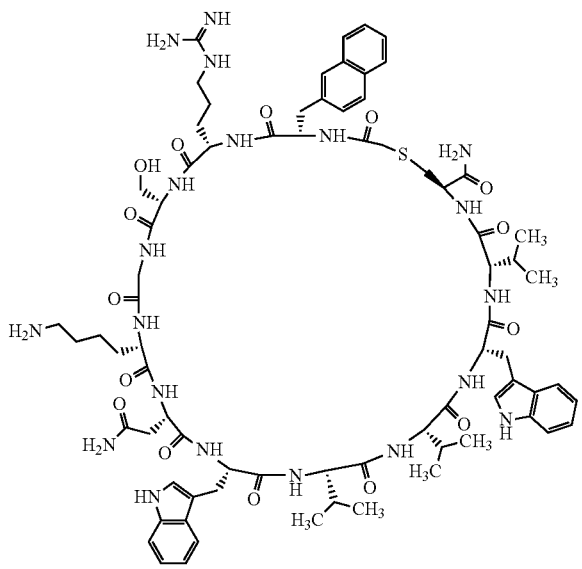
[Chem. 128]
<Compound 99>
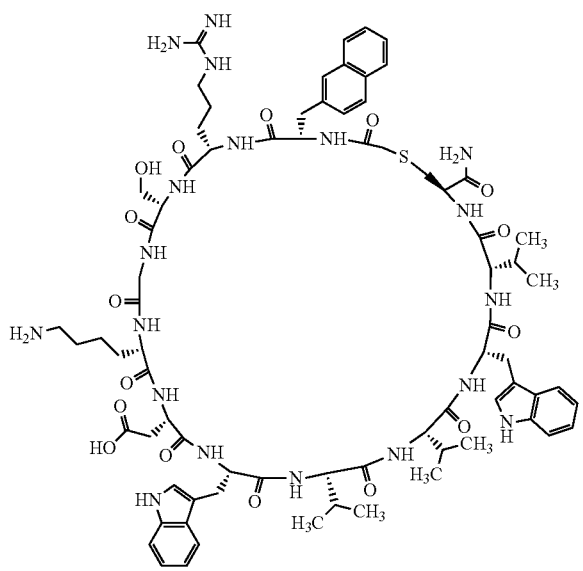
<Compound 100>
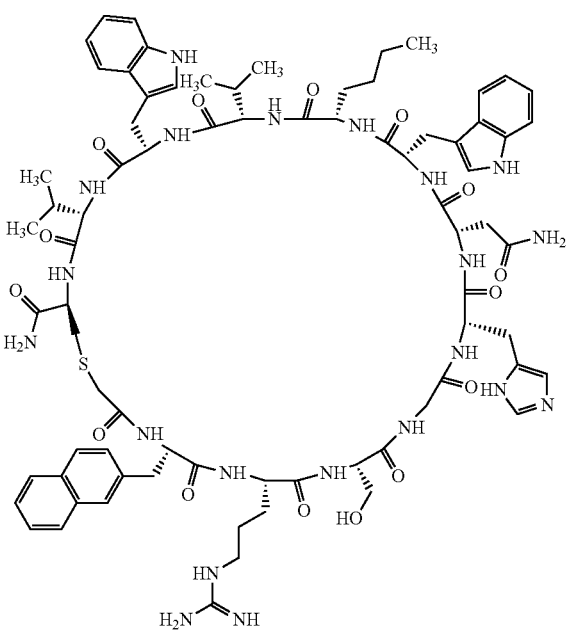

-continued

<Compound 101> <Compound 102>

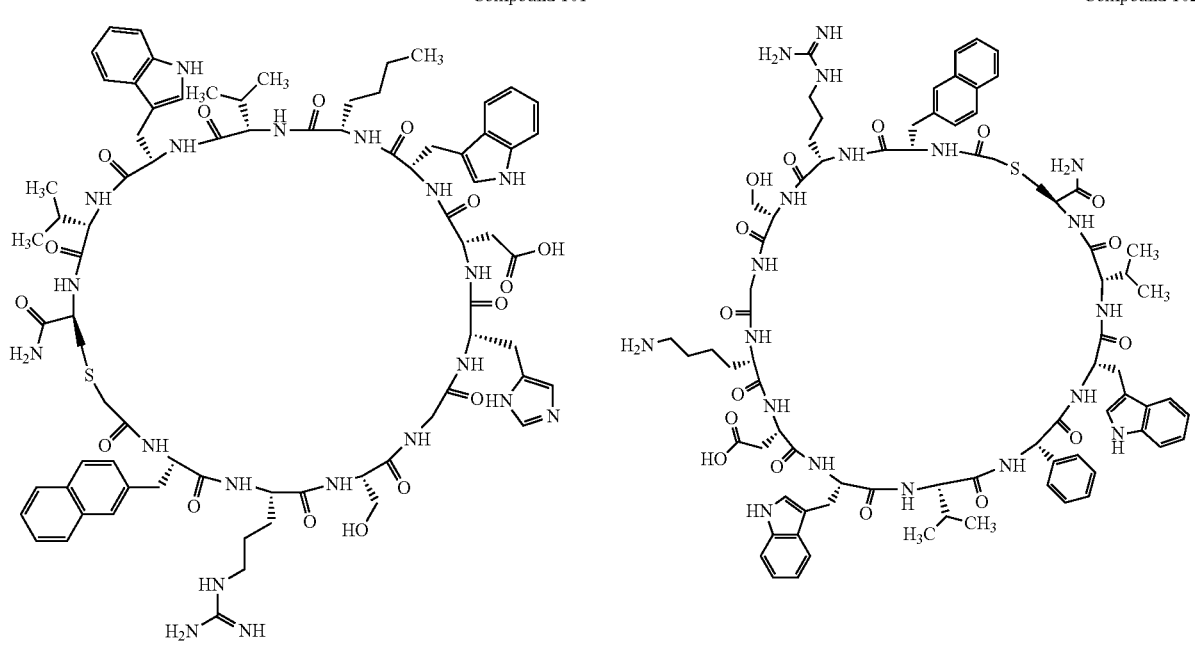

[Chem. 130]

<Compound 103> <Compound 104>

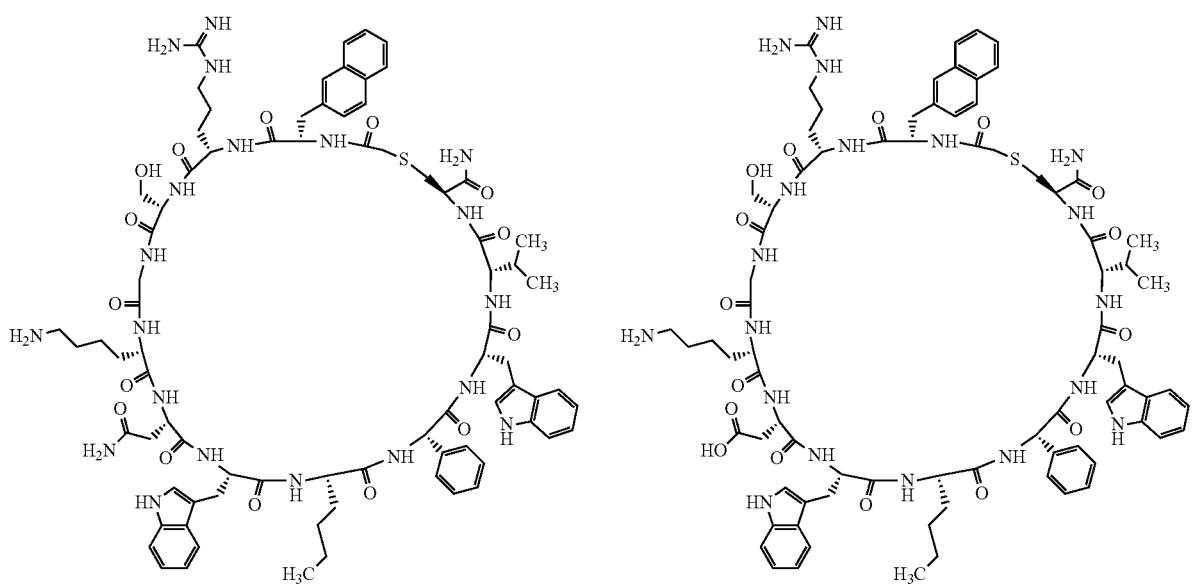

The amino acid residues constituting the macrocyclic polypeptides of Examples 1 to 104 are shown in Tables 1 to 4. The 13th amino acids as shown in these tables are each an amino acid that constitutes a linking group and whose C-terminus is converted to an amino group.

TABLE 1

| Compound | N-terminal | C-terminal | 1 | 2 | 3 | 4 | 5 | 6 | 7 | 8 | 9 | 10 | 11 | 12 | 13 | Cell adhesion IC50 (nM) | SPR hTSP1 Kd (nM) |
|---|---|---|---|---|---|---|---|---|---|---|---|---|---|---|---|---|---|
| 1 | ClAc | NH2 | F | I | S | G | R | N | W | V | V | W | V | C | 34.9 | 0.51 |
| 2 | ClAc | NH2 | F | R | S | G | R | N | W | V | V | W | V | C | 25.5 | 0.15 |

TABLE 1-continued

| Compound | N-terminal | C-terminal | 1 | 2 | 3 | 4 | 5 | 6 | 7 | 8 | 9 | 10 | 11 | 12 | 13 | Cell adhesion IC50 (nM) | SPR hTSP1 Kd (nM) |
|---|---|---|---|---|---|---|---|---|---|---|---|---|---|---|---|---|---|
| 3 | ClAc | NH2 | | F | I | S | G | R | N | W | V | K | W | V | C | 20.8 | 0.25 |
| 4 | ClAc | NH2 | | F | I | S | G | R | N | W | V | R | W | V | C | 11.2 | 0.26 |
| 5 | ClAc | NH2 | | F | I | S | G | R | N | W | V | R | W | R | C | 33.4 | 0 9 |
| 6 | ClAc | NH2 | | F | R | S | G | R | N | W | V | K | W | V | C | 27.3 | 0.44 |
| 7 | ClAc | NH2 | | F | I | S | G | K | N | W | V | K | W | V | C | 20.6 | 0.12 |
| 8 | ClAc | NH2 | | F | R | S | G | R | N | W | V | R | W | V | C | 33.4 | |
| 9 | ClAc | NH2 | | W | I | S | G | R | N | W | V | K | W | V | C | 27.3 | 0.23 |
| 10 | ClAc | NH2 | | F | I | S | G | K | N | W | V | R | W | V | C | 10.9 | 0.091 |
| 11 | ClAc | NH2 | | W | I | S | G | R | N | W | V | R | W | V | C | 26 3 | 0.14 |
| 12 | ClAc | NH2 | | F | I | T | G | R | N | W | V | K | W | V | C | 22.2 | 0.38 |
| 13 | ClAc | NH2 | | F | I | S | G | R | T | W | V | K | W | V | C | 18.7 | 0.096 |
| 14 | ClAc | NH2 | | F | I | mS | G | R | N | W | V | K | W | V | C | 21.4 | |
| 15 | ClAc | NH2 | C | F | I | S | G | R | N | W | V | K | W | V | C | 23.2 | |
| 16 | ClAc | NH2 | | W | I | S | G | K | N | W | V | K | W | V | C | 21 | |
| 17 | ClAc | NH2 | | F | I | T | G | K | N | W | V | K | W | V | C | 17.7 | |
| 18 | ClAc | NH2 | | F | I | S | G | K | T | W | V | K | W | V | C | 13 | |
| 19 | ClAc | NH2 | | F | I | S | G | K | N | W | M | K | W | V | C | 14 1 | |
| 20 | ClAc | NH2 | | W | I | S | G | K | T | W | V | K | W | V | C | 13 1 | |
| 21 | ClAc | NH2 | | F | I | S | G | K | N | W | M | R | W | V | C | 21.3 | |
| 22 | ClAc | NH2 | | W | I | S | G | K | T | W | V | R | W | V | C | 20.3 | |
| 23 | ClAc | NH2 | | W | I | S | G | R | T | W | V | K | W | V | C | 15.6 | |
| 24 | ClAc | NH2 | | 2Nal | I | S | G | R | N | W | V | K | W | V | C | 6.1 | 0.12 |
| 25 | ClAc | NH2 | | 4CF | I | S | G | R | N | W | V | K | W | V | C | 7.9 | |

TABLE 2

| | | | | | | | | | | | | | | | | | |
|---|---|---|---|---|---|---|---|---|---|---|---|---|---|---|---|---|---|
| 26 | ClAc | NH2 | | F | I | S | G | R | N | W | Nle | K | W | V | C | 7 | |
| 27 | ClAc | NH2 | 2Nal | F | | S | G | R | N | W | V | K | W | V | C | 32.8 | |
| 28 | ClAc | NH2 | 2Nal | I | | S | G | R | N | 2Nal | V | K | W | V | C | 29.4 | 0.55 |
| 29 | ClAc | NH2 | 2Nal | I | | S | G | R | N | W | V | K | 2Nal | V | C | 17.6 | |
| 30 | ClAc | NH2 | 2Nal | I | | A | G | R | N | W | V | K | W | V | C | 16.7 | |
| 31 | ClAc | NH2 | 2Nal | 4CF | | S | G | R | N | W | V | K | W | V | C | 32.5 | |
| 32 | ClAc | NH2 | 2Nal | HF | | S | G | R | N | W | V | K | W | V | C | 25.9 | |
| 33 | ClAc | NH2 | 2Nal | W | | S | G | R | N | W | V | K | W | V | C | 20.7 | |
| 34 | ClAc | NH2 | DCF | 2Nal | | S | G | R | N | W | V | K | W | V | C | 28.1 | |
| 35 | ClAc | NH2 | 2Nal | I | | S | G | R | N | 6CW | V | K | W | V | C | 26 | |
| 36 | ClAc | NH2 | 2Nal | I | | S | G | R | N | W | V | K | 6CW | V | C | 17.2 | |
| 37 | ClAc | NH2 | 2Nal | I | | S | G | R | N | W | V | K | W | HF | C | 19.6 | |
| 38 | ClAc | NH2 | 2Nal | I | | S | G | R | N | W | Nle | K | W | V | C | 9.2 | |
| 39 | ClAc | NH2 | 2Nal | I | | S | G | R | N | W | Nle | K | W | F | C | 16.3 | |
| 40 | ClAc | NH2 | 2Nal | I | | S | G | R | D | W | V | K | W | V | C | 16.1 | 0.34 |
| 41 | ClAc | NH2 | 2Nal | I | | S | G | R | N | W | V | H | W | V | C | 16.4 | 0.37 |
| 42 | ClAc | NH2 | 2Nal | I | | S | G | H | N | W | V | K | W | V | C | 32 | 0.44 |
| 43 | ClAc | NH2 | 2Nal | I | | S | G | K | N | W | V | K | W | V | C | 9.2 | 0.13 |
| 44 | ClAc | NH2 | 2Nal | I | | S | G | S | N | W | V | K | W | V | C | 30.3 | 0.58 |
| 45 | ClAc | NH2 | 2Nal | I | | S | G | R | D | W | Nle | K | W | V | C | 17.4 | 0.13 |
| 46 | ClAc | NH2 | F | I | | S | G | R | N | W | V | 3MH | W | V | C | 30.3 | |
| 47 | ClAc | NH2 | F | I | | S | G | R | N | W | V | AMF | W | V | C | 16.7 | |
| 48 | ClAc | NH2 | 2Nal | Nle | | S | G | R | N | W | V | K | W | V | C | 10.4 | |
| 49 | ClAc | NH2 | 2Nal | Phg | | S | G | R | N | W | V | K | W | V | C | 11.5 | |
| 50 | ClAc | NH2 | 2Nal | Tle | | S | G | R | N | W | V | K | W | V | C | 11.6 | |

TABLE 3

| | | | | | | | | | | | | | | | | | |
|---|---|---|---|---|---|---|---|---|---|---|---|---|---|---|---|---|---|
| 51 | ClAc | NH2 | 2Nal | I | S | G | R | N | W | Phg | K | W | V | C | 16 | | |
| 52 | ClAc | NH2 | 2Nal | I | S | G | R | N | W | V | K | W | Phg | C | 10.3 | | |
| 53 | ClAc | NH2 | 2Nal | I | S | G | R | N | W | V | K | W | Tle | C | 15.9 | | |
| 54 | ClAc | NH2 | 2Nal | I | S | G | R | N | W | V | K | W | V | Hcy | 19.5 | | |
| 55 | ClAc | NH2 | 2Nal | I | S | G | K | D | W | V | K | W | V | C | 13.7 | | |
| 56 | ClAc | NH2 | 2Nal | I | S | G | K | N | 2Nal | V | K | W | V | C | 13.2 | | |
| 57 | ClAc | NH2 | 2Nal | I | S | G | K | D | W | Nle | K | W | V | C | 15.6 | | |
| 58 | ClAc | NH2 | 2Nal | I | S | G | K | D | W | Nle | R | W | V | C | 15.9 | 0.091 | |
| 59 | ClAc | NH2 | 2Nal | I | S | G | H | N | W | Nle | K | W | V | C | 20.7 | | |
| 60 | ClAc | NH2 | 2Nal | I | S | G | R | D | W | Ahp | K | W | V | C | 21.7 | | |
| 61 | ClAc | NH2 | 2Nal | I | S | G | R | D | W | Aoc | K | W | V | C | 24.5 | | |
| 62 | ClAc | NH2 | 2Nal | I | G | G | R | D | W | Nle | K | W | V | C | 26.6 | | |
| 63 | ClAc | NH2 | 2Nal | L | S | G | R | D | W | Nle | K | W | V | C | 23.9 | | |

TABLE 3-continued

| | | | | | | | | | | | | | | | | |
|---|---|---|---|---|---|---|---|---|---|---|---|---|---|---|---|---|
| 64 | ClAc | NH2 | | 2Nal | I | S | G | K | E | W | Nle | K | W | V | C | 28.3 |
| 65 | ClAc | NH2 | | F | I | S | G | R | N | W | V | T | W | V | C | 30.6 |
| 66 | ClAc | NH2 | | F | I | S | G | K | N | W | V | S | W | V | C | 33.8 |
| 67 | ClAc | NH2 | | 2Nal | I | S | G | MS | D | W | Nle | K | W | V | C | 12.7 |
| 68 | ClAc | NH2 | | 2Nal | I | S | G | P | D | W | Nle | K | W | V | C | 28.1 |
| 69 | ClAc | NH2 | | 2Nal | I | S | G | 3Hyp | N | W | Nle | H | W | V | C | 27.9 |
| 70 | ClAc | NH2 | | 2Nal | I | S | G | MO1 | D | W | Nle | K | W | V | C | 11.9 |
| 71 | ClAc | NH2 | | 2Nal | I | S | G | MO2 | D | W | Nle | K | W | V | C | 17.1 |
| 72 | ClAc | NH2 | | 2Nal | I | S | G | Alb | D | W | Nle | K | W | V | C | 23.7 |
| 73 | ClAc | NH2 | | 2Nal | I | S | G | Cit | D | W | Nle | K | W | V | C | 15.4 |
| 74 | ClAc | NH2 | | 2Nal | I | S | G | HCt | D | W | Nle | K | W | V | C | 20.7 |
| 75 | ClAc | NH2 | G | 2Nal | I | S | G | R | D | W | Nle | K | W | V | C | 16.1 0.22 |

TABLE 4

| | | | | | | | | | | | | | | | | |
|---|---|---|---|---|---|---|---|---|---|---|---|---|---|---|---|---|
| 76 | ClAc | NH2 | G | 2Nal | I | S | G | K | D | W | Nle | R | W | V | C | 12.8 |
| 77 | ClAc | NH2 | | 2Nal | I | S | G | R | D | W | Nle | K | W | V | C(O) | 13.6 |
| 78 | ClAc | NH2 | | 2Nal | I | S | G | R | D | W | Nle | K | W | V | C(O2) | 10.7 |
| 79 | ClAc | NH2 | | 2Nal | I | S | G | R | D | W | Nle | K | W | V | Pen | 15 |
| 80 | ClAc | NH2 | A | 2Nal | I | S | G | R | D | W | Nle | K | W | V | C | 11.5 |
| 81 | ClAc | NH2 | V | 2Nal | I | S | G | R | D | W | Nle | K | W | V | C | 25.3 |
| 82 | ClAc | NH2 | L | 2Nal | I | S | G | R | D | W | Nle | K | W | V | C | 29.9 |
| 83 | ClAc | NH2 | I | 2Nal | I | S | G | R | D | W | Nle | K | W | V | C | 27.1 |
| 84 | ClAc | NH2 | M | 2Nal | I | S | G | R | D | W | Nle | K | W | V | C | 16.9 |
| 85 | ClAc | NH2 | T | 2Nal | I | S | G | R | D | W | Nle | K | W | V | C | 15.5 |
| 86 | ClAc | NH2 | Q | 2Nal | I | S | G | R | D | W | Nle | K | W | V | C | 14.2 |
| 87 | ClAc | NH2 | F | 2Nal | I | S | G | R | D | W | Nle | K | W | V | C | 15.8 |
| 88 | ClAc | NH2 | Y | 2Nal | I | S | G | R | D | W | Nle | K | W | V | C | 14.5 |
| 89 | ClAc | NH2 | W | 2Nal | I | S | G | R | D | W | Nle | K | W | V | C | 23.8 |
| 90 | ClAc | NH2 | K | 2Nal | I | S | G | R | D | W | Nle | K | W | V | C | 17.2 |
| 91 | ClAc | NH2 | H | 2Nal | I | S | G | R | D | W | Nle | K | W | V | C | 17.1 |
| 92 | ClAc | NH2 | S | 2Nal | I | S | G | K | D | W | Nle | R | W | V | C | 15.5 |
| 93 | ClAc | NH2 | N | 2Nal | I | S | G | K | D | W | Nle | R | W | V | C | 17.8 |
| 94 | ClAc | NH2 | F | 2Nal | I | S | G | K | D | W | Nle | R | W | V | C | 25.1 |
| 95 | ClAc | NH2 | K | 2Nal | I | S | G | K | D | W | Nle | R | W | V | C | 10.1 |
| 96 | ClAc | NH2 | R | 2Nal | I | S | G | K | D | W | Nle | R | W | V | C | 6.2 |
| 97 | ClAc | NH2 | C | 2Nal | I | S | G | R | D | W | Nle | K | W | V | C | 21 |
| 98 | ClAc | NH2 | | 2Nal | R | S | G | K | N | W | V | V | W | V | C | 3.9 |
| 99 | ClAc | NH2 | | 2Nal | R | S | G | K | D | W | V | V | W | V | C | 14.2 |
| 100 | ClAc | NH2 | | 2Nal | R | S | G | H | N | W | Nle | V | W | V | C | 19.5 |
| 101 | ClAc | NH2 | | 2Nal | R | S | G | H | D | W | Nle | V | W | V | C | 19.6 |
| 102 | ClAc | NH2 | | 2Nal | R | S | G | K | D | W | V | Phg | W | V | C | 9.7 |
| 103 | ClAc | NH2 | | 2Nal | R | S | G | K | N | W | Nle | Phg | W | V | C | 12.4 |
| 104 | ClAc | NH2 | | 2Nal | R | S | G | K | D | W | Nle | Phg | W | V | C | 19.8 |

As shown in Tables 5 to 7, the macrocyclic polypeptides of Examples 1 to 104 were synthesized according to any of Synthesis Procedures 1 to 5 as described below, and the acetates of some of said macrocyclic polypeptides were synthesized according to Synthesis Procedure 6. Additionally, it should be noted that the notation "Compound XXXa" refers to the acetate of Compound XXX.

TABLE 5

| Compound | MW | procedure | Yield (%) | MS type | MS measured value [M + H] | HPLC condition | Rt (min) |
|---|---|---|---|---|---|---|---|
| 1 | 1504.76 | Procedure 2 | 20 | LC-MS | 1504.76 | Condition 1 | 2.25 |
| 2 | 1547.78 | Procedure 2 | 8 | MALDI | 1547.51 | Condition 2 | 14.3 |
| 3 | 1533.80 | Procedure 2 | 11 | MALDI | 1533.52 | Condition 2 | 13.9 |
| 4 | 1561.81 | Procedure 2 | 6 | MALDI | 1561.54 | Condition 2 | 14.2 |
| 5 | 1618.86 | Procedure 2 | 7 | MALDI | 1618.61 | Condition 2 | 12.8 |
| 6 | 1576.82 | Procedure 2 | 12 | MALDI | 1576.78 | Condition 2 | 11.2 |
| 7 | 1505.78 | Procedure 2 | 17 | MALDI | 1505.72 | Condition 2 | 12.1 |
| 8 | 1604.84 | Procedure 2 | 15 | MALDI | 1604.08 | Condition 2 | 13.5 |
| 9 | 1572.83 | Procedure 2 | 13 | MALDI | 1572.19 | Condition 2 | 14 |
| 10 | 1533.80 | Procedure 2 | 6 | MALDI | 1533.04 | Condition 2 | 14.4 |
| 11 | 1600.85 | Procedure 2 | 12 | MALDI | 1600.04 | Condition 2 | 14.1 |
| 12 | 1547.82 | Procedure 2 | 6 | MALDI | 1547.17 | Condition 2 | 14.6 |
| 13 | 1520.80 | Procedure 2 | 12 | MALDI | 1520.71 | Condition 2 | 12.6 |
| 14 | 1547.82 | Procedure 2 | 9 | MALDI | 1547.58 | Condition 3 | 5.74 |
| 15 | 1594.90 | Procedure 1 | 14 | MALDI | 1594.72 | Condition 4 | 7.46 |

TABLE 5-continued

| Compound | MW | procedure | Yield (%) | MS type | MS measured value [M + H] | HPLC condition | Rt (min) |
|---|---|---|---|---|---|---|---|
| 16 | 1544.82 | Procedure 2 | 20 | MALDI | 1544.75 | Condition 3 | 5.05 |
| 17 | 1519.81 | Procedure 2 | 35 | MALDI | 1519.74 | Condition 3 | 5.59 |
| 18 | 1492.78 | Procedure 2 | 20 | MALDI | 1492.73 | Condition 3 | 5.62 |
| 19 | 1537.85 | Procedure 2 | 24 | MALDI | 1537.71 | Condition 3 | 5.65 |
| 20 | 1531.82 | Procedure 2 | 18 | MALDI | 1531.72 | Condition 3 | 5.35 |
| 21 | 1565.86 | Procedure 2 | 27 | MALDI | 1565.7 | Condition 3 | 5.81 |
| 22 | 1559.83 | Procedure 2 | 15 | MALDI | 1559.8 | Condition 3 | 5.54 |
| 23 | 1559.83 | Procedure 2 | 19 | MALDI | 1559.7 | Condition 3 | 5.48 |
| 24 | 1583.86 | Procedure 3 | 32 | MALDI | 1583.56 | Condition 2 | 12.9 |
| 25 | 1568.24 | Procedure 3 | 23 | MALDI | 1567.52 | Condition 2 | 12.9 |
| 26 | 1547.82 | Procedure 3 | 24 | MALDI | 1547.49 | Condition 2 | 12.9 |
| 27 | 1617.87 | Procedure 2 | 17 | MALDI | 1617.78 | Condition 3 | 6.4 |
| 28 | 1594.88 | Procedure 2 | 20 | MALDI | 1594.73 | Condition 3 | 6.2 |
| 29 | 1594.88 | Procedure 2 | 24 | MALDI | 1594.73 | Condition 3 | 6.3 |
| 30 | 1567.86 | Procedure 2 | 21 | MALDI | 1567.74 | Condition 3 | 6.4 |
| 31 | 1652.32 | Procedure 2 | 20 | LC-MS | 1596.82 | Condition 1 | 2.15 |
| 32 | 1631.90 | Procedure 2 | 16 | LC-MS | 1568.91 | Condition 1 | 2.09 |
| 33 | 1656.91 | Procedure 2 | 18 | LC-MS | 1540.81 | Condition 1 | 2.09 |
| 34 | 1686.76 | Procedure 2 | 20 | LC-MS | 1615.8 | Condition 1 | 2.19 |
| 35 | 1618.30 | Procedure 2 | 12 | LC-MS | 1646.81 | Condition 1 | 2.05 |
| 36 | 1618.30 | Procedure 2 | 23 | LC-MS | 1617.75 | Condition 1 | 2.08 |
| 37 | 1645.92 | Procedure 2 | 22 | LC-MS | 1646.81 | Condition 1 | 2.17 |
| 38 | 1597.88 | Procedure 2 | 26 | LC-MS | 1597.8 | Condition 1 | 2.05 |
| 39 | 1645.92 | Procedure 2 | 25 | LC-MS | 1646.81 | Condition 1 | 2.21 |
| 40 | 1584.84 | Procedure 2 | 33 | LC-MS | 1585.78 | Condition 1 | 1.63 |
| 41 | 1592.82 | Procedure 2 | 21 | LC-MS | 1592.75 | Condition 1 | 1.65 |
| 42 | 1564.81 | Procedure 2 | 22 | LC-MS | 1564.75 | Condition 1 | 2 |
| 43 | 1555.84 | Procedure 2 | 23 | LC-MS | 1555.78 | Condition 1 | 1.99 |
| 44 | 1514.75 | Procedure 2 | 19 | LC-MS | 1514.72 | Condition 1 | 2.08 |

TABLE 6

| Compound | MW | procedure | Yield (%) | MS type | MS measured value [M + H] | HPLC condition | Rt (min) |
|---|---|---|---|---|---|---|---|
| 45 | 1598.87 | Procedure 2 | 19 | MALDI | 1598.78 | Condition 3 | 6.35 |
| 46 | 1556.79 | Procedure 2 | 8 | LC-MS | 1556.76 | Condition 1 | 1.95 |
| 47 | 1581.84 | Procedure 2 | 28 | LC-MS | 1581.79 | Condition 1 | 1.95 |
| 48 | 1583.86 | Procedure 2 | 28 | LC-MS | 1583.8 | Condition 1 | 2.03 |
| 49 | 1603.85 | Procedure 2 | 21 | LC-MS | 1603.77 | Condition 1 | 2.01 |
| 50 | 1583.86 | Procedure 2 | 22 | LC-MS | 1583.79 | Condition 1 | 1.99 |
| 51 | 1617.87 | Procedure 2 | 19 | LC-MS | 1617.79 | Condition 1 | 2.01 |
| 52 | 1617.87 | Procedure 2 | 20 | LC-MS | 1617.78 | Condition 1 | 2.09 |
| 53 | 1597.88 | Procedure 2 | 17 | LC-MS | 1597.81 | Condition 1 | 2.03 |
| 54 | 1597.88 | Procedure 2 | 12 | LC-MS | 1597.83 | Condition 1 | 2.05 |
| 55 | 1556.83 | Procedure 2 | 22 | MALDI | 1556.74 | Condition 3 | 5 |
| 56 | 1566.86 | Procedure 2 | 26 | LC-MS | 1566.8 | Condition 1 | 2.22 |
| 57 | 1570.85 | Procedure 2 | 25 | LC-MS | 1570.79 | Condition 3 | 5.18 |
| 58 | 1598.87 | Procedure 2 | 20 | LC-MS | 1598.79 | Condition 3 | 5.31 |
| 59 | 1578.84 | Procedure 2 | 20 | LC-MS | 1578.77 | Condition 3 | 5.18 |
| 60 | 1612.89 | Procedure 2 | 26 | LC-MS | 1612.81 | Condition 1 | 2.13 |
| 61 | 1626.92 | Procedure 2 | 23 | LC-MS | 1626.83 | Condition 1 | 2.18 |
| 62 | 1568.84 | Procedure 2 | 26 | LC-MS | 1568.78 | Condition 1 | 1.71 |
| 63 | 1598.87 | Procedure 2 | 13 | LC-MS | 1598.79 | Condition 1 | 1.74 |
| 64 | 1584.88 | Procedure 2 | 8 | LC-MS | 1584.8 | Condition 1 | 1.72 |
| 65 | 1506.74 | Procedure 2 | 13 | LC-MS | 1506.73 | Condition 1 | 1.68 |
| 66 | 1464.69 | Procedure 2 | 18 | LC-MS | 1464.71 | Condition 1 | 1.66 |
| 67 | 1543.79 | Procedure 1 | 14 | LC-MS | 1543.74 | Condition 1 | 2.19 |
| 68 | 1539.80 | Procedure 1 | 16 | LC-MS | 1539.74 | Condition 1 | 2.2 |
| 69 | 1563.78 | Procedure 1 | 3 | LC-MS | 1563.72 | Condition 1 | 2.17 |
| 70 | 1589.88 | Procedure 1 | 10 | LC-MS | 1589.73 | Condition 1 | 2.15 |
| 71 | 1605.88 | Procedure 1 | 12 | LC-MS | 1605.72 | Condition 1 | 2.2 |
| 72 | 1571.80 | Procedure 1 | 15 | LC-MS | 1571.75 | Condition 1 | 2.15 |
| 73 | 1599.85 | Procedure 1 | 12 | LC-MS | 1599.78 | Condition 1 | 2.13 |
| 74 | 1613.88 | Procedure 1 | 14 | LC-MS | 1613.79 | Condition 1 | 2.14 |
| 75 | 1655.92 | Procedure 3 | 9 | LC-MS | 1656.83 | Condition 1 | 2.21 |
| 76 | 1655.92 | Procedure 3 | 9 | LC-MS | 1656.83 | Condition 1 | 2.06 |
| 77 | 1614.87 | Procedure 4 | 25 | LC-MS | 1614.79 | Condition 1 | 1.78 |
| 78 | 1630.87 | Procedure 5 | 34 | LC-MS | 1631.79 | Condition 1 | 1.71 |
| 79 | 1626.92 | Procedure 3 | 9 | LC-MS | 1627.83 | Condition 1 | 1.8 |
| 80 | 1669.94 | Procedure 2 | 19 | LC-MS | 1669.83 | Condition 1 | 2.13 |

TABLE 6-continued

| Compound | MW | procedure | Yield (%) | MS type | MS measured value [M + H] | HPLC condition | Rt (min) |
|---|---|---|---|---|---|---|---|
| 81 | 1698.00 | Procedure 2 | 12 | LC-MS | 1697.86 | Condition 1 | 2.17 |
| 82 | 1712.02 | Procedure 2 | 20 | LC-MS | 1711.88 | Condition 1 | 2.23 |
| 83 | 1712.02 | Procedure 2 | 18 | LC-MS | 1711.88 | Condition 1 | 2.21 |
| 84 | 1730.06 | Procedure 2 | 13 | LC-MS | 1729.83 | Condition 1 | 2.16 |
| 85 | 1699.97 | Procedure 2 | 13 | LC-MS | 1699.84 | Condition 1 | 2.09 |
| 86 | 1727.00 | Procedure 2 | 12 | LC-MS | 1726.85 | Condition 1 | 2.07 |
| 87 | 1746.04 | Procedure 2 | 13 | LC-MS | 1745.86 | Condition 1 | 2.19 |
| 88 | 1762.04 | Procedure 2 | 10 | LC-MS | 1761.86 | Condition 1 | 2.09 |

TABLE 7

| Compound | MW | procedure | Yield (%) | MS type | MS measured value [M + H] | HPLC condition | Rt (min) |
|---|---|---|---|---|---|---|---|
| 89 | 1785.08 | Procedure 2 | 10 | LC-MS | 1784.87 | Condition 1 | 2.18 |
| 90 | 1727.04 | Procedure 2 | 7 | LC-MS | 1726.89 | Condition 1 | 2 |
| 91 | 1736.01 | Procedure 2 | 13 | LC-MS | 1735.85 | Condition 1 | 1.95 |
| 92 | 1685.94 | Procedure 2 | 18 | LC-MS | 1685.83 | Condition 1 | 2.1 |
| 93 | 1712.97 | Procedure 2 | 15 | LC-MS | 1712.84 | Condition 1 | 2.11 |
| 94 | 1746.04 | Procedure 2 | 20 | LC-MS | 1745.86 | Condition 1 | 2.18 |
| 95 | 1727.04 | Procedure 2 | 17 | LC-MS | 1726.89 | Condition 1 | 1.98 |
| 96 | 1755.05 | Procedure 2 | 7 | LC-MS | 1754.89 | Condition 1 | 1.99 |
| 97 | 1659.97 | Procedure 1 | 26 | LC-MS | 1660.79 | Condition 1 | 2.18 |
| 98 | 1569.83 | Procedure 2 | 16 | LC-MS | 1569.78 | Condition 1 | 1.64 |
| 99 | 1570.81 | Procedure 2 | 15 | LC-MS | 1570.76 | Condition 1 | 1.66 |
| 100 | 1592.82 | Procedure 2 | 21 | LC-MS | 1592.75 | Condition 1 | 1.71 |
| 101 | 1593.81 | Procedure 2 | 26 | LC-MS | 1593.74 | Condition 1 | 1.72 |
| 102 | 1604.83 | Procedure 1 | 19 | LC-MS | 1604.75 | Condition 1 | 1.7 |
| 103 | 1617.87 | Procedure 1 | 19 | LC-MS | 1617.78 | Condition 1 | 1.72 |
| 104 | 1618.86 | Procedure 1 | 21 | LC-MS | 1618.77 | Condition 1 | 1.74 |
| 45a | 1598.87 | Procedure 6 | 19 | LC-MS | 1598.79 | Condition 1 | 2.11 |
| 58a | 1598.87 | Procedure 6 | 20 | LC-MS | 1598.79 | Condition 1 | 1.7 |
| 98a | 1569.83 | Procedure 6 | 25 | LC-MS | 1569.78 | Condition 1 | 1.63 |
| 99a | 1570.81 | Procedure 6 | 24 | LC-MS | 1570.77 | Condition 1 | 1.66 |
| 100a | 1592.82 | Procedure 6 | 21 | LC-MS | 1592.77 | Condition 1 | 1.72 |
| 101a | 1593.81 | Procedure 6 | 26 | LC-MS | 1593.75 | Condition 1 | 1.74 |
| 102a | 1604.83 | Procedure 6 | 19 | LC-MS | 1604.75 | Condition 1 | 1.68 |
| 103a | 1617.87 | Procedure 6 | 19 | LC-MS | 1617.79 | Condition 1 | 1.69 |
| 104a | 1618.86 | Procedure 6 | 21 | LC-MS | 1618.76 | Condition 1 | 1.74 |

Synthesis Procedure 1

This procedure was carried out using the automatic synthesizer Syro II (produced by Biotage Japan) according to a common solid-phase synthesis method using a 9-fluorenylmethoxycarbonyl group (Fmoc group) as an α-amino group-protecting group.

The equivalent of 88 μmol of Rink Amide Resin AM (produced by Novaviochem) was added to a reaction vessel, and amino acids were coupled in 1-methyl-2-pyrrolidinone in a stepwise manner by following 1) and 2) described below.

I) Cys and His: 3 equivalents each of N,N-diisopropylcarbodiimide, 1-hydroxy-7-azabenzotriazole (HOAt), and an Fmoc group-protected amino acid were added and reacted together.

2) Other amino acids: 3 equivalents each of O-(7-azabenzotriazol-1-yl)-N,N,N',N'-tetramethyluronium hexafluorophosphate (HATU), N,N-diisopropylamine, and an Fmoc group-protected amino acid were added and reacted together.

Removal of Fmoc groups was carried out using 20% piperidine/1-methyl-2-pyrrolidinone.

After the N-terminal amino acid was coupled and the Fmoc group of this amino acid was removed, 3 equivalents each of N,N-diisopropylcarbodiimide, 1-hydroxy-7-azabenzotriazole (HOAt), and chloroacetic acid were added and reacted together in 1-methyl-2-pyrrolidinone.

A produced peptide resin was washed three times with 1-methyl-2-pyrrolidinone and three times with dichloromethane, followed by drying. 2 mL of trifluoroacetic acid/ethanedithiol/triisopropylsilane/water (92.5:2.5:2.5:2.5 by volume) was added, and the mixture was stirred at room temperature for 3 hours.

A crude peptide cleaved was recovered by ether precipitation, washed twice with tert-butyl methyl ether, dried, and then dissolved in dimethylsulfoxide (8 mL). After addition of n-propylamine (80 μL), the mixture was left to stand overnight. Further, after addition of acetic acid (80 μL), the reaction solution was concentrated using V10 (produced by Biotage Japan) and purified by reverse-phase high performance liquid chromatography using Kinetex 5u XB-C18 (150×21.2 mm, produced by Phenomenex) to afford the product of interest. The mobile phase used was water/acetonitrile containing 0.1% trifluoroacetic acid. A fraction of the product of interest was lyophilized to yield the product of interest as a trifluoroacetic acid salt.

Synthesis Procedure 2

After a fraction of the product of interest was lyophilized by following Synthesis Procedure 1, the lyophilized fraction was dissolved in 0.1 N hydrochloric acid/acetonitrile and lyophilized again to yield the product of interest as a hydrochloric acid salt.

Synthesis Procedure 3

This procedure was carried out using the automatic synthesizer Liberty Blue (produced by CEM) according to a common solid-phase synthesis method using a 9-fluorenylmethoxycarbonyl group (Fmoc group) as an α-amino group-protecting group.

The equivalent of 100 μmol of Rink Amide Resin AM (produced by Novaviochem) was added to a reaction vessel, and amino acids were coupled in a stepwise manner by adding and reacting 5 equivalents each of N,N-diisopropylcarbodiimide, ethyl cyano(hydroxyimino)acetate, and an Fmoc group-protected amino acid in N,N-dimethylformamide.

Removal of Fmoc groups was carried out using 20% piperidine/N,N-dimethylformamide.

After the N-terminal amino acid was coupled and the Fmoc group of this amino acid was removed, 5 equivalents each of N,N-diisopropylcarbodiimide, ethyl cyano(hydroxyimino)acetate, and chloroacetic acid were added and reacted together in N,N-dimethylformamide.

A produced peptide resin was washed three times with N,N-dimethylformamide and three times with dichloromethane, followed by drying. 2 mL of trifluoroacetic acid/ethanedithiol/triisopropylsilane/water (92.5:2.5:2.5:2.5 by volume) was added, and the mixture was stirred at room temperature for 3 hours.

A crude peptide cleaved was recovered by ether precipitation, washed twice with tert-butyl methyl ether, dried, and then dissolved in dimethylsulfoxide (8 mL). After addition of n-propylamine (80 μL), the mixture was left to stand overnight. Further, after addition of acetic acid (80 μL), the reaction solution was concentrated using V10 (produced by Biotage Japan) and purified by reverse-phase high performance liquid chromatography using Kinetex 5u XB-C18 (150×21.2 mm, produced by Phenomenex) to afford the product of interest. The mobile phase used was water/acetonitrile containing 0.1% trifluoroacetic acid. After a fraction of the product of interest was lyophilized, the lyophilized fraction was dissolved in 0.1 N hydrochloric acid/acetonitrile and lyophilized again to yield the product of interest as a hydrochloric acid salt.

Synthesis Procedure 4

The hydrochloric acid salt of macrocyclic polypeptide (40.0 mg, 24 μmol) obtained by Synthesis Procedure 2 was dissolved in acetonitrile (5 mL) and an aqueous 50 mM ammonium bicarbonate solution (5 mL). 64 μL (24 μmol) of 100 mg/mL of m-chloroperbenzoic acid in acetonitrile was added, and the mixture was stirred and left to stand at room temperature. After 2 hours, another 15 μL (6 μmop of the same solution was added, and the mixture was left to stand for 1 hour. The reaction solution was purified by reverse-phase high performance liquid chromatography using Kinetex 5u XB-C18 (150×21.2 mm, produced by Phenomenex) to afford the product of interest. The mobile phase used was water/acetonitrile containing 0.1% trifluoroacetic acid. A fraction of the product of interest was lyophilized to yield the product of interest as a trifluoroacetic acid salt.

Synthesis Procedure 5

The hydrochloric acid salt of macrocyclic polypeptide (40.0 mg, 24 μmol) obtained by Synthesis Procedure 2 was dissolved in acetonitrile (5 mL) and an aqueous 50 mM ammonium bicarbonate solution (5 mL). 127 μL (48 μmol) of 100 mg/mL of m-chloroperbenzoic acid in acetonitrile was added, and the mixture was stirred and left to stand at room temperature. After 2 hours, another 64 μL (24 μmol) of the same solution was added, and the mixture was left to stand for 1 hour. The reaction solution was purified by reverse-phase high performance liquid chromatography using Kinetex 5u XB-C18 (150×21.2 mm, produced by Phenomenex) to afford the product of interest. The mobile phase used was water/acetonitrile containing 0.1% trifluoroacetic acid. A fraction of the product of interest was lyophilized to yield the product of interest as a trifluoroacetic acid salt.

Synthesis Procedure 6

The trifluoroacetic acid salt of product of interest obtained by Synthesis Procedure 1, or the hydrochloric acid salt of product of interest obtained by Synthesis Procedure 2, was dissolved in an aqueous 10% acetonitrile solution (5-10 mM). 50 equivalents of Dowex™ (1×8 100-200 mesh, 1.2 meq/mL, produced by Wako Pure Chemical Industries, Ltd.), which had been subjected to substitution by acetate ion in advance, was added, and the mixture was shaken for 2 hours. After filtration, the filtrate was lyophilized to yield the product of interest as an acetic acid salt.

Tables 8 and 9 show the natural amino acid reagents that were used to synthesize the macrocyclic polypeptides of Examples 1 to 104. Tables 10 to 12 show the non-natural amino acid reagents that were used, or are usable, to synthesize the macrocyclic polypeptides of Examples 1 to 104, and their suppliers.

TABLE 8

| Abbrev. | Structural formula |
|---|---|
| Fmoc-Ala-OH | |

TABLE 8-continued
| Abbrev. | Structural formula |
|---|---|
| Fmoc-Asn(Trt)-OH | 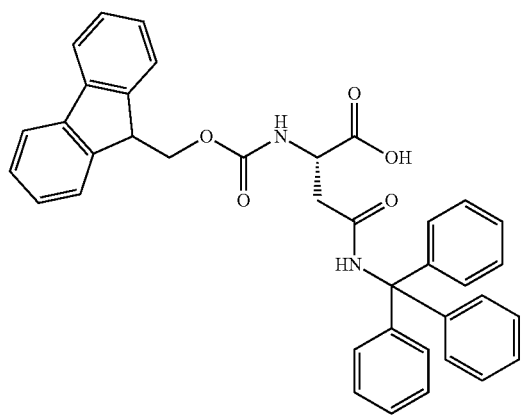 [SMILES: O=C(C[C@H](NC(=O)OCC1c2ccccc2-c2ccccc21)C(=O)O)NC(c1ccccc1)(c1ccccc1)c1ccccc1] |
| Fmoc-Asp(tBu)-OH | 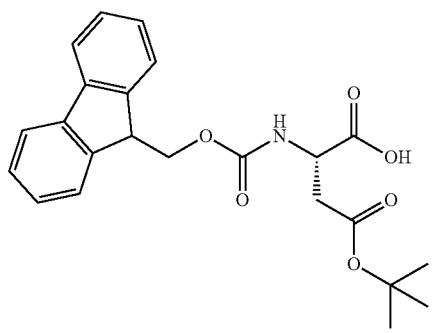 [SMILES: CC(C)(C)OC(=O)C[C@H](NC(=O)OCC1c2ccccc2-c2ccccc21)C(=O)O] |
| Fmoc-Arg(Pbf)-OH | 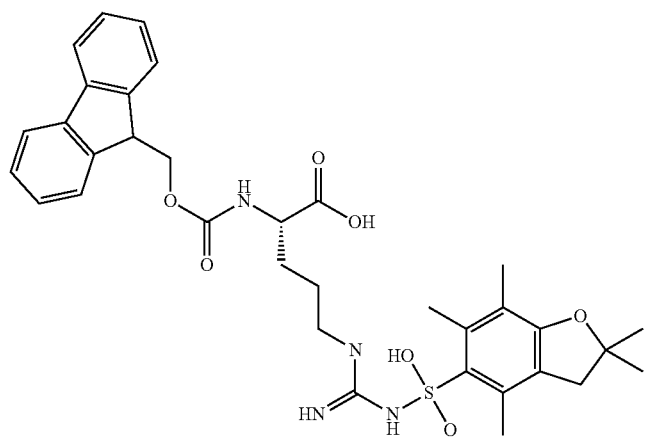 [SMILES: Cc1c(C)c(S(O)(O)NC(=N)NCCC[C@H](NC(=O)OCC2c3ccccc3-c3ccccc32)C(=O)O)c(C)c2c1OC(C)(C)C2] |
| Fmoc-Cys(Trt)-OH | 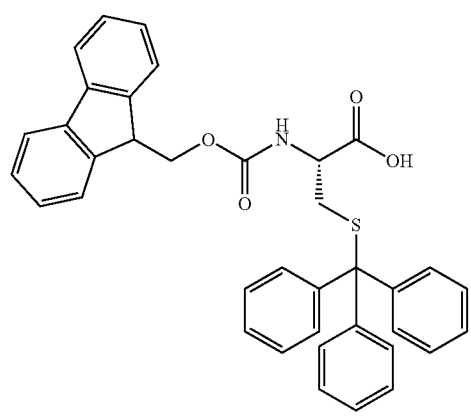 [SMILES: O=C(N[C@@H](CSC(c1ccccc1)(c1ccccc1)c1ccccc1)C(=O)O)OCC1c2ccccc2-c2ccccc21] |

TABLE 8-continued
| Abbrev. | Structural formula |
|---|---|
| Fmoc-Gln(Trt)-OH | 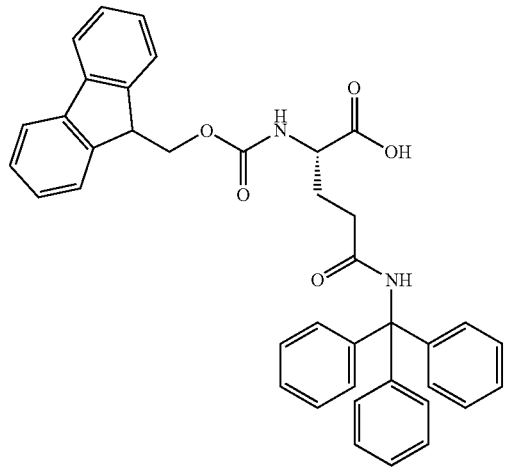 [SMILES: O=C(CC[C@H](NC(=O)OCC1c2ccccc2-c2ccccc21)C(=O)O)NC(c1ccccc1)(c1ccccc1)c1ccccc1] |
| Fmoc-Glu(tBu)-OH | 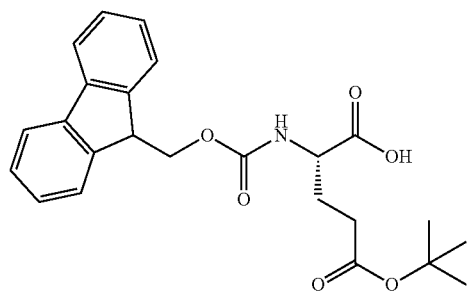 [SMILES: CC(C)(C)OC(=O)CC[C@H](NC(=O)OCC1c2ccccc2-c2ccccc21)C(=O)O] |
| Fmoc-Gly-OH | 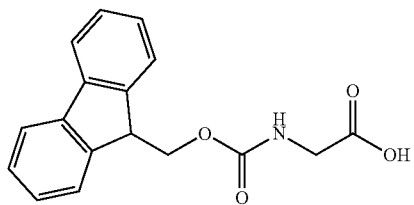 [SMILES: O=C(O)CNC(=O)OCC1c2ccccc2-c2ccccc21] |
| Fmoc-His(Trt)-OH | 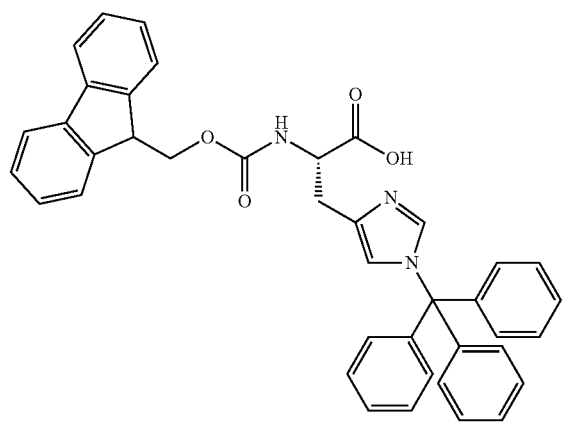 [SMILES: O=C(N[C@@H](Cc1cn(C(c2ccccc2)(c2ccccc2)c2ccccc2)cn1)C(=O)O)OCC1c2ccccc2-c2ccccc21] |

TABLE 8-continued
| Abbrev. | Structural formula |
|---|---|
| Fmoc-Ile-OH | 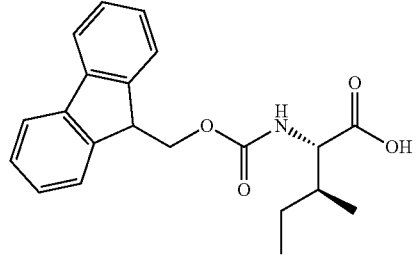 [SMILES: CC[C@H](C)[C@H](NC(=O)OCC1c2ccccc2-c2ccccc21)C(=O)O] |
TABLE 9
| Abbrev. | Structural formula |
|---|---|
| Fmoc-Leu-OH | 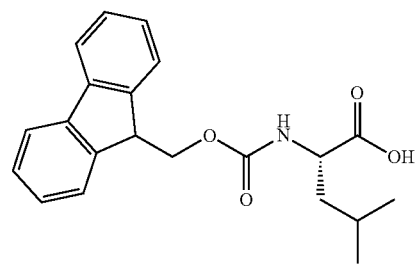 [SMILES: CC(C)C[C@H](NC(=O)OCC1c2ccccc2-c2ccccc21)C(=O)O] |
| Fmo-Lys(Boc)-OH | 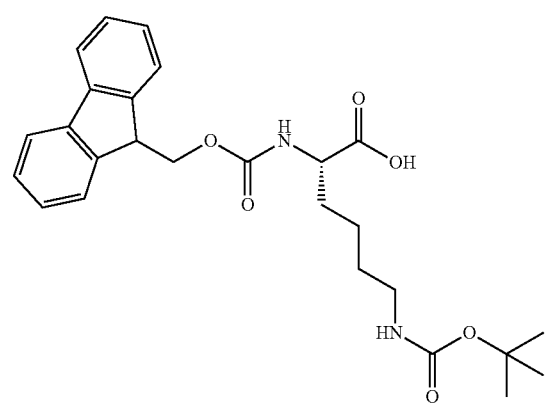 [SMILES: CC(C)(C)OC(=O)NCCCC[C@H](NC(=O)OCC1c2ccccc2-c2ccccc21)C(=O)O] |
| Fmoc-Met-OH | 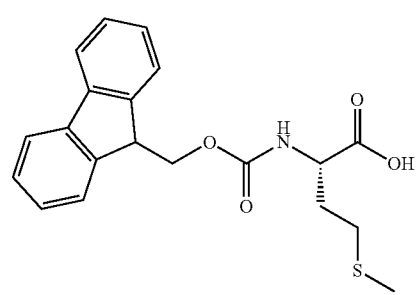 |

TABLE 9-continued
| Abbrev. | Structural formula |
|---|---|
| Fcmo-Phe-OH | 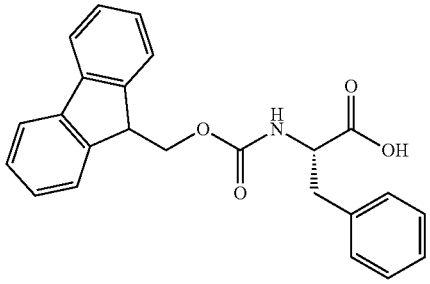 [SMILES: O=C(N[C@@H](Cc1ccccc1)C(=O)O)OCC1c2ccccc2-c2ccccc21] |
| Fmoc-Pro-OH | 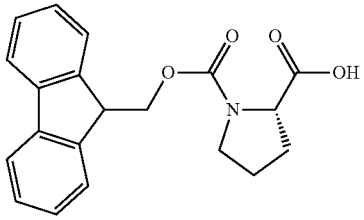 [SMILES: O=C(O)[C@@H]1CCCN1C(=O)OCC1c2ccccc2-c2ccccc21] |
| Fmoc-Ser(tBu)-OH | 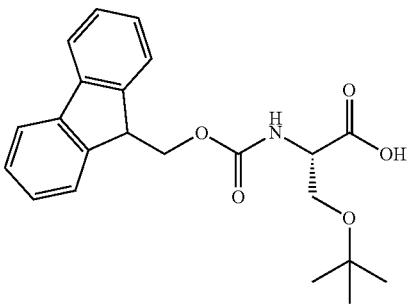 [SMILES: CC(C)(C)OC[C@H](NC(=O)OCC1c2ccccc2-c2ccccc21)C(=O)O] |
| Fmoc-Thr(tBu)-OH | 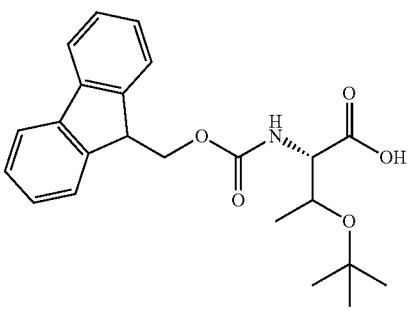 [SMILES: CC(OC(C)(C)C)[C@H](NC(=O)OCC1c2ccccc2-c2ccccc21)C(=O)O] |
| Fmoc-Trp(Boc)-OH | 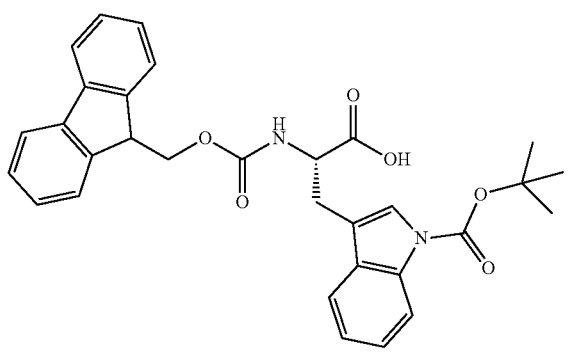 [SMILES: CC(C)(C)OC(=O)n1cc(C[C@H](NC(=O)OCC2c3ccccc3-c3ccccc32)C(=O)O)c2ccccc21] |

TABLE 9-continued

| Abbrev. | Structural formula |
|---|---|
| Fmoc-Tyr(tBu)-OH | |
| Fmoc-Val-OH | |

TABLE 10

| Abbrev. | Structural formula | Manufacturer | Cat. No. |
|---|---|---|---|
| $^m$S | | NOVABIO | 852289 |
| 2Nal | | COMBI-BLOCKS | SS-0101 |
| 4CF | | SIGMAALDRICH | 47424-5G |

TABLE 10-continued

| Abbrev. | Structural formula | Manufacturer | Cat. No. |
|---|---|---|---|
| Nle | | COMBI-BLOCKS | SS-9964 |
| DCF | | WATANABE | M00568-5G |
| 6CW | | WATANABE | M02602 |
| HF | | WATANABE | L00558-5G |

TABLE 10-continued

| Abbrev. | Structural formula | Manufacturer | Cat. No. |
|---|---|---|---|
| 3MH | | NOVAVIO | 852286 |
| AMF | | CHEM-IMPEX | 7408 |

TABLE 11

| Abbrev. | Structural formula | Manufacturer | Cat. No. |
|---|---|---|---|
| Phg | | ANASPEC | 21072 |
| Tle | | ANASPEC | 21070 |

TABLE 11-continued
| Abbrev. | Structural formula | Manufacturer | Cat. No. |
|---|---|---|---|
| Hcy | 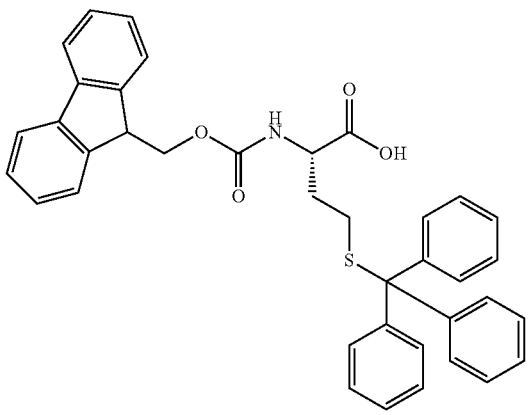 [SMILES: O=C(N[C@@H](CCSC(c1ccccc1)(c1ccccc1)c1ccccc1)C(=O)O)OCC1c2ccccc2-c2ccccc21] | CHEM-IMPEX | 05723 |
| Ahp | 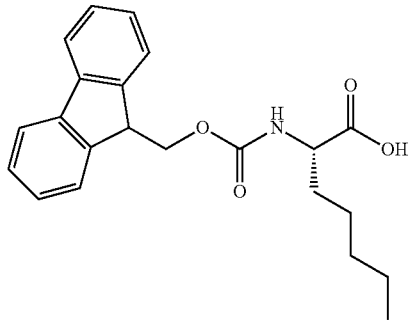 [SMILES: CCCCC[C@H](NC(=O)OCC1c2ccccc2-c2ccccc21)C(=O)O] | WATANABE | M01985-1G |
| Aoc | 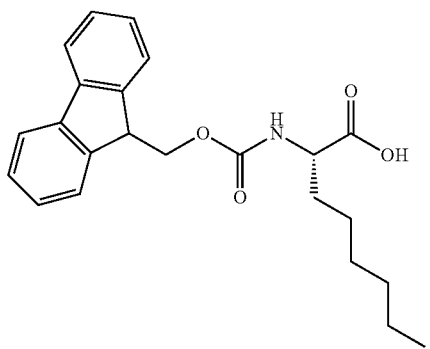 [SMILES: CCCCCC[C@H](NC(=O)OCC1c2ccccc2-c2ccccc21)C(=O)O] | WATANABE | M00837-1G |
| MS | 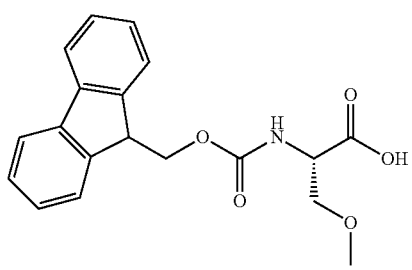 [SMILES: COC[C@H](NC(=O)OCC1c2ccccc2-c2ccccc21)C(=O)O] | WATANABE | K00945-5G |

TABLE 11-continued

| Abbrev. | Structural formula | Manufacturer | Cat. No. |
|---------|-------------------|--------------|----------|
| 3Hyp |  | WATANABE | K00438-5G |
| MO1 |  | COMBI-BLOCKS | SS-0372 |
| MO2 |  | CHEM-IMPEX | 03725 |

TABLE 12

| Abbrev. | Structural formula | Manufacturer | Cat. No. |
|---------|-------------------|--------------|----------|
| Alb |  | WATANABE | M02521-5G |

TABLE 12-continued

| Abbrev. | Structural formula | Manufacturer | Cat. No. |
|---|---|---|---|
| Cit | | WATANABE | M00443 |
| HCt | | COMBI-BLOCKS | SS-0910 |
| Pen | | WATANABE | M00636-5G |
| Alg | | WATANABE | M01125-5G |

TABLE 12-continued

| Abbrev. | Structural formula | Manufacturer | Cat. No. |
|---|---|---|---|
| Btg | (Fmoc-protected amino acid with allyl side chain) | ARKPHARMINC | AK102989 |

Tables 5 to 7 show the HPLC conditions and retention times used to purify the different macrocyclic polypeptides. HPLC conditions 1 to 4 are as detailed below.

HPLC Condition 1
Column: Kinetex 1.7u XB-C18 (50×2.1 mm)
Mobile phase: A: 0.1% TFA/water, B: 0.1% TFA/acetonitrile
Temperature: 40° C.
Flow rate: 0.6 mL/min.
Gradient: 0.01 min. (B 10%), 0.33 min. (B 10%), 0.34 min. (B 20%), 0.66 min. (B 20%), 0.67 min. (B 30%), 0.99 min. (B 30%), 1.00 min. (B 40%), 1.33 min. (B 40%), 1.34 min. (B 50%), 1.66 min. (B 50%), 1.67 min. (B 80%), 2.50 min. (B 80%)

HPLC Condition 2
Column: Inertsil ODS-3 (150×4.6 mm)
Mobile phase: A: 0.1% TFA/water, B: 0.1% TFA/acetonitrile
Temperature: 40° C.
Flow rate: 1.0 mL/min
Gradient: 0.01 min. (B 10%), 20.00 min. (B 70%)

HPLC Condition 3
Column: Inertsil ODS-3 (150×4.6 mm)
Mobile phase: A: 0.1% TFA/water, B: 0.1% TFA/acetonitrile
Temperature: 40° C.
Flow rate: 1.5 mL/min
Gradient: 0.01 min. (B 25%), 8.00 min. (B 70%)

HPLC Condition 4
Column: Inertsil ODS-3 (150×4.6 mm)
Mobile phase: A: 0.1% TFA/water, B: 0.1% TFA/acetonitrile
Temperature: 40° C.
Flow rate: 1.5 mL/min
Gradient: 0.01 min. (B 5%), 8.00 min. (B 70%)

Further, the resulting objects of interest were subjected to mass spectroscopy by LC-MS or MALDI-TOF-MS under the conditions described below. The MS measured values for the different macrocyclic polypeptides are shown in Tables 5 to 7.

LC-MS Conditions
The LC-MS analysis was performed using Agilent 6530 Accurate-Mass Q-TOF LC/MS (produced by Agilent Technology).
Column: Kinetex 1.7u XB-C18 (50×2.1 mm)
Mobile phase: A: 0.1% TFA/water, B: 0.1% TFA/acetonitrile
Temperature: 40° C.
Flow rate: 0.6 mL/min.
Gradient: 0.01 min. (B 10%), 0.33 min. (B 10%), 0.34 min. (B 20%), 0.66 min. (B 20%), 0.67 min. (B 30%), 0.99 min. (B 30%), 1.00 min. (B 40%), 1.33 min. (B 40%), 1.34 min. (B 50%), 1.66 min. (B 50%), 1.67 min. (B 80%), 2.50 min. (B 80%)

MALDI-TOF-MS Conditions
The MALDI-TOF-MS analysis was performed using 4800 MALDI TOF/TOF (produced by AB Sciex). The matrix used was α-cyano-4-hydroxycinnamic acid (CHCA).

(Test Example 1) Cell Adhesion Inhibition Assay
I. Materials and Reagents
96 well Non-treated White with clear bottom (Coster, 3632)
BrightMax adhesive sealing films (EXCEL Scientific, WT50)
Proteosave®SS 15 mL (Sumitomo Bakelite, MS-52150)
Thrombospondin human platelet (Calbiochem, 605225)
HUVEC (KURABO, KE-4109P10)
EGM-2 MV (Lonza, CC-3202): for HUVEC passaging
Collagen coated dish (IWAKI, 4020-010): for HUVEC passaging
Lipidure®-BL802 (NOF Corporation), 5% solution
DMEM low glucose (GIBCO, 11054-020)
Albumin solution (35%) fraction V from Bovine (Sigma, A7979)
CellTiter-Glo (Promega, G7572)
IL Assay
<Plate Coat>
Thrombospondin 1 vial (25 μg) was dissolved in TBS (+2 mM CaCl$_2$; the same shall apply hereunder) to make a 200 μg/mL solution, which was diluted with TBS to a concentration of 10 μg/mL in Proteosave® 15 mL tube. The 10 μg/mL solution was dispensed into a 96 well plate at a volume of 50 μL/well (no reservoir was used since the protein easily adsorbs on it), and the plate was left to stand at 4° C. overnight.
<Plate Blocking>
Lipidure® was diluted 10-fold with TBS to make a 0.5% solution. After a buffer was discarded from the plate that had been coated at the step of <Plate coat> as described above, the 0.5% solution was dispensed into all wells to be used at a volume of 100 μL/well, and the plate was left to stand at room temperature for 1 hour.
<Sample Dilution>
A 0.2 μM solution of each sample was prepared using a dilution buffer (DMEM+0.5% BSA). 2 μL of the 0.2 μM solution was diluted with 500 μL, of dilution buffer to prepare a diluted sample. As a vehicle control, DMSO was diluted in the same way as the samples.
<Sample Dispensation>
A blocking solution was discarded from the plate that had been treated at the step of <Plate blocking> as described above, and the plate was washed three times with 150 μL/well of TBS. The washing solution used for the third washing was completely sucked out by an aspirator, and the diluted sample was dispensed into the plate at a volume of 50 µL/well. Then, the plate was left to stand at room temperature for 15 to 30 minutes.

<Huvec Seeding>

To maintain HUVECs, EGM2-MV and a collagen coated dish were used (the cells were ceased to be used after 10th or 11th passage since the cell proliferation rate declined at this stage). The cells were dispersed with 0.05% Trypsin/EDTA, harvested in DMEM/0.5% BSA, and centrifuged at 1000 rpm for 3 minutes. After removal of supernatant, the cells were washed once with a DMEM buffer. The cells were resuspended in a DMEM buffer, counted for cell number, and diluted to 10000 cells/50 µL. The cell suspension was dispensed at a volume of 50 µL/well into the plate into which the sample had been dispensed, mixed gently, and incubated at 37° C. for 2.5 hours.

<Washing and Detection>

After cell adhesion was confirmed, the culture medium was completely removed by an aspirator, and 100 µL/well of DMEM/0.5% BSA was gently dispensed. Then, DMEM/0.5% BSA was completely removed by an aspirator, and 50 µL/well of DMEM/0.5% BSA was dispensed. After a white seal was applied to the bottom of the plate, 50 µL/well of CellTiter-Glo® was dispensed, and the solution was stirred for 2 minutes and left to stand at room temperature for 8 minutes. Fluorescence emission was detected using EnVision Xcite Multilabel Reader (produced by Perkin Elmer).

III. Results

On the basis of the measured fluorescence values, the $IC_{50}$ values (nM) of the different macrocyclic polypeptides for inhibition of cell adhesion were calculated. The obtained results are shown in Tables 1 to 4. The results given above demonstrated that the compounds of Examples 1 to 104 have the ability to block the adhesion of TSP1 to vascular endothelial cells and are useful for the treatment or prophylaxis of critical limb ischemia or peripheral arterial disease.

(Test Example 2) Interaction Analysis by SPR

Interaction analysis by SPR was performed using Biacore T200 (produced by GE Healthcare).

I. Immobilization of Recombinant-hTSP1

First, 500 µM $NiCl_2$ was injected over an NTA-Chip (produced by GE Healthcare, BR100532) at a flow rate of 5 µL/min. for 1 minute to thereby activate NTA groups. Then, an EDC/NHS mixture was injected at a flow rate of 10 µL/min. for 7 minutes to thereby activate the carboxyl groups of dextran. Recombinant-hTSP1 was injected at a flow rate of 10 µL/min. for 7 minutes to immobilize the TSP1 on the substrate surfaces with activated NTA and carboxyl groups. Ethanolamine was injected at a flow rate of 10 µL/min. for 7 minutes to thereby deactivate unreacted, activated carboxyl groups.

The immobilization buffer used was prepared by diluting 10×HBS-P+(produced by GE Healthcare, BR100671) to 1-fold and adding 5 mM $CaCl_2$.

The reagents EDC/NHS/ethanolamine used were included in the Amine-coupling kit (BR100050) commercially available from GE Healthcare.

II. Sample measurement

The measurement buffer was prepared based on the following composition profile:

50 mM Tris-HCl pH7.5/150 mM NaCl/5 mM $CaCl_2$/0.05% Tween 20/5% DMSO.

The measurement was performed in the following steps.

1) Startup

For the purpose of equilibrating substrate surfaces, the measurement buffer was injected under the following conditions:

contact time: 60 sec., dissociation time: 120 sec., flow rate: 50 µL/min., temperature: 25° C.

The injection under the same conditions was repeated five times to ensure equilibration.

2) Solvent Correction

Since Biacore T200 is highly responsive to change in DMSO concentrations, DMSO solutions were sequentially injected at concentrations of 4%, 4.4%, 4.8%, 5.2%, 5.6%, and 6% to correct for DMSO effects.

3) Sample Measurement

The method adopted for sample measurement was a single-cycle kinetics method which is effective for samples showing low dissociative behavior. The advantage of this method is that since sample solutions at different concentration regions are injected in the same cycle, the influence between different cycles in association with low dissociation can be ignored in the analysis.

A 3-fold diluted series of sample solutions were prepared in five concentrations (100, 33, 11, 3.7 and 1.2 nM), and sequentially injected at a flow rate of 50 µL/min. for 3 minutes in the order from lowest to highest concentration. After the highest concentration of diluted solution was injected, a dissociation time of 20 to 30 minutes was spent.

Before samples were measured, the measurement buffer was injected alone under the same conditions to establish a baseline.

III. Analysis

The analysis was conducted using the evaluation software provided with Biacore T100 and T200. A DMSO correction curve obtained by solvent correction measurements was applied for the analysis. Kinetics fitting was done on the difference data obtained by subtracting the baseline data from sample measurement data.

KD values were calculated based on the association rate constant (ka) and dissociation rate constant (kd). The obtained results are shown in Tables 1 to 4. The results given above showed that compounds of Examples 1 to 7, 9 to 13, 24, 28, 40 to 45, 58, and 75 bind directly to TSP1 to thereby exhibit the activity to block the adhesion of TSP1 to vascular endothelial cells. Therefore, it was demonstrated that the macrocyclic polypeptides or pharmacologically acceptable salts thereof of the present invention are useful for the treatment or prophylaxis of critical limb ischemia or peripheral arterial disease.

(Test Example 3) Blood Flow Improvement Tests

Seven to nine-week-old male C57BL/6 mice were purchased from Charles River Laboratories Japan Inc., and acclimated over one week by feeding with a FR-2 solid diet (produced by Funabashi Farm Co., Ltd.). The rearing facility switched between light and dark modes in a 12-hour cycle with light turning on at 7 a.m and turning off at 7 p.m. Under isofluorane inhalation anaesthesia, the left thighs of the mice were dissected, and the superficial femoral arteries and veins (from just below the deep femoral arteries to the popliteal artery and vein) were ligated and excised. After animal models were made, the test substances (Compounds 24, 28, 40 to 45, and 58) were each dissolved in a solution of 20 mM lactic acid and 5% (w/v) Lutrol, and intraperitoneally injected into mice once daily.

(Blood Flow Improvement Test 1)

Vehicle-treated group

Compound 24 (10 mg/kg)-treated group (Blood Flow Improvement Test 2)

Vehicle-treated group

Compound 28 (10 mg/kg)-treated group (Blood Flow Improvement Test 3)
  Vehicle-treated group
  Compound 40 (10 mg/kg)-treated group
  Compound 41 (10 mg/kg)-treated group
(Blood Flow Improvement Test 4)
  Vehicle-treated group
  Compound 42 (10 mg/kg)-treated group
  Compound 43 (10 mg/kg)-treated group
  Compound 44 (10 mg/kg)-treated group
  Compound 45 (10 mg/kg)-treated group
(Blood Flow Improvement Test 5)
  Vehicle-treated group
  Compound 58 (10 mg/kg)-treated group Blood flows were measured in ischemic (left) and nonischemic (right) limbs using a laser Doppler perfusion imager (LDPI; PIM III, Perimed, Inc.). Blood flow values were evaluated by the ratio of ischemic limb flow to nonischemic limb flow.

Blood flow values from the mice were the lowest immediately after surgery and then gradually recovered. All of the test substances investigated in the animal models of this study improved blood flow recovery after surgery as compared to vehicle treatment. After 7 days of surgery, the blood flows in the test substance-treated groups were higher than in the vehicle-treated mice. The results are shown in Table 13.

TABLE 13

| | | %, ischemia/nonischemia | | | % change (vs. vehicle) |
|---|---|---|---|---|---|
| Exp 1 | Vehicle | 39.27 | ± | 2.37 | |
| | Compound 24 | 41.20 | ± | 6.18 | 4.9 |

TABLE 13-continued

| | | %, ischemia/nonischemia | | | % change (vs. vehicle) |
|---|---|---|---|---|---|
| Exp 2 | Vehicle | 40.06 | ± | 5.43 | |
| | Compound 28 | 40.79 | ± | 7.77 | 1.8 |
| Exp 3 | Vehicle | 43.74 | ± | 6.56 | |
| | Compound 40 | 46.53 | ± | 7.28 | 6.4 |
| | Compound 41 | 58.05 | ± | 3.76 | 32.7 |
| Exp 4 | Vehicle | 37.33 | ± | 2.92 | |
| | Compound 42 | 47.40 | ± | 5.62 | 27.0 |
| | Compound 43 | 48.86 | ± | 5.15 | 30.9 |
| | Compound 44 | 41.25 | ± | 3.54 | 10.5 |
| | Compound 45 | 65.70 | ± | 6.38 | 76.0 |
| Exp 5 | Vehicle | 37.19 | ± | 5.63 | |
| | Compound 58 | 69.00 | ± | 3.49 | 85.5 |

INDUSTRIAL APPLICABILITY

The macrocyclic polypeptides or pharmacologically acceptable salts thereof of the present invention can bind to TSP1 to block the adhesion of cells such as vascular endothelial cells to TSP1. Therefore, the macrocyclic polypeptides or pharmacologically acceptable salts thereof of this invention are useful for the treatment or prophylaxis of diseases or symptoms induced by increased TSP1 expression. Also, the macrocyclic polypeptides or pharmacologically acceptable salts thereof of this invention are useful as angiogenesis promoters.

SEQUENCE LISTING FREE TEXT

SEQ ID NOs: 1 to 104: Peptide regions of compounds of Examples 1 to 104
SEQ ID NOs: 1 to 104: Amidation of C-terminal carboxyl group

The invention claimed is:

1. A macrocyclic polypeptide represented by formula (I)

[Chem. 1]

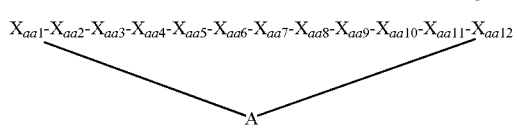

wherein A is selected from the linking groups of the formulas:

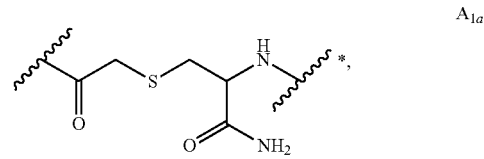

-continued

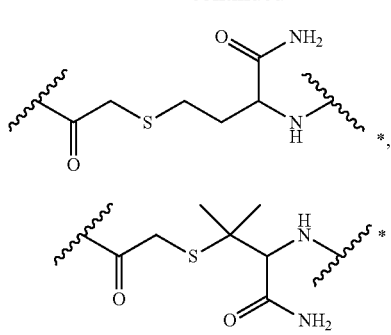

wherein

༺ represents a point of attachment to the N-terminal amino group of $X_{aa1}$, or in the absence of $X_{aa1}$, represents a point of attachment to the N-terminal amino group of $X_{aa2}$,

༺* represents a point of attachment to the C-terminal carbonyl group of $X_{aa12}$,
$X_{aa1}$ is Arg, Lys, His, Gly, Ala, Asn, Thr, Ser, Met, Leu, Ile, Val, Gln, Phe, Tyr, Trp, or Cys, or is absent;
$X_{aa2}$ is Phe, Tyr, Trp, 2Nal, 4CF, or DCF;
$X_{aa3}$ is Ile, Leu, Nle, Tle, Trp, 2Nal, 4CF, or Arg;
$X_{aa4}$ is Ser;
$X_{aa5}$ is Gly;
$X_{aa6}$ is Arg, Lys, His, Ser, Cit, or MO2;
$X_{aa7}$ is Asn or Asp;
$X_{aa8}$ is Trp, 2Nal, or 6CW;
$X_{aa9}$ is Val, Nle, Ahp, or Met;
$X_{aa10}$ is Arg, Lys, His, AMF, Phg, or Val;
$X_{aa11}$ is Trp or 2Nal;
$X_{aa12}$ is Val, Tle, or Phe;
or
a pharmacologically acceptable salt thereof.

2. The macrocyclic polypeptide or pharmacologically acceptable salt thereof according to claim 1, wherein $X_{aa8}$ is Trp.

3. The macrocyclic polypeptide or pharmacologically acceptable salt thereof according to claim 1, wherein $X_{aa11}$ is Trp.

4. The macrocyclic polypeptide or pharmacologically acceptable salt thereof according to claim 1, wherein $X_{aa1}$ is Arg, Lys, or Gly, or is absent.

5. The macrocyclic polypeptide or pharmacologically acceptable salt thereof according to claim 1, wherein $X_{aa2}$ is 2Nal.

6. The macrocyclic polypeptide or pharmacologically acceptable salt thereof according to claim 1, wherein $X_{aa3}$ is Ile, or Arg.

7. The macrocyclic polypeptide or pharmacologically acceptable salt thereof according to claim 1, wherein $X_{aa6}$ is Arg, Lys, His, or Ser.

8. The macrocyclic polypeptide or pharmacologically acceptable salt thereof according to claim 1, wherein $X_{aa9}$, is Val, Nle, or Ahp.

9. The macrocyclic polypeptide or pharmacologically acceptable salt thereof according to claim 1, wherein $X_{aa10}$ is Arg, Lys, His, Phg, or Val.

10. The macrocyclic polypeptide or pharmacologically acceptable salt thereof according to claim 1, wherein $X_{aa12}$ is Val.

11. The macrocyclic polypeptide or pharmacologically acceptable salt thereof according to claim 1, wherein A is

[Chem. 14]

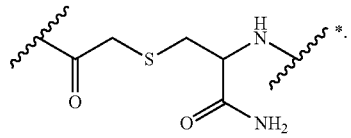

12. The macrocyclic polypeptide or pharmacologically acceptable salt thereof according to claim 1, wherein
$X_{aa1}$ is Arg, Lys, or Gly, or is absent;
$X_{aa2}$ is 2Nal;
$X_{aa3}$ is Ile, or Arg;
$X_{aa4}$ is Ser;
$X_{aa5}$ is Gly;
$X_{aa6}$ is Arg, Lys, His, or Ser;
$X_{aa7}$ is Asn or Asp;
$X_{aa8}$ is Trp;
$X_{aa9}$ is Val, Nle, or Ahp;
$X_{aa10}$ is Arg, Lys, His, Phg, or Val;
$X_{aa11}$ is Trp;
$X_{aa12}$ is Val;
A is

[Chem. 16]

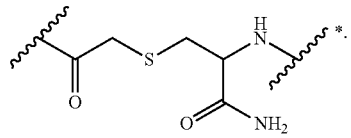

13. A pharmaceutical composition comprising, as an active component, the macrocyclic polypeptide or pharmacologically acceptable salt thereof according to claim 1.

14. A method for the treatment of a disease or symptom, the method comprising administering to a human in need thereof a therapeutically effective amount of the macrocyclic polypeptide or pharmacologically acceptable salt thereof according to claim 1, wherein the disease or symptom is critical limb ischemia or peripheral arterial disease.

15. A method for promoting angiogenesis, the method comprising administering to a human in need thereof a therapeutically effective amount of the macrocyclic polypeptide or pharmacologically acceptable salt thereof according to claim 1.

16. The macrocyclic polypeptide or pharmacologically acceptable salt thereof according to claim 12, wherein the macrocyclic polypeptide or pharmacologically acceptable salt thereof is selected from the group consisting of the compounds represented by the formulas:

[Chem. 17]
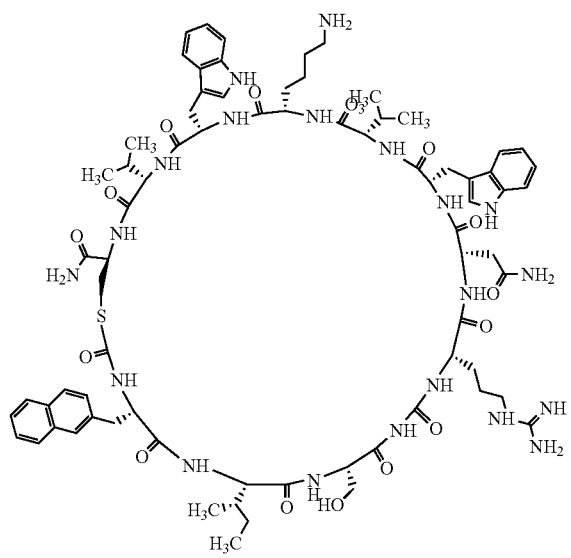
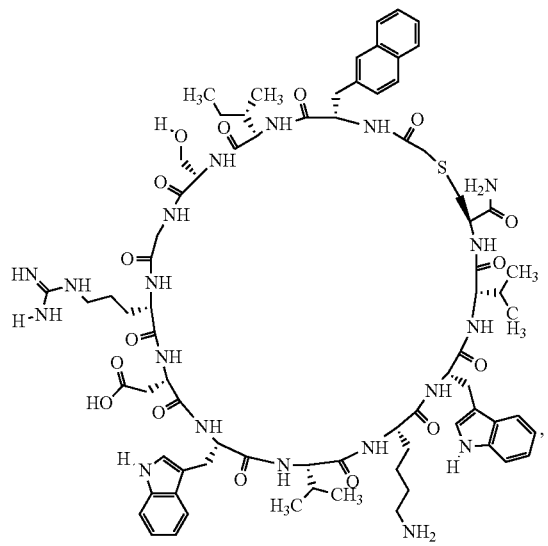
[Chem. 18]
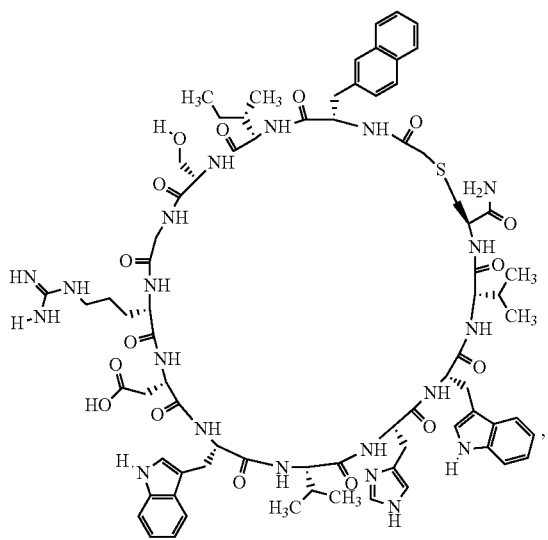
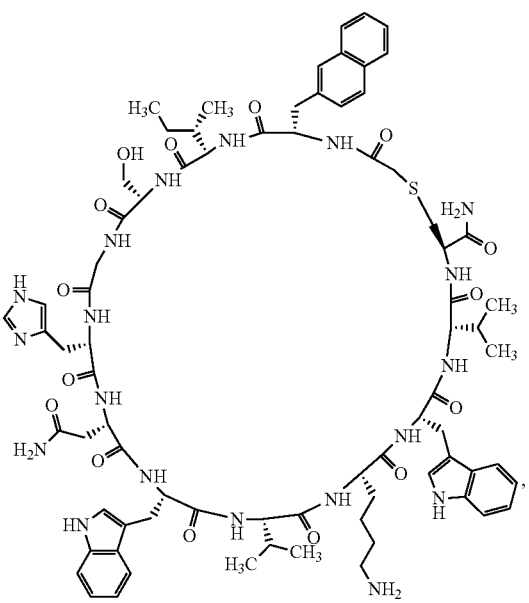
[Chem. 19]
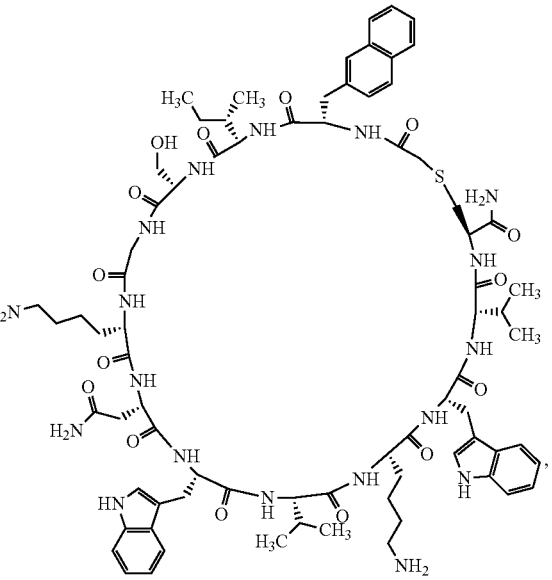

199
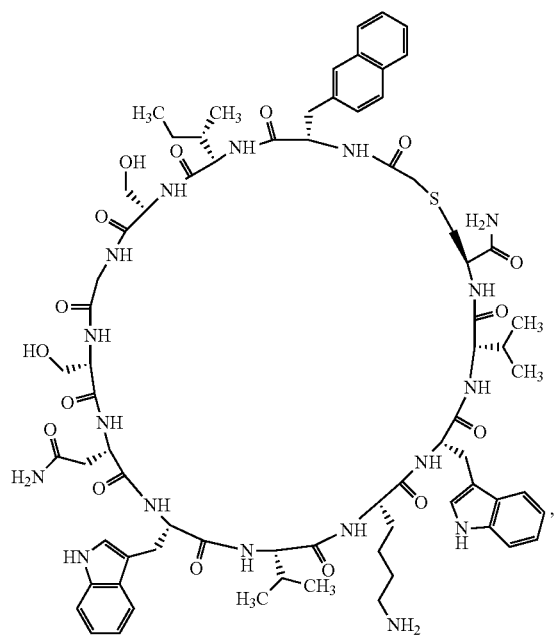
[Chem. 20]
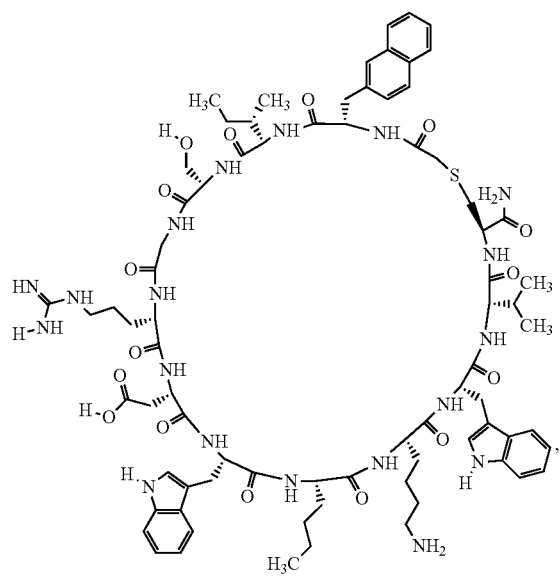
200
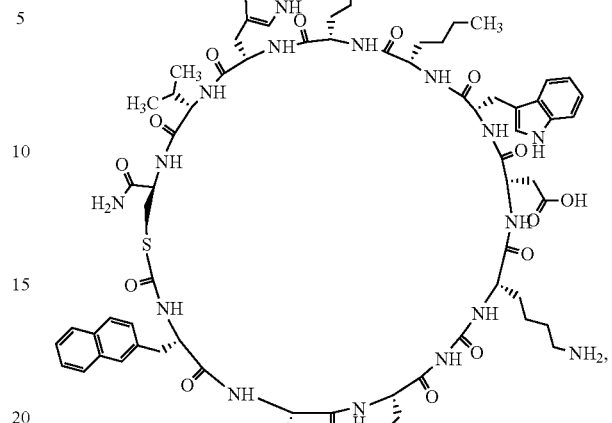
[Chem. 21]
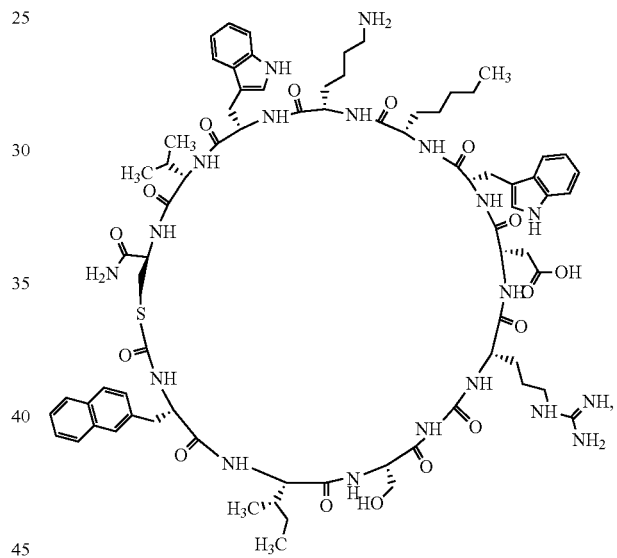
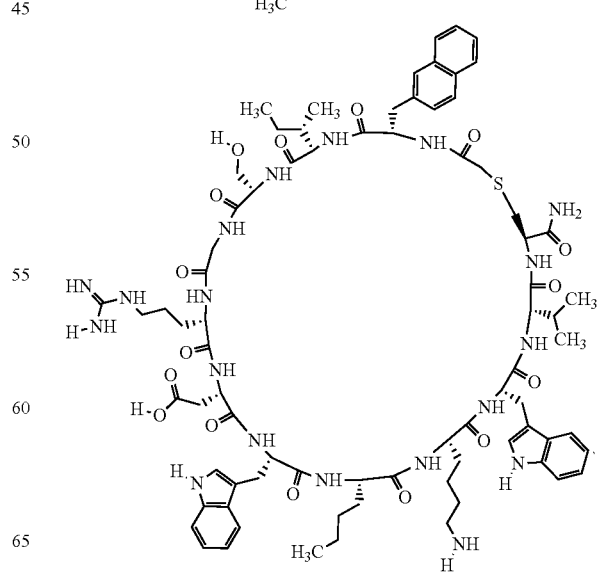

201
-continued
[Chem. 22]
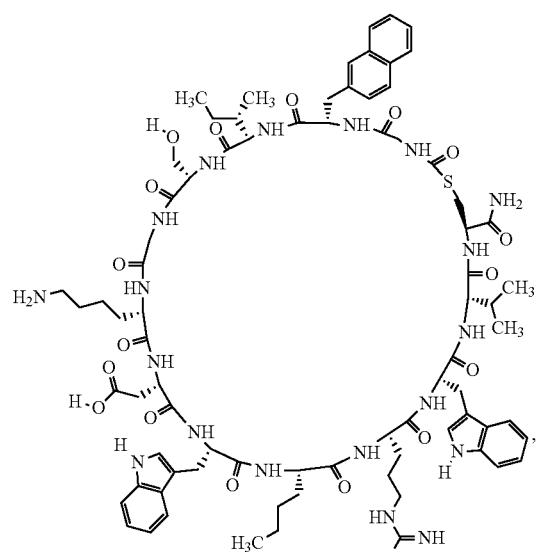
[Chem. 23]
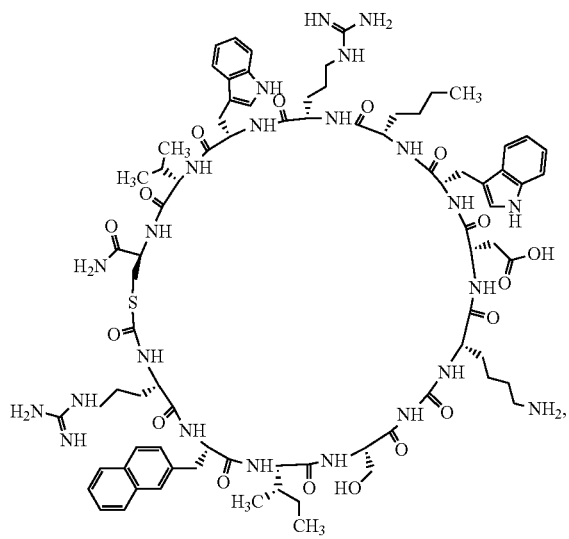
202
-continued
[Chem. 24]
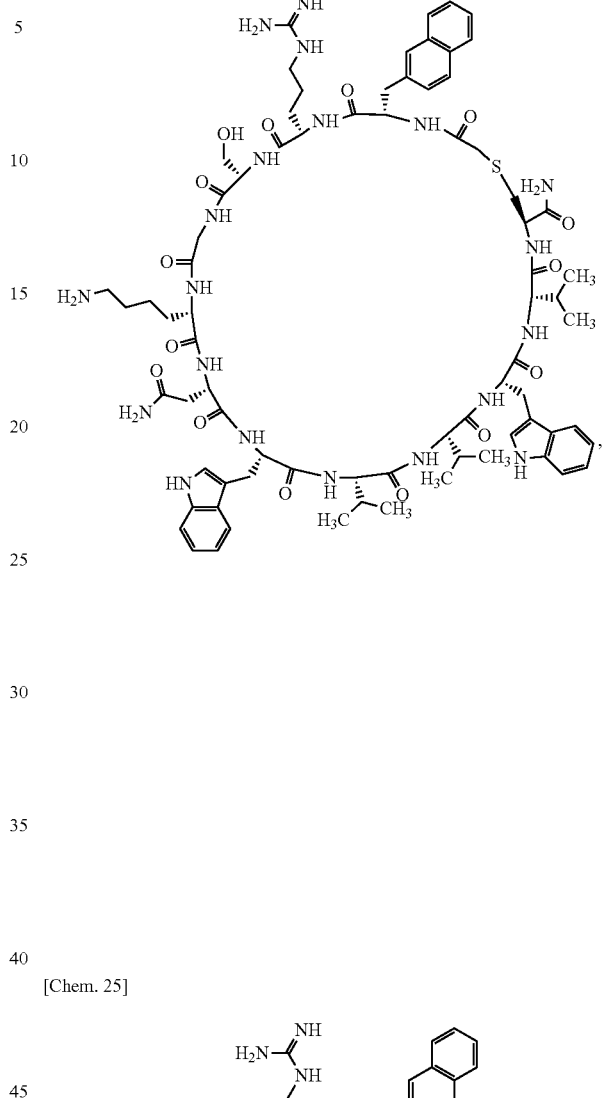
[Chem. 25]
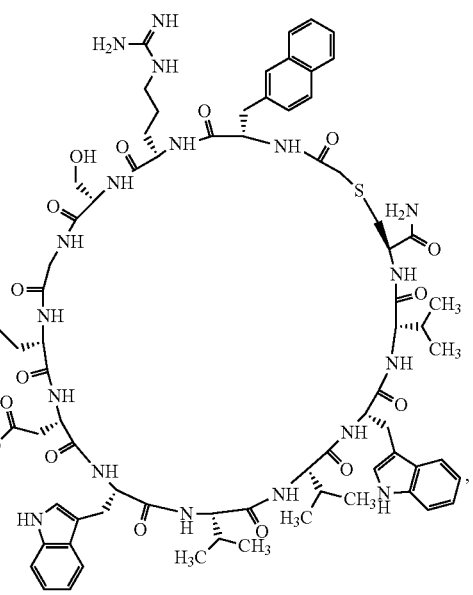

203
{Chem. 26]
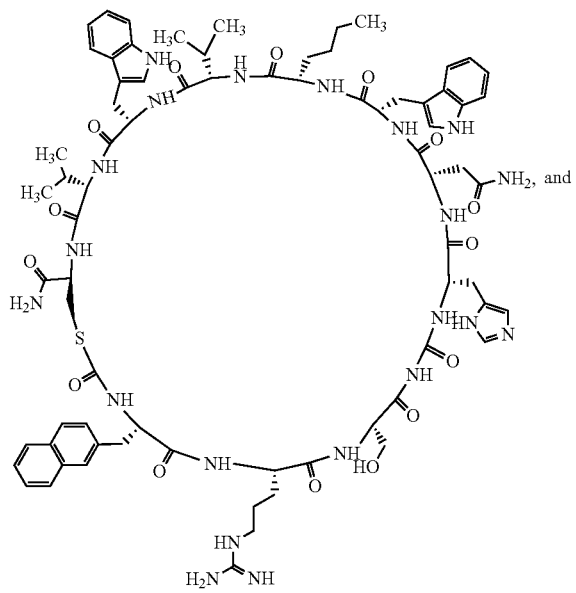
NH₂, and
[Chem. 27]
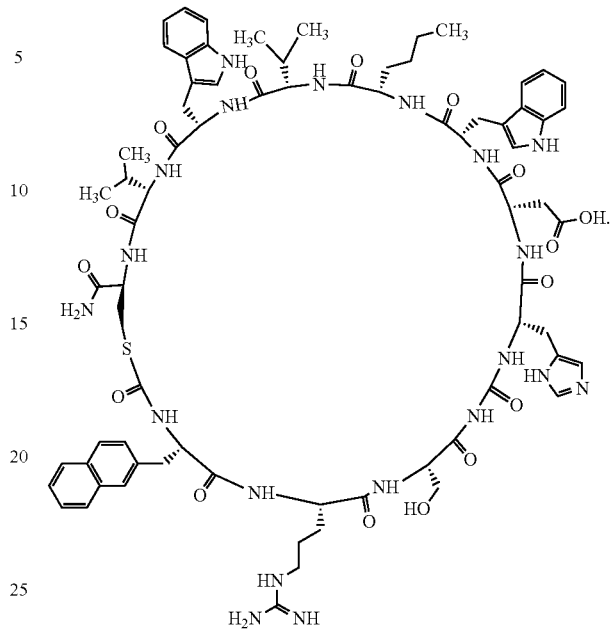
OH.
* * * * *

SEQUENCE LISTING

```
<160> NUMBER OF SEQ ID NOS: 104

<210> SEQ ID NO 1
<211> LENGTH: 12
<212> TYPE: PRT
<213> ORGANISM: Artificial Sequence
<220> FEATURE:
<223> OTHER INFORMATION: Peptide region of compound of Example 1
<220> FEATURE:
<221> NAME/KEY: MISC_FEATURE
<222> LOCATION: (12)..(12)
<223> OTHER INFORMATION: Amidation of C-terminal carboxyl group

<400> SEQUENCE: 1

Phe Ile Ser Gly Arg Asn Trp Val Val Trp Val Cys
1               5                   10

<210> SEQ ID NO 2
<211> LENGTH: 12
<212> TYPE: PRT
<213> ORGANISM: Artificial Sequence
<220> FEATURE:
<223> OTHER INFORMATION: Peptide region of compound of Example 2
<220> FEATURE:
<221> NAME/KEY: MISC_FEATURE
<222> LOCATION: (12)..(12)
<223> OTHER INFORMATION: Amidation of C-terminal carboxyl group

<400> SEQUENCE: 2

Phe Arg Ser Gly Arg Asn Trp Val Val Trp Val Cys
1               5                   10
```

```
<210> SEQ ID NO 3
<211> LENGTH: 12
<212> TYPE: PRT
<213> ORGANISM: Artificial Sequence
<220> FEATURE:
<223> OTHER INFORMATION: Peptide region of compound of Example 3
<220> FEATURE:
<221> NAME/KEY: MISC_FEATURE
<222> LOCATION: (12)..(12)
<223> OTHER INFORMATION: Amidation of C-terminal carboxyl group

<400> SEQUENCE: 3

Phe Ile Ser Gly Arg Asn Trp Val Lys Trp Val Cys
1               5                   10

<210> SEQ ID NO 4
<211> LENGTH: 12
<212> TYPE: PRT
<213> ORGANISM: Artificial Sequence
<220> FEATURE:
<223> OTHER INFORMATION: Peptide region of compound of Example 4
<220> FEATURE:
<221> NAME/KEY: MISC_FEATURE
<222> LOCATION: (12)..(12)
<223> OTHER INFORMATION: Amidation of C-terminal carboxyl group

<400> SEQUENCE: 4

Phe Ile Ser Gly Arg Asn Trp Val Arg Trp Val Cys
1               5                   10

<210> SEQ ID NO 5
<211> LENGTH: 12
<212> TYPE: PRT
<213> ORGANISM: Artificial Sequence
<220> FEATURE:
<223> OTHER INFORMATION: Peptide region of compound of Example 5
<220> FEATURE:
<221> NAME/KEY: MISC_FEATURE
<222> LOCATION: (12)..(12)
<223> OTHER INFORMATION: Amidation of C-terminal carboxyl group

<400> SEQUENCE: 5

Phe Ile Ser Gly Arg Asn Trp Val Arg Trp Arg Cys
1               5                   10

<210> SEQ ID NO 6
<211> LENGTH: 12
<212> TYPE: PRT
<213> ORGANISM: Artificial Sequence
<220> FEATURE:
<223> OTHER INFORMATION: Peptide region of compound of Example 6
<220> FEATURE:
<221> NAME/KEY: MISC_FEATURE
<222> LOCATION: (12)..(12)
<223> OTHER INFORMATION: Amidation of C-terminal carboxyl group

<400> SEQUENCE: 6

Phe Arg Ser Gly Arg Asn Trp Val Lys Trp Val Cys
1               5                   10

<210> SEQ ID NO 7
<211> LENGTH: 12
<212> TYPE: PRT
<213> ORGANISM: Artificial Sequence
<220> FEATURE:
<223> OTHER INFORMATION: Peptide region of compound of Example 7
<220> FEATURE:
<221> NAME/KEY: MISC_FEATURE
<222> LOCATION: (12)..(12)
<223> OTHER INFORMATION: Amidation of C-terminal carboxyl group
```

```
<400> SEQUENCE: 7

Phe Ile Ser Gly Lys Asn Trp Val Lys Trp Val Cys
1               5                   10

<210> SEQ ID NO 8
<211> LENGTH: 12
<212> TYPE: PRT
<213> ORGANISM: Artificial Sequence
<220> FEATURE:
<223> OTHER INFORMATION: Peptide region of compound of Example 8
<220> FEATURE:
<221> NAME/KEY: MISC_FEATURE
<222> LOCATION: (12)..(12)
<223> OTHER INFORMATION: Amidation of C-terminal carboxyl group

<400> SEQUENCE: 8

Phe Arg Ser Gly Arg Asn Trp Val Arg Trp Val Cys
1               5                   10

<210> SEQ ID NO 9
<211> LENGTH: 12
<212> TYPE: PRT
<213> ORGANISM: Artificial Sequence
<220> FEATURE:
<223> OTHER INFORMATION: Peptide region of compound of Example 9
<220> FEATURE:
<221> NAME/KEY: MISC_FEATURE
<222> LOCATION: (12)..(12)
<223> OTHER INFORMATION: Amidation of C-terminal carboxyl group

<400> SEQUENCE: 9

Trp Ile Ser Gly Arg Asn Trp Val Lys Trp Val Cys
1               5                   10

<210> SEQ ID NO 10
<211> LENGTH: 12
<212> TYPE: PRT
<213> ORGANISM: Artificial Sequence
<220> FEATURE:
<223> OTHER INFORMATION: Peptide region of compound of Example 10
<220> FEATURE:
<221> NAME/KEY: MISC_FEATURE
<222> LOCATION: (12)..(12)
<223> OTHER INFORMATION: Amidation of C-terminal carboxyl group

<400> SEQUENCE: 10

Phe Ile Ser Gly Lys Asn Trp Val Arg Trp Val Cys
1               5                   10

<210> SEQ ID NO 11
<211> LENGTH: 12
<212> TYPE: PRT
<213> ORGANISM: Artificial Sequence
<220> FEATURE:
<223> OTHER INFORMATION: Peptide region of compound of Example 11
<220> FEATURE:
<221> NAME/KEY: MISC_FEATURE
<222> LOCATION: (12)..(12)
<223> OTHER INFORMATION: Amidation of C-terminal carboxyl group

<400> SEQUENCE: 11

Trp Ile Ser Gly Arg Asn Trp Val Arg Trp Val Cys
1               5                   10

<210> SEQ ID NO 12
<211> LENGTH: 12
<212> TYPE: PRT
<213> ORGANISM: Artificial Sequence
```

```
<220> FEATURE:
<223> OTHER INFORMATION: Peptide region of compound of Example 12
<220> FEATURE:
<221> NAME/KEY: MISC_FEATURE
<222> LOCATION: (12)..(12)
<223> OTHER INFORMATION: Amidation of C-terminal carboxyl group

<400> SEQUENCE: 12

Phe Ile Thr Gly Arg Asn Trp Val Lys Trp Val Cys
1               5                   10

<210> SEQ ID NO 13
<211> LENGTH: 12
<212> TYPE: PRT
<213> ORGANISM: Artificial Sequence
<220> FEATURE:
<223> OTHER INFORMATION: Peptide region of compound of Example 13
<220> FEATURE:
<221> NAME/KEY: MISC_FEATURE
<222> LOCATION: (12)..(12)
<223> OTHER INFORMATION: Amidation of C-terminal carboxyl group

<400> SEQUENCE: 13

Phe Ile Ser Gly Arg Thr Trp Val Lys Trp Val Cys
1               5                   10

<210> SEQ ID NO 14
<211> LENGTH: 12
<212> TYPE: PRT
<213> ORGANISM: Artificial Sequence
<220> FEATURE:
<223> OTHER INFORMATION: Peptide region of compound of Example 14
<220> FEATURE:
<221> NAME/KEY: MISC_FEATURE
<222> LOCATION: (3)..(3)
<223> OTHER INFORMATION: N-Methylserine
<220> FEATURE:
<221> NAME/KEY: MISC_FEATURE
<222> LOCATION: (12)..(12)
<223> OTHER INFORMATION: Amidation of C-terminal carboxyl group

<400> SEQUENCE: 14

Phe Ile Xaa Gly Arg Asn Trp Val Lys Trp Val Cys
1               5                   10

<210> SEQ ID NO 15
<211> LENGTH: 13
<212> TYPE: PRT
<213> ORGANISM: Artificial Sequence
<220> FEATURE:
<223> OTHER INFORMATION: Peptide region of compound of Example 15
<220> FEATURE:
<221> NAME/KEY: MISC_FEATURE
<222> LOCATION: (13)..(13)
<223> OTHER INFORMATION: Amidation of C-terminal carboxyl group

<400> SEQUENCE: 15

Cys Phe Ile Ser Gly Arg Asn Trp Val Lys Trp Val Cys
1               5                   10

<210> SEQ ID NO 16
<211> LENGTH: 12
<212> TYPE: PRT
<213> ORGANISM: Artificial Sequence
<220> FEATURE:
<223> OTHER INFORMATION: Peptide region of compound of Example 16
<220> FEATURE:
<221> NAME/KEY: MISC_FEATURE
<222> LOCATION: (12)..(12)
<223> OTHER INFORMATION: Amidation of C-terminal carboxyl group
```

```
<400> SEQUENCE: 16

Trp Ile Ser Gly Lys Asn Trp Val Lys Trp Val Cys
1               5                   10

<210> SEQ ID NO 17
<211> LENGTH: 12
<212> TYPE: PRT
<213> ORGANISM: Artificial Sequence
<220> FEATURE:
<223> OTHER INFORMATION: Peptide region of compound of Example 17
<220> FEATURE:
<221> NAME/KEY: MISC_FEATURE
<222> LOCATION: (12)..(12)
<223> OTHER INFORMATION: Amidation of C-terminal carboxyl group

<400> SEQUENCE: 17

Phe Ile Thr Gly Lys Asn Trp Val Lys Trp Val Cys
1               5                   10

<210> SEQ ID NO 18
<211> LENGTH: 12
<212> TYPE: PRT
<213> ORGANISM: Artificial Sequence
<220> FEATURE:
<223> OTHER INFORMATION: Peptide region of compound of Example 18
<220> FEATURE:
<221> NAME/KEY: MISC_FEATURE
<222> LOCATION: (12)..(12)
<223> OTHER INFORMATION: Amidation of C-terminal carboxyl group

<400> SEQUENCE: 18

Phe Ile Ser Gly Lys Thr Trp Val Lys Trp Val Cys
1               5                   10

<210> SEQ ID NO 19
<211> LENGTH: 12
<212> TYPE: PRT
<213> ORGANISM: Artificial Sequence
<220> FEATURE:
<223> OTHER INFORMATION: Peptide region of compound of Example 19
<220> FEATURE:
<221> NAME/KEY: MISC_FEATURE
<222> LOCATION: (12)..(12)
<223> OTHER INFORMATION: Amidation of C-terminal carboxyl group

<400> SEQUENCE: 19

Phe Ile Ser Gly Lys Asn Trp Met Lys Trp Val Cys
1               5                   10

<210> SEQ ID NO 20
<211> LENGTH: 12
<212> TYPE: PRT
<213> ORGANISM: Artificial Sequence
<220> FEATURE:
<223> OTHER INFORMATION: Peptide region of compound of Example 20
<220> FEATURE:
<221> NAME/KEY: MISC_FEATURE
<222> LOCATION: (12)..(12)
<223> OTHER INFORMATION: Amidation of C-terminal carboxyl group

<400> SEQUENCE: 20

Trp Ile Ser Gly Lys Thr Trp Val Lys Trp Val Cys
1               5                   10

<210> SEQ ID NO 21
<211> LENGTH: 12
<212> TYPE: PRT
<213> ORGANISM: Artificial Sequence
<220> FEATURE:
```

```
<223> OTHER INFORMATION: Peptide region of compound of Example 21
<220> FEATURE:
<221> NAME/KEY: MISC_FEATURE
<222> LOCATION: (12)..(12)
<223> OTHER INFORMATION: Amidation of C-terminal carboxyl group

<400> SEQUENCE: 21

Phe Ile Ser Gly Lys Asn Trp Met Arg Trp Val Cys
1               5                   10

<210> SEQ ID NO 22
<211> LENGTH: 12
<212> TYPE: PRT
<213> ORGANISM: Artificial Sequence
<220> FEATURE:
<223> OTHER INFORMATION: Peptide region of compound of Example 22
<220> FEATURE:
<221> NAME/KEY: MISC_FEATURE
<222> LOCATION: (12)..(12)
<223> OTHER INFORMATION: Amidation of C-terminal carboxyl group

<400> SEQUENCE: 22

Trp Ile Ser Gly Lys Thr Trp Val Arg Trp Val Cys
1               5                   10

<210> SEQ ID NO 23
<211> LENGTH: 12
<212> TYPE: PRT
<213> ORGANISM: Artificial Sequence
<220> FEATURE:
<223> OTHER INFORMATION: Peptide region of compound of Example 23
<220> FEATURE:
<221> NAME/KEY: MISC_FEATURE
<222> LOCATION: (12)..(12)
<223> OTHER INFORMATION: Amidation of C-terminal carboxyl group

<400> SEQUENCE: 23

Trp Ile Ser Gly Arg Thr Trp Val Lys Trp Val Cys
1               5                   10

<210> SEQ ID NO 24
<211> LENGTH: 12
<212> TYPE: PRT
<213> ORGANISM: Artificial Sequence
<220> FEATURE:
<223> OTHER INFORMATION: Peptide region of compound of Example 24
<220> FEATURE:
<221> NAME/KEY: MISC_FEATURE
<222> LOCATION: (1)..(1)
<223> OTHER INFORMATION: 2Nal
<220> FEATURE:
<221> NAME/KEY: MISC_FEATURE
<222> LOCATION: (12)..(12)
<223> OTHER INFORMATION: Amidation of C-terminal carboxyl group

<400> SEQUENCE: 24

Xaa Ile Ser Gly Arg Asn Trp Val Lys Trp Val Cys
1               5                   10

<210> SEQ ID NO 25
<211> LENGTH: 12
<212> TYPE: PRT
<213> ORGANISM: Artificial Sequence
<220> FEATURE:
<223> OTHER INFORMATION: Peptide region of compound of Example 25
<220> FEATURE:
<221> NAME/KEY: MISC_FEATURE
<222> LOCATION: (1)..(1)
<223> OTHER INFORMATION: 4CF
<220> FEATURE:
<221> NAME/KEY: MISC_FEATURE
```

```
<222> LOCATION: (12)..(12)
<223> OTHER INFORMATION: Amidation of C-terminal carboxyl group

<400> SEQUENCE: 25

Xaa Ile Ser Gly Arg Asn Trp Val Lys Trp Val Cys
1               5                   10

<210> SEQ ID NO 26
<211> LENGTH: 12
<212> TYPE: PRT
<213> ORGANISM: Artificial Sequence
<220> FEATURE:
<223> OTHER INFORMATION: Peptide region of compound of Example 26
<220> FEATURE:
<221> NAME/KEY: MISC_FEATURE
<222> LOCATION: (8)..(8)
<223> OTHER INFORMATION: Nle
<220> FEATURE:
<221> NAME/KEY: MISC_FEATURE
<222> LOCATION: (12)..(12)
<223> OTHER INFORMATION: Amidation of C-terminal carboxyl group

<400> SEQUENCE: 26

Phe Ile Ser Gly Arg Asn Trp Xaa Lys Trp Val Cys
1               5                   10

<210> SEQ ID NO 27
<211> LENGTH: 12
<212> TYPE: PRT
<213> ORGANISM: Artificial Sequence
<220> FEATURE:
<223> OTHER INFORMATION: Peptide region of compound of Example 27
<220> FEATURE:
<221> NAME/KEY: MISC_FEATURE
<222> LOCATION: (1)..(1)
<223> OTHER INFORMATION: 2Nal
<220> FEATURE:
<221> NAME/KEY: MISC_FEATURE
<222> LOCATION: (12)..(12)
<223> OTHER INFORMATION: Amidation of C-terminal carboxyl group

<400> SEQUENCE: 27

Xaa Phe Ser Gly Arg Asn Trp Val Lys Trp Val Cys
1               5                   10

<210> SEQ ID NO 28
<211> LENGTH: 12
<212> TYPE: PRT
<213> ORGANISM: Artificial Sequence
<220> FEATURE:
<223> OTHER INFORMATION: Peptide region of compound of Example 28
<220> FEATURE:
<221> NAME/KEY: MISC_FEATURE
<222> LOCATION: (1)..(1)
<223> OTHER INFORMATION: 2Nal
<220> FEATURE:
<221> NAME/KEY: MISC_FEATURE
<222> LOCATION: (7)..(7)
<223> OTHER INFORMATION: 2Nal
<220> FEATURE:
<221> NAME/KEY: MISC_FEATURE
<222> LOCATION: (12)..(12)
<223> OTHER INFORMATION: Amidation of C-terminal carboxyl group

<400> SEQUENCE: 28

Xaa Ile Ser Gly Arg Asn Xaa Val Lys Trp Val Cys
1               5                   10

<210> SEQ ID NO 29
<211> LENGTH: 12
<212> TYPE: PRT
```

```
<213> ORGANISM: Artificial Sequence
<220> FEATURE:
<223> OTHER INFORMATION: Peptide region of compound of Example 29
<220> FEATURE:
<221> NAME/KEY: MISC_FEATURE
<222> LOCATION: (1)..(1)
<223> OTHER INFORMATION: 2Nal
<220> FEATURE:
<221> NAME/KEY: MISC_FEATURE
<222> LOCATION: (10)..(10)
<223> OTHER INFORMATION: 2Nal
<220> FEATURE:
<221> NAME/KEY: MISC_FEATURE
<222> LOCATION: (12)..(12)
<223> OTHER INFORMATION: Amidation of C-terminal carboxyl group

<400> SEQUENCE: 29

Xaa Ile Ser Gly Arg Asn Trp Val Lys Xaa Val Cys
 1               5                  10

<210> SEQ ID NO 30
<211> LENGTH: 12
<212> TYPE: PRT
<213> ORGANISM: Artificial Sequence
<220> FEATURE:
<223> OTHER INFORMATION: Peptide region of compound of Example 30
<220> FEATURE:
<221> NAME/KEY: MISC_FEATURE
<222> LOCATION: (1)..(1)
<223> OTHER INFORMATION: 2Nal
<220> FEATURE:
<221> NAME/KEY: MISC_FEATURE
<222> LOCATION: (12)..(12)
<223> OTHER INFORMATION: Amidation of C-terminal carboxyl group

<400> SEQUENCE: 30

Xaa Ile Ala Gly Arg Asn Trp Val Lys Trp Val Cys
 1               5                  10

<210> SEQ ID NO 31
<211> LENGTH: 12
<212> TYPE: PRT
<213> ORGANISM: Artificial Sequence
<220> FEATURE:
<223> OTHER INFORMATION: Peptide region of compound of Example 31
<220> FEATURE:
<221> NAME/KEY: MISC_FEATURE
<222> LOCATION: (1)..(1)
<223> OTHER INFORMATION: 2Nal
<220> FEATURE:
<221> NAME/KEY: MISC_FEATURE
<222> LOCATION: (2)..(2)
<223> OTHER INFORMATION: 4CF
<220> FEATURE:
<221> NAME/KEY: MISC_FEATURE
<222> LOCATION: (12)..(12)
<223> OTHER INFORMATION: Amidation of C-terminal carboxyl group

<400> SEQUENCE: 31

Xaa Xaa Ser Gly Arg Asn Trp Val Lys Trp Val Cys
 1               5                  10

<210> SEQ ID NO 32
<211> LENGTH: 12
<212> TYPE: PRT
<213> ORGANISM: Artificial Sequence
<220> FEATURE:
<223> OTHER INFORMATION: Peptide region of compound of Example 32
<220> FEATURE:
<221> NAME/KEY: MISC_FEATURE
<222> LOCATION: (1)..(1)
<223> OTHER INFORMATION: 2Nal
<220> FEATURE:
```

```
<221> NAME/KEY: MISC_FEATURE
<222> LOCATION: (2)..(2)
<223> OTHER INFORMATION: HF
<220> FEATURE:
<221> NAME/KEY: MISC_FEATURE
<222> LOCATION: (12)..(12)
<223> OTHER INFORMATION: Amidation of C-terminal carboxyl group

<400> SEQUENCE: 32

Xaa Xaa Ser Gly Arg Asn Trp Val Lys Trp Val Cys
1               5                   10

<210> SEQ ID NO 33
<211> LENGTH: 12
<212> TYPE: PRT
<213> ORGANISM: Artificial Sequence
<220> FEATURE:
<223> OTHER INFORMATION: Peptide region of compound of Example 33
<220> FEATURE:
<221> NAME/KEY: MISC_FEATURE
<222> LOCATION: (1)..(1)
<223> OTHER INFORMATION: 2Nal
<220> FEATURE:
<221> NAME/KEY: MISC_FEATURE
<222> LOCATION: (12)..(12)
<223> OTHER INFORMATION: Amidation of C-terminal carboxyl group

<400> SEQUENCE: 33

Xaa Trp Ser Gly Arg Asn Trp Val Lys Trp Val Cys
1               5                   10

<210> SEQ ID NO 34
<211> LENGTH: 12
<212> TYPE: PRT
<213> ORGANISM: Artificial Sequence
<220> FEATURE:
<223> OTHER INFORMATION: Peptide region of compound of Example 34
<220> FEATURE:
<221> NAME/KEY: MISC_FEATURE
<222> LOCATION: (1)..(1)
<223> OTHER INFORMATION: DCF
<220> FEATURE:
<221> NAME/KEY: MISC_FEATURE
<222> LOCATION: (2)..(2)
<223> OTHER INFORMATION: 2Nal
<220> FEATURE:
<221> NAME/KEY: MISC_FEATURE
<222> LOCATION: (12)..(12)
<223> OTHER INFORMATION: Amidation of C-terminal carboxyl group

<400> SEQUENCE: 34

Xaa Xaa Ser Gly Arg Asn Trp Val Lys Trp Val Cys
1               5                   10

<210> SEQ ID NO 35
<211> LENGTH: 12
<212> TYPE: PRT
<213> ORGANISM: Artificial Sequence
<220> FEATURE:
<223> OTHER INFORMATION: Peptide region of compound of Example 35
<220> FEATURE:
<221> NAME/KEY: MISC_FEATURE
<222> LOCATION: (1)..(1)
<223> OTHER INFORMATION: 2Nal
<220> FEATURE:
<221> NAME/KEY: MISC_FEATURE
<222> LOCATION: (7)..(7)
<223> OTHER INFORMATION: 6CW
<220> FEATURE:
<221> NAME/KEY: MISC_FEATURE
<222> LOCATION: (12)..(12)
<223> OTHER INFORMATION: Amidation of C-terminal carboxyl group
```

```
<400> SEQUENCE: 35

Xaa Ile Ser Gly Arg Asn Xaa Val Lys Trp Val Cys
1               5                   10

<210> SEQ ID NO 36
<211> LENGTH: 12
<212> TYPE: PRT
<213> ORGANISM: Artificial Sequence
<220> FEATURE:
<223> OTHER INFORMATION: Peptide region of compound of Example 36
<220> FEATURE:
<221> NAME/KEY: MISC_FEATURE
<222> LOCATION: (1)..(1)
<223> OTHER INFORMATION: 2Nal
<220> FEATURE:
<221> NAME/KEY: MISC_FEATURE
<222> LOCATION: (10)..(10)
<223> OTHER INFORMATION: 6CW
<220> FEATURE:
<221> NAME/KEY: MISC_FEATURE
<222> LOCATION: (12)..(12)
<223> OTHER INFORMATION: Amidation of C-terminal carboxyl group

<400> SEQUENCE: 36

Xaa Ile Ser Gly Arg Asn Trp Val Lys Xaa Val Cys
1               5                   10

<210> SEQ ID NO 37
<211> LENGTH: 12
<212> TYPE: PRT
<213> ORGANISM: Artificial Sequence
<220> FEATURE:
<223> OTHER INFORMATION: Peptide region of compound of Example 37
<220> FEATURE:
<221> NAME/KEY: MISC_FEATURE
<222> LOCATION: (1)..(1)
<223> OTHER INFORMATION: 2Nal
<220> FEATURE:
<221> NAME/KEY: MISC_FEATURE
<222> LOCATION: (11)..(11)
<223> OTHER INFORMATION: HF
<220> FEATURE:
<221> NAME/KEY: MISC_FEATURE
<222> LOCATION: (12)..(12)
<223> OTHER INFORMATION: Amidation of C-terminal carboxyl group

<400> SEQUENCE: 37

Xaa Ile Ser Gly Arg Asn Trp Val Lys Trp Xaa Cys
1               5                   10

<210> SEQ ID NO 38
<211> LENGTH: 12
<212> TYPE: PRT
<213> ORGANISM: Artificial Sequence
<220> FEATURE:
<223> OTHER INFORMATION: Peptide region of compound of Example 38
<220> FEATURE:
<221> NAME/KEY: MISC_FEATURE
<222> LOCATION: (1)..(1)
<223> OTHER INFORMATION: 2Nal
<220> FEATURE:
<221> NAME/KEY: MISC_FEATURE
<222> LOCATION: (8)..(8)
<223> OTHER INFORMATION: Nle
<220> FEATURE:
<221> NAME/KEY: MISC_FEATURE
<222> LOCATION: (12)..(12)
<223> OTHER INFORMATION: Amidation of C-terminal carboxyl group

<400> SEQUENCE: 38

Xaa Ile Ser Gly Arg Asn Trp Xaa Lys Trp Val Cys
1               5                   10
```

```
<210> SEQ ID NO 39
<211> LENGTH: 12
<212> TYPE: PRT
<213> ORGANISM: Artificial Sequence
<220> FEATURE:
<223> OTHER INFORMATION: Peptide region of compound of Example 39
<220> FEATURE:
<221> NAME/KEY: MISC_FEATURE
<222> LOCATION: (1)..(1)
<223> OTHER INFORMATION: 2Nal
<220> FEATURE:
<221> NAME/KEY: MISC_FEATURE
<222> LOCATION: (8)..(8)
<223> OTHER INFORMATION: Nle
<220> FEATURE:
<221> NAME/KEY: MISC_FEATURE
<222> LOCATION: (12)..(12)
<223> OTHER INFORMATION: Amidation of C-terminal carboxyl group

<400> SEQUENCE: 39

Xaa Ile Ser Gly Arg Asn Trp Xaa Lys Trp Phe Cys
 1               5                  10

<210> SEQ ID NO 40
<211> LENGTH: 12
<212> TYPE: PRT
<213> ORGANISM: Artificial Sequence
<220> FEATURE:
<223> OTHER INFORMATION: Peptide region of compound of Example 40
<220> FEATURE:
<221> NAME/KEY: MISC_FEATURE
<222> LOCATION: (1)..(1)
<223> OTHER INFORMATION: 2Nal
<220> FEATURE:
<221> NAME/KEY: MISC_FEATURE
<222> LOCATION: (12)..(12)
<223> OTHER INFORMATION: Amidation of C-terminal carboxyl group

<400> SEQUENCE: 40

Xaa Ile Ser Gly Arg Asp Trp Val Lys Trp Val Cys
 1               5                  10

<210> SEQ ID NO 41
<211> LENGTH: 12
<212> TYPE: PRT
<213> ORGANISM: Artificial Sequence
<220> FEATURE:
<223> OTHER INFORMATION: Peptide region of compound of Example 41
<220> FEATURE:
<221> NAME/KEY: MISC_FEATURE
<222> LOCATION: (1)..(1)
<223> OTHER INFORMATION: 2Nal
<220> FEATURE:
<221> NAME/KEY: MISC_FEATURE
<222> LOCATION: (12)..(12)
<223> OTHER INFORMATION: Amidation of C-terminal carboxyl group

<400> SEQUENCE: 41

Xaa Ile Ser Gly Arg Asn Trp Val His Trp Val Cys
 1               5                  10

<210> SEQ ID NO 42
<211> LENGTH: 12
<212> TYPE: PRT
<213> ORGANISM: Artificial Sequence
<220> FEATURE:
<223> OTHER INFORMATION: Peptide region of compound of Example 42
<220> FEATURE:
<221> NAME/KEY: MISC_FEATURE
<222> LOCATION: (1)..(1)
<223> OTHER INFORMATION: 2Nal
```

```
<220> FEATURE:
<221> NAME/KEY: MISC_FEATURE
<222> LOCATION: (12)..(12)
<223> OTHER INFORMATION: Amidation of C-terminal carboxyl group

<400> SEQUENCE: 42

Xaa Ile Ser Gly His Asn Trp Val Lys Trp Val Cys
1               5                   10

<210> SEQ ID NO 43
<211> LENGTH: 12
<212> TYPE: PRT
<213> ORGANISM: Artificial Sequence
<220> FEATURE:
<223> OTHER INFORMATION: Peptide region of compound of Example 43
<220> FEATURE:
<221> NAME/KEY: misc_feature
<222> LOCATION: (1)..(1)
<223> OTHER INFORMATION: 2Nal
<220> FEATURE:
<221> NAME/KEY: misc_feature
<222> LOCATION: (12)..(12)
<223> OTHER INFORMATION: Amidation of C-terminal carboxyl group

<400> SEQUENCE: 43

Xaa Ile Ser Gly Lys Asn Trp Val Lys Trp Val Cys
1               5                   10

<210> SEQ ID NO 44
<211> LENGTH: 12
<212> TYPE: PRT
<213> ORGANISM: Artificial Sequence
<220> FEATURE:
<223> OTHER INFORMATION: Peptide region of compound of Example 44
<220> FEATURE:
<221> NAME/KEY: misc_feature
<222> LOCATION: (1)..(1)
<223> OTHER INFORMATION: 2Nal
<220> FEATURE:
<221> NAME/KEY: misc_feature
<222> LOCATION: (12)..(12)
<223> OTHER INFORMATION: Amidation of C-terminal carboxyl group

<400> SEQUENCE: 44

Xaa Ile Ser Gly Ser Asn Trp Val Lys Trp Val Cys
1               5                   10

<210> SEQ ID NO 45
<211> LENGTH: 12
<212> TYPE: PRT
<213> ORGANISM: Artificial Sequence
<220> FEATURE:
<223> OTHER INFORMATION: Peptide region of compound of Example 45
<220> FEATURE:
<221> NAME/KEY: misc_feature
<222> LOCATION: (1)..(1)
<223> OTHER INFORMATION: 2Nal
<220> FEATURE:
<221> NAME/KEY: misc_feature
<222> LOCATION: (8)..(8)
<223> OTHER INFORMATION: Nle
<220> FEATURE:
<221> NAME/KEY: misc_feature
<222> LOCATION: (12)..(12)
<223> OTHER INFORMATION: Amidation of C-terminal carboxyl group

<400> SEQUENCE: 45

Xaa Ile Ser Gly Arg Asp Trp Xaa Lys Trp Val Cys
1               5                   10

<210> SEQ ID NO 46
```

```
<211> LENGTH: 12
<212> TYPE: PRT
<213> ORGANISM: Artificial Sequence
<220> FEATURE:
<223> OTHER INFORMATION: Peptide region of compound of Example 46
<220> FEATURE:
<221> NAME/KEY: misc_feature
<222> LOCATION: (9)..(9)
<223> OTHER INFORMATION: 3MH
<220> FEATURE:
<221> NAME/KEY: misc_feature
<222> LOCATION: (12)..(12)
<223> OTHER INFORMATION: Amidation of C-terminal carboxyl group

<400> SEQUENCE: 46

Phe Ile Ser Gly Arg Asn Trp Val Xaa Trp Val Cys
1               5                   10

<210> SEQ ID NO 47
<211> LENGTH: 12
<212> TYPE: PRT
<213> ORGANISM: Artificial Sequence
<220> FEATURE:
<223> OTHER INFORMATION: Peptide region of compound of Example 47
<220> FEATURE:
<221> NAME/KEY: misc_feature
<222> LOCATION: (9)..(9)
<223> OTHER INFORMATION: AMF
<220> FEATURE:
<221> NAME/KEY: misc_feature
<222> LOCATION: (12)..(12)
<223> OTHER INFORMATION: Amidation of C-terminal carboxyl group

<400> SEQUENCE: 47

Phe Ile Ser Gly Arg Asn Trp Val Xaa Trp Val Cys
1               5                   10

<210> SEQ ID NO 48
<211> LENGTH: 12
<212> TYPE: PRT
<213> ORGANISM: Artificial Sequence
<220> FEATURE:
<223> OTHER INFORMATION: Peptide region of compound of Example 48
<220> FEATURE:
<221> NAME/KEY: misc_feature
<222> LOCATION: (1)..(1)
<223> OTHER INFORMATION: 2Nal
<220> FEATURE:
<221> NAME/KEY: misc_feature
<222> LOCATION: (2)..(2)
<223> OTHER INFORMATION: Nle
<220> FEATURE:
<221> NAME/KEY: misc_feature
<222> LOCATION: (12)..(12)
<223> OTHER INFORMATION: Amidation of C-terminal carboxyl group

<400> SEQUENCE: 48

Xaa Xaa Ser Gly Arg Asn Trp Val Lys Trp Val Cys
1               5                   10

<210> SEQ ID NO 49
<211> LENGTH: 12
<212> TYPE: PRT
<213> ORGANISM: Artificial Sequence
<220> FEATURE:
<223> OTHER INFORMATION: Peptide region of compound of Example 49
<220> FEATURE:
<221> NAME/KEY: misc_feature
<222> LOCATION: (1)..(1)
<223> OTHER INFORMATION: 2Nal
<220> FEATURE:
<221> NAME/KEY: misc_feature
<222> LOCATION: (2)..(2)
```

```
<223> OTHER INFORMATION: Phg
<220> FEATURE:
<221> NAME/KEY: misc_feature
<222> LOCATION: (12)..(12)
<223> OTHER INFORMATION: Amidation of C-terminal carboxyl group

<400> SEQUENCE: 49

Xaa Xaa Ser Gly Arg Asn Trp Val Lys Trp Val Cys
1               5                   10

<210> SEQ ID NO 50
<211> LENGTH: 12
<212> TYPE: PRT
<213> ORGANISM: Artificial Sequence
<220> FEATURE:
<223> OTHER INFORMATION: Peptide region of compound of Example 50
<220> FEATURE:
<221> NAME/KEY: misc_feature
<222> LOCATION: (1)..(1)
<223> OTHER INFORMATION: 2Nal
<220> FEATURE:
<221> NAME/KEY: misc_feature
<222> LOCATION: (2)..(2)
<223> OTHER INFORMATION: Tle
<220> FEATURE:
<221> NAME/KEY: misc_feature
<222> LOCATION: (12)..(12)
<223> OTHER INFORMATION: Amidation of C-terminal carboxyl group

<400> SEQUENCE: 50

Xaa Xaa Ser Gly Arg Asn Trp Val Lys Trp Val Cys
1               5                   10

<210> SEQ ID NO 51
<211> LENGTH: 12
<212> TYPE: PRT
<213> ORGANISM: Artificial Sequence
<220> FEATURE:
<223> OTHER INFORMATION: Peptide region of compound of Example 51
<220> FEATURE:
<221> NAME/KEY: misc_feature
<222> LOCATION: (1)..(1)
<223> OTHER INFORMATION: 2Nal
<220> FEATURE:
<221> NAME/KEY: misc_feature
<222> LOCATION: (8)..(8)
<223> OTHER INFORMATION: Phg
<220> FEATURE:
<221> NAME/KEY: misc_feature
<222> LOCATION: (12)..(12)
<223> OTHER INFORMATION: Amidation of C-terminal carboxyl group

<400> SEQUENCE: 51

Xaa Ile Ser Gly Arg Asn Trp Xaa Lys Trp Val Cys
1               5                   10

<210> SEQ ID NO 52
<211> LENGTH: 12
<212> TYPE: PRT
<213> ORGANISM: Artificial Sequence
<220> FEATURE:
<223> OTHER INFORMATION: Peptide region of compound of Example 52
<220> FEATURE:
<221> NAME/KEY: misc_feature
<222> LOCATION: (1)..(1)
<223> OTHER INFORMATION: 2Nal
<220> FEATURE:
<221> NAME/KEY: misc_feature
<222> LOCATION: (11)..(11)
<223> OTHER INFORMATION: Phg
<220> FEATURE:
<221> NAME/KEY: misc_feature
<222> LOCATION: (12)..(12)
```

-continued

<223> OTHER INFORMATION: Amidation of C-terminal carboxyl group

<400> SEQUENCE: 52

Xaa Ile Ser Gly Arg Asn Trp Val Lys Trp Xaa Cys
1               5                   10

<210> SEQ ID NO 53
<211> LENGTH: 12
<212> TYPE: PRT
<213> ORGANISM: Artificial Sequence
<220> FEATURE:
<223> OTHER INFORMATION: Peptide region of compound of Example 53
<220> FEATURE:
<221> NAME/KEY: misc_feature
<222> LOCATION: (1)..(1)
<223> OTHER INFORMATION: 2Nal
<220> FEATURE:
<221> NAME/KEY: misc_feature
<222> LOCATION: (11)..(11)
<223> OTHER INFORMATION: Tle
<220> FEATURE:
<221> NAME/KEY: misc_feature
<222> LOCATION: (12)..(12)
<223> OTHER INFORMATION: Amidation of C-terminal carboxyl group

<400> SEQUENCE: 53

Xaa Ile Ser Gly Arg Asn Trp Val Lys Trp Xaa Cys
1               5                   10

<210> SEQ ID NO 54
<211> LENGTH: 12
<212> TYPE: PRT
<213> ORGANISM: Artificial Sequence
<220> FEATURE:
<223> OTHER INFORMATION: Peptide region of compound of Example 54
<220> FEATURE:
<221> NAME/KEY: misc_feature
<222> LOCATION: (1)..(1)
<223> OTHER INFORMATION: 2Nal
<220> FEATURE:
<221> NAME/KEY: misc_feature
<222> LOCATION: (12)..(12)
<223> OTHER INFORMATION: Hcy
<220> FEATURE:
<221> NAME/KEY: misc_feature
<222> LOCATION: (12)..(12)
<223> OTHER INFORMATION: Amidation of C-terminal carboxyl group

<400> SEQUENCE: 54

Xaa Ile Ser Gly Arg Asn Trp Val Lys Trp Val Xaa
1               5                   10

<210> SEQ ID NO 55
<211> LENGTH: 12
<212> TYPE: PRT
<213> ORGANISM: Artificial Sequence
<220> FEATURE:
<223> OTHER INFORMATION: Peptide region of compound of Example 55
<220> FEATURE:
<221> NAME/KEY: misc_feature
<222> LOCATION: (1)..(1)
<223> OTHER INFORMATION: 2Nal
<220> FEATURE:
<221> NAME/KEY: misc_feature
<222> LOCATION: (12)..(12)
<223> OTHER INFORMATION: Amidation of C-terminal carboxyl group

<400> SEQUENCE: 55

Xaa Ile Ser Gly Lys Asp Trp Val Lys Trp Val Cys
1               5                   10

```
<210> SEQ ID NO 56
<211> LENGTH: 12
<212> TYPE: PRT
<213> ORGANISM: Artificial Sequence
<220> FEATURE:
<223> OTHER INFORMATION: Peptide region of compound of Example 56
<220> FEATURE:
<221> NAME/KEY: misc_feature
<222> LOCATION: (1)..(1)
<223> OTHER INFORMATION: 2Nal
<220> FEATURE:
<221> NAME/KEY: misc_feature
<222> LOCATION: (7)..(7)
<223> OTHER INFORMATION: 2Nal
<220> FEATURE:
<221> NAME/KEY: misc_feature
<222> LOCATION: (12)..(12)
<223> OTHER INFORMATION: Amidation of C-terminal carboxyl group

<400> SEQUENCE: 56

Xaa Ile Ser Gly Lys Asn Xaa Val Lys Trp Val Cys
1               5                   10

<210> SEQ ID NO 57
<211> LENGTH: 12
<212> TYPE: PRT
<213> ORGANISM: Artificial Sequence
<220> FEATURE:
<223> OTHER INFORMATION: Peptide region of compound of Example 57
<220> FEATURE:
<221> NAME/KEY: misc_feature
<222> LOCATION: (1)..(1)
<223> OTHER INFORMATION: 2Nal
<220> FEATURE:
<221> NAME/KEY: misc_feature
<222> LOCATION: (8)..(8)
<223> OTHER INFORMATION: Nle
<220> FEATURE:
<221> NAME/KEY: misc_feature
<222> LOCATION: (12)..(12)
<223> OTHER INFORMATION: Amidation of C-terminal carboxyl group

<400> SEQUENCE: 57

Xaa Ile Ser Gly Lys Asp Trp Xaa Lys Trp Val Cys
1               5                   10

<210> SEQ ID NO 58
<211> LENGTH: 12
<212> TYPE: PRT
<213> ORGANISM: Artificial Sequence
<220> FEATURE:
<223> OTHER INFORMATION: Peptide region of compound of Example 58
<220> FEATURE:
<221> NAME/KEY: misc_feature
<222> LOCATION: (1)..(1)
<223> OTHER INFORMATION: 2Nal
<220> FEATURE:
<221> NAME/KEY: misc_feature
<222> LOCATION: (8)..(8)
<223> OTHER INFORMATION: Nle
<220> FEATURE:
<221> NAME/KEY: misc_feature
<222> LOCATION: (12)..(12)
<223> OTHER INFORMATION: Amidation of C-terminal carboxyl group

<400> SEQUENCE: 58

Xaa Ile Ser Gly Lys Asp Trp Xaa Arg Trp Val Cys
1               5                   10

<210> SEQ ID NO 59
<211> LENGTH: 12
<212> TYPE: PRT
<213> ORGANISM: Artificial Sequence
```

```
-continued

<220> FEATURE:
<223> OTHER INFORMATION: Peptide region of compound of Example 59
<220> FEATURE:
<221> NAME/KEY: misc_feature
<222> LOCATION: (1)..(1)
<223> OTHER INFORMATION: 2Nal
<220> FEATURE:
<221> NAME/KEY: misc_feature
<222> LOCATION: (8)..(8)
<223> OTHER INFORMATION: Nle
<220> FEATURE:
<221> NAME/KEY: misc_feature
<222> LOCATION: (12)..(12)
<223> OTHER INFORMATION: Amidation of C-terminal carboxyl group

<400> SEQUENCE: 59

Xaa Ile Ser Gly His Asn Trp Xaa Lys Trp Val Cys
1               5                   10

<210> SEQ ID NO 60
<211> LENGTH: 12
<212> TYPE: PRT
<213> ORGANISM: Artificial Sequence
<220> FEATURE:
<223> OTHER INFORMATION: Peptide region of compound of Example 60
<220> FEATURE:
<221> NAME/KEY: misc_feature
<222> LOCATION: (1)..(1)
<223> OTHER INFORMATION: 2Nal
<220> FEATURE:
<221> NAME/KEY: misc_feature
<222> LOCATION: (8)..(8)
<223> OTHER INFORMATION: Ahp
<220> FEATURE:
<221> NAME/KEY: misc_feature
<222> LOCATION: (12)..(12)
<223> OTHER INFORMATION: Amidation of C-terminal carboxyl group

<400> SEQUENCE: 60

Xaa Ile Ser Gly Arg Asp Trp Xaa Lys Trp Val Cys
1               5                   10

<210> SEQ ID NO 61
<211> LENGTH: 12
<212> TYPE: PRT
<213> ORGANISM: Artificial Sequence
<220> FEATURE:
<223> OTHER INFORMATION: Peptide region of compound of Example 61
<220> FEATURE:
<221> NAME/KEY: misc_feature
<222> LOCATION: (1)..(1)
<223> OTHER INFORMATION: 2Nal
<220> FEATURE:
<221> NAME/KEY: misc_feature
<222> LOCATION: (8)..(8)
<223> OTHER INFORMATION: Aoc
<220> FEATURE:
<221> NAME/KEY: misc_feature
<222> LOCATION: (12)..(12)
<223> OTHER INFORMATION: Amidation of C-terminal carboxyl group

<400> SEQUENCE: 61

Xaa Ile Ser Gly Arg Asp Trp Xaa Lys Trp Val Cys
1               5                   10

<210> SEQ ID NO 62
<211> LENGTH: 12
<212> TYPE: PRT
<213> ORGANISM: Artificial Sequence
<220> FEATURE:
<223> OTHER INFORMATION: Peptide region of compound of Example 62
<220> FEATURE:
<221> NAME/KEY: misc_feature
```

```
<222> LOCATION: (1)..(1)
<223> OTHER INFORMATION: 2Nal
<220> FEATURE:
<221> NAME/KEY: misc_feature
<222> LOCATION: (8)..(8)
<223> OTHER INFORMATION: Nle
<220> FEATURE:
<221> NAME/KEY: misc_feature
<222> LOCATION: (12)..(12)
<223> OTHER INFORMATION: Amidation of C-terminal carboxyl group

<400> SEQUENCE: 62

Xaa Ile Gly Gly Arg Asp Trp Xaa Lys Trp Val Cys
1               5                   10

<210> SEQ ID NO 63
<211> LENGTH: 12
<212> TYPE: PRT
<213> ORGANISM: Artificial Sequence
<220> FEATURE:
<223> OTHER INFORMATION: Peptide region of compound of Example 63
<220> FEATURE:
<221> NAME/KEY: misc_feature
<222> LOCATION: (1)..(1)
<223> OTHER INFORMATION: 2Nal
<220> FEATURE:
<221> NAME/KEY: misc_feature
<222> LOCATION: (8)..(8)
<223> OTHER INFORMATION: Nle
<220> FEATURE:
<221> NAME/KEY: misc_feature
<222> LOCATION: (12)..(12)
<223> OTHER INFORMATION: Amidation of C-terminal carboxyl group

<400> SEQUENCE: 63

Xaa Leu Ser Gly Arg Asp Trp Xaa Lys Trp Val Cys
1               5                   10

<210> SEQ ID NO 64
<211> LENGTH: 12
<212> TYPE: PRT
<213> ORGANISM: Artificial Sequence
<220> FEATURE:
<223> OTHER INFORMATION: Peptide region of compound of Example 64
<220> FEATURE:
<221> NAME/KEY: misc_feature
<222> LOCATION: (1)..(1)
<223> OTHER INFORMATION: 2Nal
<220> FEATURE:
<221> NAME/KEY: misc_feature
<222> LOCATION: (8)..(8)
<223> OTHER INFORMATION: Nle
<220> FEATURE:
<221> NAME/KEY: misc_feature
<222> LOCATION: (12)..(12)
<223> OTHER INFORMATION: Amidation of C-terminal carboxyl group

<400> SEQUENCE: 64

Xaa Ile Ser Gly Lys Glu Trp Xaa Lys Trp Val Cys
1               5                   10

<210> SEQ ID NO 65
<211> LENGTH: 12
<212> TYPE: PRT
<213> ORGANISM: Artificial Sequence
<220> FEATURE:
<223> OTHER INFORMATION: Peptide region of compound of Example 65
<220> FEATURE:
<221> NAME/KEY: misc_feature
<222> LOCATION: (12)..(12)
<223> OTHER INFORMATION: Amidation of C-terminal carboxyl group

<400> SEQUENCE: 65
```

```
Phe Ile Ser Gly Arg Asn Trp Val Thr Trp Val Cys
1               5                   10
```

<210> SEQ ID NO 66
<211> LENGTH: 12
<212> TYPE: PRT
<213> ORGANISM: Artificial Sequence
<220> FEATURE:
<223> OTHER INFORMATION: Peptide region of compound of Example 66
<220> FEATURE:
<221> NAME/KEY: misc_feature
<222> LOCATION: (12)..(12)
<223> OTHER INFORMATION: Amidation of C-terminal carboxyl group

<400> SEQUENCE: 66

```
Phe Ile Ser Gly Lys Asn Trp Val Ser Trp Val Cys
1               5                   10
```

<210> SEQ ID NO 67
<211> LENGTH: 12
<212> TYPE: PRT
<213> ORGANISM: Artificial Sequence
<220> FEATURE:
<223> OTHER INFORMATION: Peptide region of compound of Example 67
<220> FEATURE:
<221> NAME/KEY: misc_feature
<222> LOCATION: (1)..(1)
<223> OTHER INFORMATION: 2Nal
<220> FEATURE:
<221> NAME/KEY: misc_feature
<222> LOCATION: (5)..(5)
<223> OTHER INFORMATION: MS
<220> FEATURE:
<221> NAME/KEY: misc_feature
<222> LOCATION: (8)..(8)
<223> OTHER INFORMATION: Nle
<220> FEATURE:
<221> NAME/KEY: misc_feature
<222> LOCATION: (12)..(12)
<223> OTHER INFORMATION: Amidation of C-terminal carboxyl group

<400> SEQUENCE: 67

```
Xaa Ile Ser Gly Xaa Asp Trp Xaa Lys Trp Val Cys
1               5                   10
```

<210> SEQ ID NO 68
<211> LENGTH: 12
<212> TYPE: PRT
<213> ORGANISM: Artificial Sequence
<220> FEATURE:
<223> OTHER INFORMATION: Peptide region of compound of Example 68
<220> FEATURE:
<221> NAME/KEY: misc_feature
<222> LOCATION: (1)..(1)
<223> OTHER INFORMATION: 2Nal
<220> FEATURE:
<221> NAME/KEY: misc_feature
<222> LOCATION: (8)..(8)
<223> OTHER INFORMATION: Nle
<220> FEATURE:
<221> NAME/KEY: misc_feature
<222> LOCATION: (12)..(12)
<223> OTHER INFORMATION: Amidation of C-terminal carboxyl group

<400> SEQUENCE: 68

```
Xaa Ile Ser Gly Pro Asp Trp Xaa Lys Trp Val Cys
1               5                   10
```

<210> SEQ ID NO 69
<211> LENGTH: 12
<212> TYPE: PRT

```
<213> ORGANISM: Artificial Sequence
<220> FEATURE:
<223> OTHER INFORMATION: Peptide region of compound of Example 69
<220> FEATURE:
<221> NAME/KEY: misc_feature
<222> LOCATION: (1)..(1)
<223> OTHER INFORMATION: 2Nal
<220> FEATURE:
<221> NAME/KEY: misc_feature
<222> LOCATION: (5)..(5)
<223> OTHER INFORMATION: Hyp
<220> FEATURE:
<221> NAME/KEY: misc_feature
<222> LOCATION: (8)..(8)
<223> OTHER INFORMATION: Nle
<220> FEATURE:
<221> NAME/KEY: misc_feature
<222> LOCATION: (12)..(12)
<223> OTHER INFORMATION: Amidation of C-terminal carboxyl group

<400> SEQUENCE: 69

Xaa Ile Ser Gly Xaa Asn Trp Xaa His Trp Val Cys
1               5                   10

<210> SEQ ID NO 70
<211> LENGTH: 12
<212> TYPE: PRT
<213> ORGANISM: Artificial Sequence
<220> FEATURE:
<223> OTHER INFORMATION: Peptide region of compound of Example 70
<220> FEATURE:
<221> NAME/KEY: misc_feature
<222> LOCATION: (1)..(1)
<223> OTHER INFORMATION: 2Nal
<220> FEATURE:
<221> NAME/KEY: misc_feature
<222> LOCATION: (5)..(5)
<223> OTHER INFORMATION: MO1
<220> FEATURE:
<221> NAME/KEY: misc_feature
<222> LOCATION: (8)..(8)
<223> OTHER INFORMATION: Nle
<220> FEATURE:
<221> NAME/KEY: misc_feature
<222> LOCATION: (12)..(12)
<223> OTHER INFORMATION: Amidation of C-terminal carboxyl group

<400> SEQUENCE: 70

Xaa Ile Ser Gly Xaa Asp Trp Xaa Lys Trp Val Cys
1               5                   10

<210> SEQ ID NO 71
<211> LENGTH: 12
<212> TYPE: PRT
<213> ORGANISM: Artificial Sequence
<220> FEATURE:
<223> OTHER INFORMATION: Peptide region of compound of Example 71
<220> FEATURE:
<221> NAME/KEY: misc_feature
<222> LOCATION: (1)..(1)
<223> OTHER INFORMATION: 2Nal
<220> FEATURE:
<221> NAME/KEY: misc_feature
<222> LOCATION: (5)..(5)
<223> OTHER INFORMATION: MO2
<220> FEATURE:
<221> NAME/KEY: misc_feature
<222> LOCATION: (8)..(8)
<223> OTHER INFORMATION: Nle
<220> FEATURE:
<221> NAME/KEY: misc_feature
<222> LOCATION: (12)..(12)
<223> OTHER INFORMATION: Amidation of C-terminal carboxyl group

<400> SEQUENCE: 71
```

```
Xaa Ile Ser Gly Xaa Asp Trp Xaa Lys Trp Val Cys
1               5                   10

<210> SEQ ID NO 72
<211> LENGTH: 12
<212> TYPE: PRT
<213> ORGANISM: Artificial Sequence
<220> FEATURE:
<223> OTHER INFORMATION: Peptide region of compound of Example 72
<220> FEATURE:
<221> NAME/KEY: misc_feature
<222> LOCATION: (1)..(1)
<223> OTHER INFORMATION: 2Nal
<220> FEATURE:
<221> NAME/KEY: misc_feature
<222> LOCATION: (5)..(5)
<223> OTHER INFORMATION: Alb
<220> FEATURE:
<221> NAME/KEY: misc_feature
<222> LOCATION: (8)..(8)
<223> OTHER INFORMATION: Nle
<220> FEATURE:
<221> NAME/KEY: misc_feature
<222> LOCATION: (12)..(12)
<223> OTHER INFORMATION: Amidation of C-terminal carboxyl group

<400> SEQUENCE: 72

Xaa Ile Ser Gly Xaa Asp Trp Xaa Lys Trp Val Cys
1               5                   10

<210> SEQ ID NO 73
<211> LENGTH: 12
<212> TYPE: PRT
<213> ORGANISM: Artificial Sequence
<220> FEATURE:
<223> OTHER INFORMATION: Peptide region of compound of Example 73
<220> FEATURE:
<221> NAME/KEY: misc_feature
<222> LOCATION: (1)..(1)
<223> OTHER INFORMATION: 2Nal
<220> FEATURE:
<221> NAME/KEY: misc_feature
<222> LOCATION: (5)..(5)
<223> OTHER INFORMATION: Cit
<220> FEATURE:
<221> NAME/KEY: misc_feature
<222> LOCATION: (8)..(8)
<223> OTHER INFORMATION: Nle
<220> FEATURE:
<221> NAME/KEY: misc_feature
<222> LOCATION: (12)..(12)
<223> OTHER INFORMATION: Amidation of C-terminal carboxyl group

<400> SEQUENCE: 73

Xaa Ile Ser Gly Xaa Asp Trp Xaa Lys Trp Val Cys
1               5                   10

<210> SEQ ID NO 74
<211> LENGTH: 12
<212> TYPE: PRT
<213> ORGANISM: Artificial Sequence
<220> FEATURE:
<223> OTHER INFORMATION: Peptide region of compound of Example 74
<220> FEATURE:
<221> NAME/KEY: misc_feature
<222> LOCATION: (1)..(1)
<223> OTHER INFORMATION: 2Nal
<220> FEATURE:
<221> NAME/KEY: misc_feature
<222> LOCATION: (5)..(5)
<223> OTHER INFORMATION: HCt
<220> FEATURE:
<221> NAME/KEY: misc_feature
```

-continued

<222> LOCATION: (8)..(8)
<223> OTHER INFORMATION: Nle
<220> FEATURE:
<221> NAME/KEY: misc_feature
<222> LOCATION: (12)..(12)
<223> OTHER INFORMATION: Amidation of C-terminal carboxyl group

<400> SEQUENCE: 74

Xaa Ile Ser Gly Xaa Asp Trp Xaa Lys Trp Val Cys
1               5                   10

<210> SEQ ID NO 75
<211> LENGTH: 13
<212> TYPE: PRT
<213> ORGANISM: Artificial Sequence
<220> FEATURE:
<223> OTHER INFORMATION: Peptide region of compound of Example 75
<220> FEATURE:
<221> NAME/KEY: misc_feature
<222> LOCATION: (2)..(2)
<223> OTHER INFORMATION: 2Nal
<220> FEATURE:
<221> NAME/KEY: misc_feature
<222> LOCATION: (9)..(9)
<223> OTHER INFORMATION: Nle
<220> FEATURE:
<221> NAME/KEY: misc_feature
<222> LOCATION: (13)..(13)
<223> OTHER INFORMATION: Amidation of C-terminal carboxyl group

<400> SEQUENCE: 75

Gly Xaa Ile Ser Gly Arg Asp Trp Xaa Lys Trp Val Cys
1               5                   10

<210> SEQ ID NO 76
<211> LENGTH: 13
<212> TYPE: PRT
<213> ORGANISM: Artificial Sequence
<220> FEATURE:
<223> OTHER INFORMATION: Peptide region of compound of Example 76
<220> FEATURE:
<221> NAME/KEY: misc_feature
<222> LOCATION: (2)..(2)
<223> OTHER INFORMATION: 2Nal
<220> FEATURE:
<221> NAME/KEY: misc_feature
<222> LOCATION: (9)..(9)
<223> OTHER INFORMATION: Nle
<220> FEATURE:
<221> NAME/KEY: misc_feature
<222> LOCATION: (13)..(13)
<223> OTHER INFORMATION: Amidation of C-terminal carboxyl group

<400> SEQUENCE: 76

Gly Xaa Ile Ser Gly Lys Asp Trp Xaa Arg Trp Val Cys
1               5                   10

<210> SEQ ID NO 77
<211> LENGTH: 12
<212> TYPE: PRT
<213> ORGANISM: Artificial Sequence
<220> FEATURE:
<223> OTHER INFORMATION: Peptide region of compound of Example 77
<220> FEATURE:
<221> NAME/KEY: misc_feature
<222> LOCATION: (1)..(1)
<223> OTHER INFORMATION: 2Nal
<220> FEATURE:
<221> NAME/KEY: misc_feature
<222> LOCATION: (8)..(8)
<223> OTHER INFORMATION: Nle
<220> FEATURE:
<221> NAME/KEY: misc_feature -continued

```
<222> LOCATION: (12)..(12)
<223> OTHER INFORMATION: C(O)
<220> FEATURE:
<221> NAME/KEY: misc_feature
<222> LOCATION: (12)..(12)
<223> OTHER INFORMATION: Amidation of C-terminal carboxyl group

<400> SEQUENCE: 77

Xaa Ile Ser Gly Arg Asp Trp Xaa Lys Trp Val Xaa
1               5                   10

<210> SEQ ID NO 78
<211> LENGTH: 12
<212> TYPE: PRT
<213> ORGANISM: Artificial Sequence
<220> FEATURE:
<223> OTHER INFORMATION: Peptide region of compound of Example 78
<220> FEATURE:
<221> NAME/KEY: misc_feature
<222> LOCATION: (1)..(1)
<223> OTHER INFORMATION: 2Nal
<220> FEATURE:
<221> NAME/KEY: misc_feature
<222> LOCATION: (8)..(8)
<223> OTHER INFORMATION: Nle
<220> FEATURE:
<221> NAME/KEY: misc_feature
<222> LOCATION: (12)..(12)
<223> OTHER INFORMATION: C(O2)
<220> FEATURE:
<221> NAME/KEY: misc_feature
<222> LOCATION: (12)..(12)
<223> OTHER INFORMATION: Amidation of C-terminal carboxyl group

<400> SEQUENCE: 78

Xaa Ile Ser Gly Arg Asp Trp Xaa Lys Trp Val Xaa
1               5                   10

<210> SEQ ID NO 79
<211> LENGTH: 12
<212> TYPE: PRT
<213> ORGANISM: Artificial Sequence
<220> FEATURE:
<223> OTHER INFORMATION: Peptide region of compound of Example 79
<220> FEATURE:
<221> NAME/KEY: misc_feature
<222> LOCATION: (1)..(1)
<223> OTHER INFORMATION: 2Nal
<220> FEATURE:
<221> NAME/KEY: misc_feature
<222> LOCATION: (8)..(8)
<223> OTHER INFORMATION: Nle
<220> FEATURE:
<221> NAME/KEY: misc_feature
<222> LOCATION: (12)..(12)
<223> OTHER INFORMATION: PEN
<220> FEATURE:
<221> NAME/KEY: misc_feature
<222> LOCATION: (12)..(12)
<223> OTHER INFORMATION: Amidation of C-terminal carboxyl group

<400> SEQUENCE: 79

Xaa Ile Ser Gly Arg Asp Trp Xaa Lys Trp Val Xaa
1               5                   10

<210> SEQ ID NO 80
<211> LENGTH: 13
<212> TYPE: PRT
<213> ORGANISM: Artificial Sequence
<220> FEATURE:
<223> OTHER INFORMATION: Peptide region of compound of Example 80
<220> FEATURE:
<221> NAME/KEY: misc_feature
```

```
<222> LOCATION: (2)..(2)
<223> OTHER INFORMATION: 2Nal
<220> FEATURE:
<221> NAME/KEY: misc_feature
<222> LOCATION: (9)..(9)
<223> OTHER INFORMATION: Nle
<220> FEATURE:
<221> NAME/KEY: misc_feature
<222> LOCATION: (13)..(13)
<223> OTHER INFORMATION: Amidation of C-terminal carboxyl group

<400> SEQUENCE: 80

Ala Xaa Ile Ser Gly Arg Asp Trp Xaa Lys Trp Val Cys
 1               5                  10

<210> SEQ ID NO 81
<211> LENGTH: 13
<212> TYPE: PRT
<213> ORGANISM: Artificial Sequence
<220> FEATURE:
<223> OTHER INFORMATION: Peptide region of compound of Example 81
<220> FEATURE:
<221> NAME/KEY: misc_feature
<222> LOCATION: (2)..(2)
<223> OTHER INFORMATION: 2Nal
<220> FEATURE:
<221> NAME/KEY: misc_feature
<222> LOCATION: (9)..(9)
<223> OTHER INFORMATION: Nle
<220> FEATURE:
<221> NAME/KEY: misc_feature
<222> LOCATION: (13)..(13)
<223> OTHER INFORMATION: Amidation of C-terminal carboxyl group

<400> SEQUENCE: 81

Val Xaa Ile Ser Gly Arg Asp Trp Xaa Lys Trp Val Cys
 1               5                  10

<210> SEQ ID NO 82
<211> LENGTH: 13
<212> TYPE: PRT
<213> ORGANISM: Artificial Sequence
<220> FEATURE:
<223> OTHER INFORMATION: Peptide region of compound of Example 82
<220> FEATURE:
<221> NAME/KEY: misc_feature
<222> LOCATION: (2)..(2)
<223> OTHER INFORMATION: 2Nal
<220> FEATURE:
<221> NAME/KEY: misc_feature
<222> LOCATION: (9)..(9)
<223> OTHER INFORMATION: Nle
<220> FEATURE:
<221> NAME/KEY: misc_feature
<222> LOCATION: (13)..(13)
<223> OTHER INFORMATION: Amidation of C-terminal carboxyl group

<400> SEQUENCE: 82

Leu Xaa Ile Ser Gly Arg Asp Trp Xaa Lys Trp Val Cys
 1               5                  10

<210> SEQ ID NO 83
<211> LENGTH: 13
<212> TYPE: PRT
<213> ORGANISM: Artificial Sequence
<220> FEATURE:
<223> OTHER INFORMATION: Peptide region of compound of Example 83
<220> FEATURE:
<221> NAME/KEY: misc_feature
<222> LOCATION: (2)..(2)
<223> OTHER INFORMATION: 2Nal
<220> FEATURE:
<221> NAME/KEY: misc_feature
```

-continued

```
<222> LOCATION: (9)..(9)
<223> OTHER INFORMATION: Nle
<220> FEATURE:
<221> NAME/KEY: misc_feature
<222> LOCATION: (13)..(13)
<223> OTHER INFORMATION: Amidation of C-terminal carboxyl group

<400> SEQUENCE: 83

Ile Xaa Ile Ser Gly Arg Asp Trp Xaa Lys Trp Val Cys
1               5                   10

<210> SEQ ID NO 84
<211> LENGTH: 13
<212> TYPE: PRT
<213> ORGANISM: Artificial Sequence
<220> FEATURE:
<223> OTHER INFORMATION: Peptide region of compound of Example 84
<220> FEATURE:
<221> NAME/KEY: misc_feature
<222> LOCATION: (2)..(2)
<223> OTHER INFORMATION: 2Nal
<220> FEATURE:
<221> NAME/KEY: misc_feature
<222> LOCATION: (9)..(9)
<223> OTHER INFORMATION: Nle
<220> FEATURE:
<221> NAME/KEY: misc_feature
<222> LOCATION: (13)..(13)
<223> OTHER INFORMATION: Amidation of C-terminal carboxyl group

<400> SEQUENCE: 84

Met Xaa Ile Ser Gly Arg Asp Trp Xaa Lys Trp Val Cys
1               5                   10

<210> SEQ ID NO 85
<211> LENGTH: 13
<212> TYPE: PRT
<213> ORGANISM: Artificial Sequence
<220> FEATURE:
<223> OTHER INFORMATION: Peptide region of compound of Example 85
<220> FEATURE:
<221> NAME/KEY: misc_feature
<222> LOCATION: (2)..(2)
<223> OTHER INFORMATION: 2Nal
<220> FEATURE:
<221> NAME/KEY: misc_feature
<222> LOCATION: (9)..(9)
<223> OTHER INFORMATION: Nle
<220> FEATURE:
<221> NAME/KEY: misc_feature
<222> LOCATION: (13)..(13)
<223> OTHER INFORMATION: Amidation of C-terminal carboxyl group

<400> SEQUENCE: 85

Thr Xaa Ile Ser Gly Arg Asp Trp Xaa Lys Trp Val Cys
1               5                   10

<210> SEQ ID NO 86
<211> LENGTH: 13
<212> TYPE: PRT
<213> ORGANISM: Artificial Sequence
<220> FEATURE:
<223> OTHER INFORMATION: Peptide region of compound of Example 86
<220> FEATURE:
<221> NAME/KEY: misc_feature
<222> LOCATION: (2)..(2)
<223> OTHER INFORMATION: 2Nal
<220> FEATURE:
<221> NAME/KEY: misc_feature
<222> LOCATION: (9)..(9)
<223> OTHER INFORMATION: Nle
<220> FEATURE:
<221> NAME/KEY: misc_feature
```

<222> LOCATION: (13)..(13)
<223> OTHER INFORMATION: Amidation of C-terminal carboxyl group

<400> SEQUENCE: 86

Gln Xaa Ile Ser Gly Arg Asp Trp Xaa Lys Trp Val Cys
1               5                   10

<210> SEQ ID NO 87
<211> LENGTH: 13
<212> TYPE: PRT
<213> ORGANISM: Artificial Sequence
<220> FEATURE:
<223> OTHER INFORMATION: Peptide region of compound of Example 87
<220> FEATURE:
<221> NAME/KEY: misc_feature
<222> LOCATION: (2)..(2)
<223> OTHER INFORMATION: 2Nal
<220> FEATURE:
<221> NAME/KEY: misc_feature
<222> LOCATION: (9)..(9)
<223> OTHER INFORMATION: Nle
<220> FEATURE:
<221> NAME/KEY: misc_feature
<222> LOCATION: (13)..(13)
<223> OTHER INFORMATION: Amidation of C-terminal carboxyl group

<400> SEQUENCE: 87

Phe Xaa Ile Ser Gly Arg Asp Trp Xaa Lys Trp Val Cys
1               5                   10

<210> SEQ ID NO 88
<211> LENGTH: 13
<212> TYPE: PRT
<213> ORGANISM: Artificial Sequence
<220> FEATURE:
<223> OTHER INFORMATION: Peptide region of compound of Example 88
<220> FEATURE:
<221> NAME/KEY: misc_feature
<222> LOCATION: (2)..(2)
<223> OTHER INFORMATION: 2Nal
<220> FEATURE:
<221> NAME/KEY: misc_feature
<222> LOCATION: (9)..(9)
<223> OTHER INFORMATION: Nle
<220> FEATURE:
<221> NAME/KEY: misc_feature
<222> LOCATION: (13)..(13)
<223> OTHER INFORMATION: Amidation of C-terminal carboxyl group

<400> SEQUENCE: 88

Tyr Xaa Ile Ser Gly Arg Asp Trp Xaa Lys Trp Val Cys
1               5                   10

<210> SEQ ID NO 89
<211> LENGTH: 13
<212> TYPE: PRT
<213> ORGANISM: Artificial Sequence
<220> FEATURE:
<223> OTHER INFORMATION: Peptide region of compound of Example 89
<220> FEATURE:
<221> NAME/KEY: misc_feature
<222> LOCATION: (2)..(2)
<223> OTHER INFORMATION: 2Nal
<220> FEATURE:
<221> NAME/KEY: misc_feature
<222> LOCATION: (9)..(9)
<223> OTHER INFORMATION: Nle
<220> FEATURE:
<221> NAME/KEY: misc_feature
<222> LOCATION: (13)..(13)
<223> OTHER INFORMATION: Amidation of C-terminal carboxyl group

<400> SEQUENCE: 89

```
Trp Xaa Ile Ser Gly Arg Asp Trp Xaa Lys Trp Val Cys
1               5                   10
```

<210> SEQ ID NO 90
<211> LENGTH: 13
<212> TYPE: PRT
<213> ORGANISM: Artificial Sequence
<220> FEATURE:
<223> OTHER INFORMATION: Peptide region of compound of Example 90
<220> FEATURE:
<221> NAME/KEY: misc_feature
<222> LOCATION: (2)..(2)
<223> OTHER INFORMATION: 2Nal
<220> FEATURE:
<221> NAME/KEY: misc_feature
<222> LOCATION: (9)..(9)
<223> OTHER INFORMATION: Nle
<220> FEATURE:
<221> NAME/KEY: misc_feature
<222> LOCATION: (13)..(13)
<223> OTHER INFORMATION: Amidation of C-terminal carboxyl group

<400> SEQUENCE: 90

```
Lys Xaa Ile Ser Gly Arg Asp Trp Xaa Lys Trp Val Cys
1               5                   10
```

<210> SEQ ID NO 91
<211> LENGTH: 13
<212> TYPE: PRT
<213> ORGANISM: Artificial Sequence
<220> FEATURE:
<223> OTHER INFORMATION: Peptide region of compound of Example 91
<220> FEATURE:
<221> NAME/KEY: misc_feature
<222> LOCATION: (2)..(2)
<223> OTHER INFORMATION: 2Nal
<220> FEATURE:
<221> NAME/KEY: misc_feature
<222> LOCATION: (9)..(9)
<223> OTHER INFORMATION: Nle
<220> FEATURE:
<221> NAME/KEY: misc_feature
<222> LOCATION: (13)..(13)
<223> OTHER INFORMATION: Amidation of C-terminal carboxyl group

<400> SEQUENCE: 91

```
His Xaa Ile Ser Gly Arg Asp Trp Xaa Lys Trp Val Cys
1               5                   10
```

<210> SEQ ID NO 92
<211> LENGTH: 13
<212> TYPE: PRT
<213> ORGANISM: Artificial Sequence
<220> FEATURE:
<223> OTHER INFORMATION: Peptide region of compound of Example 92
<220> FEATURE:
<221> NAME/KEY: misc_feature
<222> LOCATION: (2)..(2)
<223> OTHER INFORMATION: 2Nal
<220> FEATURE:
<221> NAME/KEY: misc_feature
<222> LOCATION: (9)..(9)
<223> OTHER INFORMATION: Nle
<220> FEATURE:
<221> NAME/KEY: misc_feature
<222> LOCATION: (13)..(13)
<223> OTHER INFORMATION: Amidation of C-terminal carboxyl group

<400> SEQUENCE: 92

```
Ser Xaa Ile Ser Gly Lys Asp Trp Xaa Arg Trp Val Cys
1               5                   10
```

<210> SEQ ID NO 93
<211> LENGTH: 13
<212> TYPE: PRT
<213> ORGANISM: Artificial Sequence
<220> FEATURE:
<223> OTHER INFORMATION: Peptide region of compound of Example 93
<220> FEATURE:
<221> NAME/KEY: misc_feature
<222> LOCATION: (2)..(2)
<223> OTHER INFORMATION: 2Nal
<220> FEATURE:
<221> NAME/KEY: misc_feature
<222> LOCATION: (9)..(9)
<223> OTHER INFORMATION: Nle
<220> FEATURE:
<221> NAME/KEY: misc_feature
<222> LOCATION: (13)..(13)
<223> OTHER INFORMATION: Amidation of C-terminal carboxyl group

<400> SEQUENCE: 93

Asn Xaa Ile Ser Gly Lys Asp Trp Xaa Arg Trp Val Cys
1               5                   10

<210> SEQ ID NO 94
<211> LENGTH: 13
<212> TYPE: PRT
<213> ORGANISM: Artificial Sequence
<220> FEATURE:
<223> OTHER INFORMATION: Peptide region of compound of Example 94
<220> FEATURE:
<221> NAME/KEY: misc_feature
<222> LOCATION: (2)..(2)
<223> OTHER INFORMATION: 2Nal
<220> FEATURE:
<221> NAME/KEY: misc_feature
<222> LOCATION: (9)..(9)
<223> OTHER INFORMATION: Nle
<220> FEATURE:
<221> NAME/KEY: misc_feature
<222> LOCATION: (13)..(13)
<223> OTHER INFORMATION: Amidation of C-terminal carboxyl group

<400> SEQUENCE: 94

Phe Xaa Ile Ser Gly Lys Asp Trp Xaa Arg Trp Val Cys
1               5                   10

<210> SEQ ID NO 95
<211> LENGTH: 13
<212> TYPE: PRT
<213> ORGANISM: Artificial Sequence
<220> FEATURE:
<223> OTHER INFORMATION: Peptide region of compound of Example 95
<220> FEATURE:
<221> NAME/KEY: misc_feature
<222> LOCATION: (2)..(2)
<223> OTHER INFORMATION: 2Nal
<220> FEATURE:
<221> NAME/KEY: misc_feature
<222> LOCATION: (9)..(9)
<223> OTHER INFORMATION: Nle
<220> FEATURE:
<221> NAME/KEY: misc_feature
<222> LOCATION: (13)..(13)
<223> OTHER INFORMATION: Amidation of C-terminal carboxyl group

<400> SEQUENCE: 95

Lys Xaa Ile Ser Gly Lys Asp Trp Xaa Arg Trp Val Cys
1               5                   10

<210> SEQ ID NO 96
<211> LENGTH: 13
<212> TYPE: PRT

```
<213> ORGANISM: Artificial Sequence
<220> FEATURE:
<223> OTHER INFORMATION: Peptide region of compound of Example 96
<220> FEATURE:
<221> NAME/KEY: misc_feature
<222> LOCATION: (2)..(2)
<223> OTHER INFORMATION: 2Nal
<220> FEATURE:
<221> NAME/KEY: misc_feature
<222> LOCATION: (9)..(9)
<223> OTHER INFORMATION: Nle
<220> FEATURE:
<221> NAME/KEY: misc_feature
<222> LOCATION: (13)..(13)
<223> OTHER INFORMATION: Amidation of C-terminal carboxyl group

<400> SEQUENCE: 96

Arg Xaa Ile Ser Gly Lys Asp Trp Xaa Arg Trp Val Cys
1               5                   10

<210> SEQ ID NO 97
<211> LENGTH: 13
<212> TYPE: PRT
<213> ORGANISM: Artificial Sequence
<220> FEATURE:
<223> OTHER INFORMATION: Peptide region of compound of Example 97
<220> FEATURE:
<221> NAME/KEY: misc_feature
<222> LOCATION: (2)..(2)
<223> OTHER INFORMATION: 2Nal
<220> FEATURE:
<221> NAME/KEY: misc_feature
<222> LOCATION: (9)..(9)
<223> OTHER INFORMATION: Nle
<220> FEATURE:
<221> NAME/KEY: misc_feature
<222> LOCATION: (13)..(13)
<223> OTHER INFORMATION: Amidation of C-terminal carboxyl group

<400> SEQUENCE: 97

Cys Xaa Ile Ser Gly Arg Asp Trp Xaa Lys Trp Val Cys
1               5                   10

<210> SEQ ID NO 98
<211> LENGTH: 12
<212> TYPE: PRT
<213> ORGANISM: Artificial Sequence
<220> FEATURE:
<223> OTHER INFORMATION: Peptide region of compound of Example 99
<220> FEATURE:
<221> NAME/KEY: MISC_FEATURE
<222> LOCATION: (1)..(1)
<223> OTHER INFORMATION: 2Nal
<220> FEATURE:
<221> NAME/KEY: MISC_FEATURE
<222> LOCATION: (12)..(12)
<223> OTHER INFORMATION: Amidation of C-terminal carboxyl group

<400> SEQUENCE: 98

Xaa Arg Ser Gly Lys Asn Trp Val Val Trp Val Cys
1               5                   10

<210> SEQ ID NO 99
<211> LENGTH: 12
<212> TYPE: PRT
<213> ORGANISM: Artificial Sequence
<220> FEATURE:
<223> OTHER INFORMATION: Peptide region of compound of Example 99
<220> FEATURE:
<221> NAME/KEY: MISC_FEATURE
<222> LOCATION: (1)..(1)
<223> OTHER INFORMATION: 2Nal
<220> FEATURE:
```

```
<221> NAME/KEY: MISC_FEATURE
<222> LOCATION: (12)..(12)
<223> OTHER INFORMATION: Amidation of C-terminal carboxyl group

<400> SEQUENCE: 99

Xaa Arg Ser Gly Lys Asp Trp Val Val Trp Val Cys
1               5                   10

<210> SEQ ID NO 100
<211> LENGTH: 12
<212> TYPE: PRT
<213> ORGANISM: Artificial Sequence
<220> FEATURE:
<223> OTHER INFORMATION: Peptide region of compound of Example 100
<220> FEATURE:
<221> NAME/KEY: MISC_FEATURE
<222> LOCATION: (1)..(1)
<223> OTHER INFORMATION: 2Nal
<220> FEATURE:
<221> NAME/KEY: MISC_FEATURE
<222> LOCATION: (8)..(8)
<223> OTHER INFORMATION: Nle
<220> FEATURE:
<221> NAME/KEY: MISC_FEATURE
<222> LOCATION: (12)..(2)
<223> OTHER INFORMATION: Amidation of C-terminal carboxyl group

<400> SEQUENCE: 100

Xaa Arg Ser Gly His Asn Trp Xaa Val Trp Val Cys
1               5                   10

<210> SEQ ID NO 101
<211> LENGTH: 12
<212> TYPE: PRT
<213> ORGANISM: Artificial Sequence
<220> FEATURE:
<223> OTHER INFORMATION: Peptide region of compound of Example 101
<220> FEATURE:
<221> NAME/KEY: MISC_FEATURE
<222> LOCATION: (1)..(1)
<223> OTHER INFORMATION: 2Nal
<220> FEATURE:
<221> NAME/KEY: MISC_FEATURE
<222> LOCATION: (8)..(8)
<223> OTHER INFORMATION: Nle
<220> FEATURE:
<221> NAME/KEY: MISC_FEATURE
<222> LOCATION: (12)..(12)
<223> OTHER INFORMATION: Amidation of C-terminal carboxyl group

<400> SEQUENCE: 101

Xaa Arg Ser Gly His Asp Trp Xaa Val Trp Val Cys
1               5                   10

<210> SEQ ID NO 102
<211> LENGTH: 12
<212> TYPE: PRT
<213> ORGANISM: Artificial Sequence
<220> FEATURE:
<223> OTHER INFORMATION: Peptide region of compound of Example 102
<220> FEATURE:
<221> NAME/KEY: MISC_FEATURE
<222> LOCATION: (1)..(1)
<223> OTHER INFORMATION: 2Nal
<220> FEATURE:
<221> NAME/KEY: MISC_FEATURE
<222> LOCATION: (9)..(9)
<223> OTHER INFORMATION: Phg
<220> FEATURE:
<221> NAME/KEY: MISC_FEATURE
<222> LOCATION: (12)..(2)
<223> OTHER INFORMATION: Amidation of C-terminal carboxyl group
```

```
<400> SEQUENCE: 102

Xaa Arg Ser Gly Lys Asp Trp Val Xaa Trp Val Cys
1               5                   10

<210> SEQ ID NO 103
<211> LENGTH: 12
<212> TYPE: PRT
<213> ORGANISM: Artificial Sequence
<220> FEATURE:
<223> OTHER INFORMATION: Peptide region of compound of Example 103
<220> FEATURE:
<221> NAME/KEY: MISC_FEATURE
<222> LOCATION: (1)..(1)
<223> OTHER INFORMATION: 2Nal
<220> FEATURE:
<221> NAME/KEY: MISC_FEATURE
<222> LOCATION: (8)..(8)
<223> OTHER INFORMATION: Nle
<220> FEATURE:
<221> NAME/KEY: MISC_FEATURE
<222> LOCATION: (9)..(9)
<223> OTHER INFORMATION: Phg
<220> FEATURE:
<221> NAME/KEY: MISC_FEATURE
<222> LOCATION: (12)..(12)
<223> OTHER INFORMATION: Amidation of C-terminal carboxyl group

<400> SEQUENCE: 103

Xaa Arg Ser Gly Lys Asn Trp Xaa Xaa Trp Val Cys
1               5                   10

<210> SEQ ID NO 104
<211> LENGTH: 12
<212> TYPE: PRT
<213> ORGANISM: Artificial Sequence
<220> FEATURE:
<223> OTHER INFORMATION: Peptide region of compound of Example 104
<220> FEATURE:
<221> NAME/KEY: MISC_FEATURE
<222> LOCATION: (1)..(1)
<223> OTHER INFORMATION: 2Nal
<220> FEATURE:
<221> NAME/KEY: MISC_FEATURE
<222> LOCATION: (8)..(8)
<223> OTHER INFORMATION: Nle
<220> FEATURE:
<221> NAME/KEY: MISC_FEATURE
<222> LOCATION: (9)..(9)
<223> OTHER INFORMATION: Phg
<220> FEATURE:
<221> NAME/KEY: MISC_FEATURE
<222> LOCATION: (12)..(12)
<223> OTHER INFORMATION: Amidation of C-terminal carboxyl group

<400> SEQUENCE: 104

Xaa Arg Ser Gly Lys Asp Trp Xaa Xaa Trp Val Cys
1               5                   10
```